US012516107B2

(12) United States Patent
Wu et al.

(10) Patent No.: US 12,516,107 B2
(45) Date of Patent: Jan. 6, 2026

(54) POTENT NEUTRALIZING ANTIBODIES FOR PREVENTION AND TREATMENT OF COVID-19

(71) Applicant: Academia Sinica, Taipei (TW)

(72) Inventors: Han-Chung Wu, Taipei (TW); Yi-Ling Lin, New Taipei (TW); Mi-Hua Tao, Taipei (TW); Shang-Te Danny Hsu, New Taipei (TW)

(73) Assignee: ACADEMIA SINICA, Taipei (TW)

( * ) Notice: Subject to any disclaimer, the term of this patent is extended or adjusted under 35 U.S.C. 154(b) by 540 days.

(21) Appl. No.: 18/028,687

(22) PCT Filed: Sep. 29, 2021

(86) PCT No.: PCT/US2021/052650
§ 371 (c)(1),
(2) Date: Mar. 27, 2023

(87) PCT Pub. No.: WO2022/072495
PCT Pub. Date: Apr. 7, 2022

(65) Prior Publication Data

US 2025/0270296 A1 Aug. 28, 2025

Related U.S. Application Data

(60) Provisional application No. 63/167,109, filed on Mar. 28, 2021, provisional application No. 63/086,206, filed on Oct. 1, 2020.

(51) Int. Cl.
*C07K 16/10* (2006.01)

(52) U.S. Cl.
CPC .................................. *C07K 16/1003* (2023.08)

(58) Field of Classification Search
CPC .................................................. C07K 16/1003
See application file for complete search history.

(56) References Cited

U.S. PATENT DOCUMENTS

2013/0224187 A1 8/2013 Rother et al.
2014/0248238 A1 9/2014 Wilson, Jr. et al.
2018/0327506 A1 11/2018 Karsunky et al.

FOREIGN PATENT DOCUMENTS

CN 111153988 A 5/2020

OTHER PUBLICATIONS

International Search Report for PCT/US2021/052650, dated Jul. 1, 2022.
Written Opinion of International Search Authority for PCT/US2021/052650, dated Jul. 1, 2022.
Receptor-binding domain-specific human neutralizing monoclonal antibodies against SARS-CoV and SARS-CoV-2. Fei Yu et al., Signal Transduction and Targeted Therapy (2020) 6:212.

*Primary Examiner* — Prema M Mertz
(74) *Attorney, Agent, or Firm* — Hsiu-Ming Saunders; INTELLECTUAL PROPERTY CONNECTIONS, INC.

(57) ABSTRACT

Potent neutralizing antibodies for prevention and treatment of covid-19. Human chimeric antibodies (RBD-chAbs) specifically against SARS-COV-2 Spike(S) receptor-binding domain (RBD) are disclosed. Antibody cocktails or vaccine compositions comprising the RBD-chAbs are also disclosed. The RBD-chAbs, the antibody cocktails, and the vaccine compositions are effective for protection and/or treatment of COVID-19 and are potent against COVID-19 variants including United Kingdom variant B.1.1.7 (Alpha), South African variant B.1.351 (Beta), Brazil variant P1 (Gamma), California variant B.1.429 (Epsilon), New York variant B.1.526 (Iota), Indian variants B.1.617.1 (Kappa) and B.1.617.2 (Delta).

20 Claims, 14 Drawing Sheets

Specification includes a Sequence Listing.

FIG. 1
A
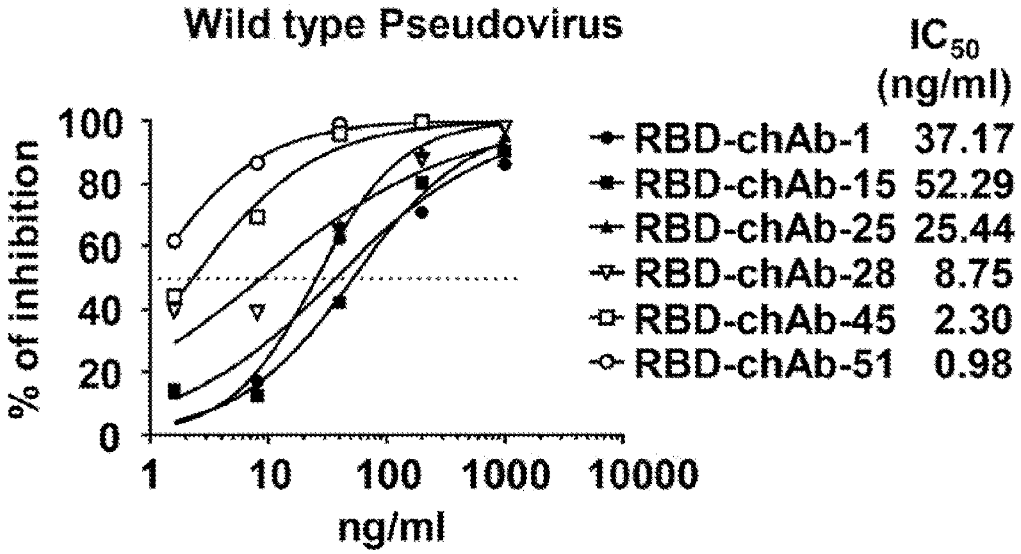
B
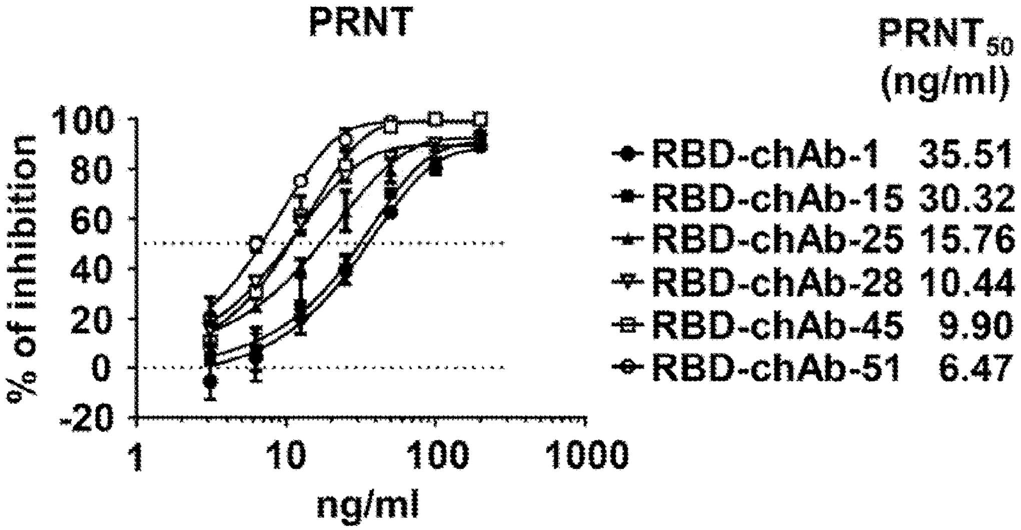
C
| | $k_a$ ($M^{-1} \times s^{-1}$) | $k_d$ ($s^{-1}$) | $K_D$ (M) |
|---|---|---|---|
| RBD-chAb-1 | $5.27 \times 10^{5}$ | $3.39 \times 10^{-5}$ | $6.43 \times 10^{-11}$ |
| RBD-chAb-15 | $5.25 \times 10^{5}$ | $7.27 \times 10^{-4}$ | $1.39 \times 10^{-9}$ |
| RBD-chAb-25 | $9.28 \times 10^{5}$ | $5.87 \times 10^{-3}$ | $6.33 \times 10^{-9}$ |
| RBD-chAb-28 | $2.02 \times 10^{6}$ | $1.00 \times 10^{-3}$ | $4.96 \times 10^{-10}$ |
| RBD-chAb-45 | $9.97 \times 10^{5}$ | $2.82 \times 10^{-4}$ | $2.82 \times 10^{-10}$ |
| RBD-chAb-51 | $1.22 \times 10^{6}$ | $2.24 \times 10^{-4}$ | $1.84 \times 10^{-10}$ |

| RBD-chAb | Epitope |
|---|---|
| 25 | Y453/N501 |
| 1,15,28 | Y453 |
| 45,51 | F486 |

FIG. 13A

Table 1

| No | Ab name | FR1 | CDR1 | FR2 | CDR2 | FR3 | CDR3 | FR4 |
|---|---|---|---|---|---|---|---|---|
| 1 | **RBD-mAb-1** *SEQ ID #92 | EVQLQQSGPQLVRPGASMKISCKAS SEQ ID NO: 4 | **GYSFTTYW** SEQ ID NO: 5 | MHWVKQRPGQGLQWIGM SEQ ID NO: 6 | **IDPSDSET** SEQ ID NO: 7 | RLNQKFKDKATLTVDKSSSTAYMQLSSPTSEDSAVYYC SEQ ID NO: 8 | **ARDFDYDRTMDY** SEQ ID NO: 9 | WGQGTSVTVSS SEQ ID NO: 10 |
| 2 | **RBD-mAb-15** SEQ ID #86 | EVQLEESGPGLVQPSQSLSITCTVS SEQ ID NO: 11 | **DFSLTTYG** SEQ ID # 12 | VHWVRQSPGKGLEWLGV SEQ ID # 13 | **IWSGGST** SEQ ID # 14 | DYNAAFISRLSISKDNSKSQVFFKMNSLQTNDTAIYYC SEQ ID # 15 | **ARMGDGYYVGAMDY** SEQ ID # 16 | WGQGTSVTVSS SEQ ID # 17 |
| 3 | **RBD-mAb-25** SEQ ID #88 | EVQLEESGGGLVKPGGSLKLSCAAS SEQ ID NO: 18 | **GFTFSSYT** SEQ ID # 19 | MSWVRQSPEKRLEWVAE SEQ ID # 20 | **ISSGGTYT** SEQ ID # 21 | NYPDTATGRFTISRDNAKNTLYLEMSSLRSEDTAMYYC SEQ ID # 22 | **ANFGNYEEIAY** SEQ ID # 23 | WGQGTLVTVSA SEQ ID # 24 |
| 4 | **RBD-mAb-28** SEQ ID #84 | QVQLQQPGTELVMPGASVKMSCKAS SEQ ID NO: 25 | **GYTFTDYY** SEQ ID # 26 | LHWMKQRPGQGLEWIGA SEQ ID # 27 | **IDSSDSYT** SEQ ID # 28 | DYNQNFKGKATLTVDESSSTAYMHLSSLTSEDSAVYYC SEQ ID # 29 | **ARGKDAYDRRPWFAY** SEQ ID # 30 | WGQGTLVTVSA SEQ ID # 31 |
| 5 | **RBD-mAb-45** SEQ ID #82 | EVQLQQSGPELVKPGASVKISCKTS SEQ ID NO: 32 | **GYTFTEYT** SEQ ID # 33 | IYWVKQSLGKSLEWIGG SEQ ID # 34 | **NNPNNDDT** SEQ ID # 35 | TYKQFFKGKATLTVDKSSSTAYMELRSLTSEDSAVYYC SEQ ID # 36 | **ARDGYPYYYALDF** SEQ ID # 37 | WGQGTSVTVSS SEQ ID # 38 |
| 6 | **RBD-mAb-51** SEQ ID #90 | EVQLQQSGPELVKPGASAKISCKTS SEQ ID NO: 39 | **GYTFTEYT** SEQ ID # 40 | MYWVKQSHGKSLEWIGG SEQ ID # 41 | **INPNNGDT** SEQ ID # 42 | TYNQTFKGKATLTVDKSSSTAYMELRSLTSEDSAVYYC SEQ ID # 43 | **ARDGYPFYYALDY** SEQ ID # 44 | WGQGISVTVSS SEQ ID # 45 |

*: VH SEQ ID NO:

FIG. 13B

Table 2

| No | Ab name | FR1 | CDR1 | FR2 | CDR2 | FR3 | CDR3 | FR4 |
|---|---|---|---|---|---|---|---|---|
| 1 | **RBD-mAb-1** **SEQ ID #93 | DIVMSQSPSSLAVSVGEKVTMSCKSS SEQ ID NO: 46 | **QSLLFSSSQKNY** SEQ ID # 47 | LAWYQQKAGQSPKLLIF SEQ ID NO: 48 | **WAS** | TRESGVPDRFTGSGSGTDFTLTISSVKAEDLAIYYC SEQ ID NO: 49 | **KQYYKYPLT** SEQ ID NO: 50 | FGAGTKLDIK SEQ ID # 51 |
| 2 | **RBD-mAb-15** SEQ ID #87 | DIQLTQSPAILSVSPGERVSFSCRAS SEQ ID NO: 52 | **QSIGTS** SEQ ID # 53 | IHWYQQRTNGSPRHLIK SEQ ID NO: 54 | **YAS** | ESISGIPSRFSGSGSGTDFTLTINGVESEDIADYYC SEQ ID NO: 55 | **QQGHNWPLT** SEQ ID NO: 56 | FGAGTKLDIK SEQ ID # 57 |
| 3 | **RBD-mAb-25** SEQ ID #89 | QIVLTQSPAIMSVSLGERVTMTCTAS SEQ ID NO: 58 | **SSVSSSY** SEQ ID # 59 | LHWYQQKPGSSPKLWIY SEQ ID NO: 60 | **STS** | NLASGVPARFSGSGSGTSYSLTISSMEAEDAATYYC SEQ ID NO: 61 | **HQYHRSPYT** SEQ ID NO: 62 | FGGGTKLEIK SEQ ID # 63 |
| 4 | **RBD-mAb-28** SEQ ID #85 | DIQMTQTTSSLSASLGDRVTISCSAS SEQ ID NO: 64 | **QGIRYY** SEQ ID # 65 | LNWYQQKPDGTVKLLIY SEQ ID NO: 66 | **YTS** | NLHSGVPSRFSGSGSGTDYSLTISNLEPEDIATYYC SEQ ID NO: 67 | **QQYNKLPYT** SEQ ID NO: 68 | FGGGTKLDIK SEQ ID # 69 |
| 5 | **RBD-mAb-45** SEQ ID #83 | DILMTQSQKFMSTSVGDRVSVTCKSS SEQ ID NO: 70 | **QNVGTN** SEQ ID # 71 | VAWYQQKPGQSPKALIY SEQ ID NO: 72 | **SAS** | YRYSGVPDHFTGSGSGTDFTLTISNVQSADLAEYFC SEQ ID NO: 73 | **QQYNNYPWT** SEQ ID NO: 74 | FGGGTKLDIK SEQ ID # 75 |
| 6 | **RBD-mAb-51** SEQ ID #91 | DIVMTQSQKFMSTSVGDRVSVTCKAR SEQ ID NO: 76 | **QIVGTN** SEQ ID # 77 | VAWYQQKPGQSPKALIY SEQ ID NO: 78 | **SAS** | YRYSGVPDRFTGSGSGTDFTLTITNVHSEDLAEFFC SEQ ID NO: 79 | **HQYNSYPWT** SEQ ID NO: 80 | FGGGTKLDIK SEQ ID # 81 |

**: VL SEQ ID NO:

| | SARS-CoV2 pseudovirus IC50 (ng/ml) | | |
|---|---|---|---|
| | **D614G** | **B.1.1.7 (United Kingdom)** | **B.1.351 (South Africa)** |
| **RBD-chAb-25** | 19.75 ± 2.42 | N/A | N/A |
| **RBD-chAb-45** | 2.96 ± 0.20 | 5.47 ± 0.60 | 2.19 ± 0.31 |
| **RBD-chAb-25+45** | 5.41 ± 0.62 | 6.03 ± 1.11 | 3.51 ± 0.44 |

SEQUENCE LISTING

```
<160> NUMBER OF SEQ ID NOS: 94

<210> SEQ ID NO 1
<211> LENGTH: 26
<212> TYPE: DNA
<213> ORGANISM: Artificial Sequence
<220> FEATURE:
<223> OTHER INFORMATION: Forward primer E-Sarbeco-F1

<400> SEQUENCE: 1

acaggtacgt taatagttaa tagcgt                                          26


<210> SEQ ID NO 2
<211> LENGTH: 22
<212> TYPE: DNA
<213> ORGANISM: Artificial Sequence
<220> FEATURE:
<223> OTHER INFORMATION: reverse primer E-Sarbeco-R2

<400> SEQUENCE: 2

atattgcagc agtacgcaca ca                                              22


<210> SEQ ID NO 3
<211> LENGTH: 26
<212> TYPE: DNA
<213> ORGANISM: Artificial Sequence
<220> FEATURE:
<223> OTHER INFORMATION: probe E-Sarbeco-P1

<400> SEQUENCE: 3

acactagcca tccttactgc gcttcg                                          26


<210> SEQ ID NO 4
<211> LENGTH: 25
<212> TYPE: PRT
<213> ORGANISM: Artificial Sequence
<220> FEATURE:
<223> OTHER INFORMATION: RBD-mAb-1 VH FR1

<400> SEQUENCE: 4

Glu Val Gln Leu Gln Gln Ser Gly Pro Gln Leu Val Arg Pro Gly Ala
1               5                   10                  15

Ser Met Lys Ile Ser Cys Lys Ala Ser
            20                  25


<210> SEQ ID NO 5
<211> LENGTH: 8
<212> TYPE: PRT
<213> ORGANISM: Artificial Sequence
<220> FEATURE:
<223> OTHER INFORMATION: RBD-mAb-1 VH CDR1
```

<400> SEQUENCE: 5

```
Gly Tyr Ser Phe Thr Thr Tyr Trp
1               5
```

<210> SEQ ID NO 6
<211> LENGTH: 17
<212> TYPE: PRT
<213> ORGANISM: Artificial Sequence
<220> FEATURE:
<223> OTHER INFORMATION: RBD-mAb-1 VH FR2

<400> SEQUENCE: 6

```
Met His Trp Val Lys Gln Arg Pro Gly Gln Gly Leu Gln Trp Ile Gly
1               5                   10                  15

Met
```

<210> SEQ ID NO 7
<211> LENGTH: 8
<212> TYPE: PRT
<213> ORGANISM: Artificial Sequence
<220> FEATURE:
<223> OTHER INFORMATION: RBD-mAb-1 VH CDR2

<400> SEQUENCE: 7

```
Ile Asp Pro Ser Asp Ser Glu Thr
1               5
```

<210> SEQ ID NO 8
<211> LENGTH: 38
<212> TYPE: PRT
<213> ORGANISM: Artificial Sequence
<220> FEATURE:
<223> OTHER INFORMATION: RBD-mAb-1 VH FR3

<400> SEQUENCE: 8

```
Arg Leu Asn Gln Lys Phe Lys Asp Lys Ala Thr Leu Thr Val Asp Lys
1               5                   10                  15

Ser Ser Ser Thr Ala Tyr Met Gln Leu Ser Ser Pro Thr Ser Glu Asp
            20                  25                  30

Ser Ala Val Tyr Tyr Cys
        35
```

<210> SEQ ID NO 9
<211> LENGTH: 12
<212> TYPE: PRT
<213> ORGANISM: Artificial Sequence
<220> FEATURE:
<223> OTHER INFORMATION: RBD-mAb-1 VH CDR3

<400> SEQUENCE: 9

```
Ala Arg Asp Phe Asp Tyr Asp Arg Thr Met Asp Tyr
1               5                   10
```

<210> SEQ ID NO 10
<211> LENGTH: 11
<212> TYPE: PRT
<213> ORGANISM: Artificial Sequence
<220> FEATURE:
<223> OTHER INFORMATION: RBD-mAb-1 VH FR4

<400> SEQUENCE: 10

```
Trp Gly Gln Gly Thr Ser Val Thr Val Ser Ser
1               5                   10
```

<210> SEQ ID NO 11
<211> LENGTH: 25
<212> TYPE: PRT
<213> ORGANISM: Artificial Sequence
<220> FEATURE:
<223> OTHER INFORMATION: RBD-mAb-15 VH FR1

<400> SEQUENCE: 11

```
Glu Val Gln Leu Glu Glu Ser Gly Pro Gly Leu Val Gln Pro Ser Gln
1               5                   10                  15

Ser Leu Ser Ile Thr Cys Thr Val Ser
            20                  25
```

<210> SEQ ID NO 12
<211> LENGTH: 8
<212> TYPE: PRT
<213> ORGANISM: Artificial Sequence
<220> FEATURE:
<223> OTHER INFORMATION: RBD-mAb-15 VH CDR1

<400> SEQUENCE: 12

```
Asp Phe Ser Leu Thr Thr Tyr Gly
1               5
```

<210> SEQ ID NO 13
<211> LENGTH: 17
<212> TYPE: PRT
<213> ORGANISM: Artificial Sequence
<220> FEATURE:
<223> OTHER INFORMATION: RBD-mAb-15 VH FR2

<400> SEQUENCE: 13

```
Val His Trp Val Arg Gln Ser Pro Gly Lys Gly Leu Glu Trp Leu Gly
1               5                   10                  15

Val
```

<210> SEQ ID NO 14
<211> LENGTH: 7
<212> TYPE: PRT
<213> ORGANISM: Artificial Sequence
<220> FEATURE:
<223> OTHER INFORMATION: RBD-mAb-15 VH CDR2

<400> SEQUENCE: 14

```
Ile Trp Ser Gly Gly Ser Thr
1               5
```

<210> SEQ ID NO 15
<211> LENGTH: 38
<212> TYPE: PRT
<213> ORGANISM: Artificial Sequence
<220> FEATURE:
<223> OTHER INFORMATION: RBD-mAb-15 VH FR3

<400> SEQUENCE: 15

```
Asp Tyr Asn Ala Ala Phe Ile Ser Arg Leu Ser Ile Ser Lys Asp Asn
1               5                   10                  15

Ser Lys Ser Gln Val Phe Phe Lys Met Asn Ser Leu Gln Thr Asn Asp
            20                  25                  30

Thr Ala Ile Tyr Tyr Cys
        35
```

<210> SEQ ID NO 16
<211> LENGTH: 14

<212> TYPE: PRT
<213> ORGANISM: Artificial Sequence
<220> FEATURE:
<223> OTHER INFORMATION: RBD-mAb-15 VH CDR3

<400> SEQUENCE: 16

Ala Arg Met Gly Asp Gly Tyr Tyr Val Gly Ala Met Asp Tyr
1 5 10

<210> SEQ ID NO 17
<211> LENGTH: 11
<212> TYPE: PRT
<213> ORGANISM: Artificial Sequence
<220> FEATURE:
<223> OTHER INFORMATION: RBD-mAb-15 VH FR4

<400> SEQUENCE: 17

Trp Gly Gln Gly Thr Ser Val Thr Val Ser Ser
1 5 10

<210> SEQ ID NO 18
<211> LENGTH: 25
<212> TYPE: PRT
<213> ORGANISM: Artificial Sequence
<220> FEATURE:
<223> OTHER INFORMATION: RBD-mAb-25 VH FR1

<400> SEQUENCE: 18

Glu Val Gln Leu Glu Glu Ser Gly Gly Gly Leu Val Lys Pro Gly Gly
1 5 10 15

Ser Leu Lys Leu Ser Cys Ala Ala Ser
20 25

<210> SEQ ID NO 19
<211> LENGTH: 8
<212> TYPE: PRT
<213> ORGANISM: Artificial Sequence
<220> FEATURE:
<223> OTHER INFORMATION: RBD-mAb-25 VH CDR1

<400> SEQUENCE: 19

Gly Phe Thr Phe Ser Ser Tyr Thr
1 5

<210> SEQ ID NO 20
<211> LENGTH: 17
<212> TYPE: PRT
<213> ORGANISM: Artificial Sequence
<220> FEATURE:
<223> OTHER INFORMATION: RBD-mAb-25 VH FR2

<400> SEQUENCE: 20

Met Ser Trp Val Arg Gln Ser Pro Glu Lys Arg Leu Glu Trp Val Ala
1 5 10 15

Glu

<210> SEQ ID NO 21
<211> LENGTH: 8
<212> TYPE: PRT
<213> ORGANISM: Artificial Sequence
<220> FEATURE:
<223> OTHER INFORMATION: RBD-mAb-25 VH CDR2

<400> SEQUENCE: 21

Ile Ser Ser Gly Gly Thr Tyr Thr
1 5

<210> SEQ ID NO 22
<211> LENGTH: 38
<212> TYPE: PRT
<213> ORGANISM: Artificial Sequence
<220> FEATURE:
<223> OTHER INFORMATION: RBD-mAb-25 VH FR3

<400> SEQUENCE: 22

Asn Tyr Pro Asp Thr Ala Thr Gly Arg Phe Thr Ile Ser Arg Asp Asn
1 5 10 15

Ala Lys Asn Thr Leu Tyr Leu Glu Met Ser Ser Leu Arg Ser Glu Asp
20 25 30

Thr Ala Met Tyr Tyr Cys
35

<210> SEQ ID NO 23
<211> LENGTH: 11
<212> TYPE: PRT
<213> ORGANISM: Artificial Sequence
<220> FEATURE:
<223> OTHER INFORMATION: RBD-mAb-25 VH CDR3

<400> SEQUENCE: 23

Ala Asn Phe Gly Asn Tyr Glu Glu Ile Ala Tyr
1 5 10

<210> SEQ ID NO 24
<211> LENGTH: 11
<212> TYPE: PRT
<213> ORGANISM: Artificial Sequence
<220> FEATURE:
<223> OTHER INFORMATION: RBD-mAb-25 VH FR4

<400> SEQUENCE: 24

Trp Gly Gln Gly Thr Leu Val Thr Val Ser Ala
1 5 10

<210> SEQ ID NO 25
<211> LENGTH: 25
<212> TYPE: PRT
<213> ORGANISM: Artificial Sequence
<220> FEATURE:
<223> OTHER INFORMATION: RBD-mAb-28 VH FR1

<400> SEQUENCE: 25

Gln Val Gln Leu Gln Gln Pro Gly Thr Glu Leu Val Met Pro Gly Ala
1 5 10 15

Ser Val Lys Met Ser Cys Lys Ala Ser
20 25

<210> SEQ ID NO 26
<211> LENGTH: 8
<212> TYPE: PRT
<213> ORGANISM: Artificial Sequence
<220> FEATURE:
<223> OTHER INFORMATION: RBD-mAb-28 VH CDR1

<400> SEQUENCE: 26

Gly Tyr Thr Phe Thr Asp Tyr Tyr
1 5

<210> SEQ ID NO 27
<211> LENGTH: 17
<212> TYPE: PRT

<213> ORGANISM: Artificial Sequence
<220> FEATURE:
<223> OTHER INFORMATION: RBD-mAb-28 VH FR2

<400> SEQUENCE: 27

Leu His Trp Met Lys Gln Arg Pro Gly Gln Gly Leu Glu Trp Ile Gly
1               5                   10                  15

Ala

<210> SEQ ID NO 28
<211> LENGTH: 8
<212> TYPE: PRT
<213> ORGANISM: Artificial Sequence
<220> FEATURE:
<223> OTHER INFORMATION: RBD-mAb-28 VH CDR2

<400> SEQUENCE: 28

Ile Asp Ser Ser Asp Ser Tyr Thr
1               5

<210> SEQ ID NO 29
<211> LENGTH: 38
<212> TYPE: PRT
<213> ORGANISM: Artificial Sequence
<220> FEATURE:
<223> OTHER INFORMATION: RBD-mAb-28 VH FR3

<400> SEQUENCE: 29

Asp Tyr Asn Gln Asn Phe Lys Gly Lys Ala Thr Leu Thr Val Asp Glu
1               5                   10                  15

Ser Ser Ser Thr Ala Tyr Met His Leu Ser Ser Leu Thr Ser Glu Asp
            20                  25                  30

Ser Ala Val Tyr Tyr Cys
        35

<210> SEQ ID NO 30
<211> LENGTH: 15
<212> TYPE: PRT
<213> ORGANISM: Artificial Sequence
<220> FEATURE:
<223> OTHER INFORMATION: RBD-mAb-28 VH CDR3

<400> SEQUENCE: 30

Ala Arg Gly Lys Asp Ala Tyr Asp Arg Arg Pro Trp Phe Ala Tyr
1               5                   10                  15

<210> SEQ ID NO 31
<211> LENGTH: 11
<212> TYPE: PRT
<213> ORGANISM: Artificial Sequence
<220> FEATURE:
<223> OTHER INFORMATION: RBD-mAb-28 VH FR4

<400> SEQUENCE: 31

Trp Gly Gln Gly Thr Leu Val Thr Val Ser Ala
1               5                   10

<210> SEQ ID NO 32
<211> LENGTH: 25
<212> TYPE: PRT
<213> ORGANISM: Artificial Sequence
<220> FEATURE:
<223> OTHER INFORMATION: RBD-mAb-45 VH FR1

<400> SEQUENCE: 32

Glu Val Gln Leu Gln Gln Ser Gly Pro Glu Leu Val Lys Pro Gly Ala
1               5                   10                  15

Ser Val Lys Ile Ser Cys Lys Thr Ser
            20                  25

<210> SEQ ID NO 33
<211> LENGTH: 8
<212> TYPE: PRT
<213> ORGANISM: Artificial Sequence
<220> FEATURE:
<223> OTHER INFORMATION: RBD-mAb-45 VH CDR1

<400> SEQUENCE: 33

Gly Tyr Thr Phe Thr Glu Tyr Thr
1               5

<210> SEQ ID NO 34
<211> LENGTH: 17
<212> TYPE: PRT
<213> ORGANISM: Artificial Sequence
<220> FEATURE:
<223> OTHER INFORMATION: RBD-mAb-45 VH FR2

<400> SEQUENCE: 34

Ile Tyr Trp Val Lys Gln Ser Leu Gly Lys Ser Leu Glu Trp Ile Gly
1               5                   10                  15

Gly

<210> SEQ ID NO 35
<211> LENGTH: 8
<212> TYPE: PRT
<213> ORGANISM: Artificial Sequence
<220> FEATURE:
<223> OTHER INFORMATION: RBD-mAb-45 VH CDR2

<400> SEQUENCE: 35

Asn Asn Pro Asn Asn Asp Asp Thr
1               5

<210> SEQ ID NO 36
<211> LENGTH: 38
<212> TYPE: PRT
<213> ORGANISM: Artificial Sequence
<220> FEATURE:
<223> OTHER INFORMATION: RBD-mAb-45 VH FR3

<400> SEQUENCE: 36

Thr Tyr Lys Gln Phe Phe Lys Gly Lys Ala Thr Leu Thr Val Asp Lys
1               5                   10                  15

Ser Ser Ser Thr Ala Tyr Met Glu Leu Arg Ser Leu Thr Ser Glu Asp
            20                  25                  30

Ser Ala Val Tyr Tyr Cys
        35

<210> SEQ ID NO 37
<211> LENGTH: 13
<212> TYPE: PRT
<213> ORGANISM: Artificial Sequence
<220> FEATURE:
<223> OTHER INFORMATION: RBD-mAb-45 VH CDR3

<400> SEQUENCE: 37

Ala Arg Asp Gly Tyr Pro Tyr Tyr Tyr Ala Leu Asp Phe
1 5 10

<210> SEQ ID NO 38
<211> LENGTH: 11
<212> TYPE: PRT
<213> ORGANISM: Artificial Sequence
<220> FEATURE:
<223> OTHER INFORMATION: RBD-mAb-45 VH FR4

<400> SEQUENCE: 38

Trp Gly Gln Gly Thr Ser Val Thr Val Ser Ser
1 5 10

<210> SEQ ID NO 39
<211> LENGTH: 25
<212> TYPE: PRT
<213> ORGANISM: Artificial Sequence
<220> FEATURE:
<223> OTHER INFORMATION: RBD-mAb-51 VH FR1

<400> SEQUENCE: 39

Glu Val Gln Leu Gln Gln Ser Gly Pro Glu Leu Val Lys Pro Gly Ala
1 5 10 15

Ser Ala Lys Ile Ser Cys Lys Thr Ser
20 25

<210> SEQ ID NO 40
<211> LENGTH: 8
<212> TYPE: PRT
<213> ORGANISM: Artificial Sequence
<220> FEATURE:
<223> OTHER INFORMATION: RBD-mAb-51 VH CDR1

<400> SEQUENCE: 40

Gly Tyr Thr Phe Thr Glu Tyr Thr
1 5

<210> SEQ ID NO 41
<211> LENGTH: 17
<212> TYPE: PRT
<213> ORGANISM: Artificial Sequence
<220> FEATURE:
<223> OTHER INFORMATION: RBD-mAb-51 VH FR2

<400> SEQUENCE: 41

Met Tyr Trp Val Lys Gln Ser His Gly Lys Ser Leu Glu Trp Ile Gly
1 5 10 15

Gly

<210> SEQ ID NO 42
<211> LENGTH: 8
<212> TYPE: PRT
<213> ORGANISM: Artificial Sequence
<220> FEATURE:
<223> OTHER INFORMATION: RBD-mAb-51 VH CDR2

<400> SEQUENCE: 42

Ile Asn Pro Asn Asn Gly Asp Thr
1 5

<210> SEQ ID NO 43
<211> LENGTH: 38

<212> TYPE: PRT
<213> ORGANISM: Artificial Sequence
<220> FEATURE:
<223> OTHER INFORMATION: RBD-mAb-51 VH FR3

<400> SEQUENCE: 43

```
Thr Tyr Asn Gln Thr Phe Lys Gly Lys Ala Thr Leu Thr Val Asp Lys
1               5                   10                  15

Ser Ser Ser Thr Ala Tyr Met Glu Leu Arg Ser Leu Thr Ser Glu Asp
            20                  25                  30

Ser Ala Val Tyr Tyr Cys
        35
```

<210> SEQ ID NO 44
<211> LENGTH: 13
<212> TYPE: PRT
<213> ORGANISM: Artificial Sequence
<220> FEATURE:
<223> OTHER INFORMATION: RBD-mAb-51 VH CDR3

<400> SEQUENCE: 44

```
Ala Arg Asp Gly Tyr Pro Phe Tyr Tyr Ala Leu Asp Tyr
1               5                   10
```

<210> SEQ ID NO 45
<211> LENGTH: 11
<212> TYPE: PRT
<213> ORGANISM: Artificial Sequence
<220> FEATURE:
<223> OTHER INFORMATION: RBD-mAb-51 VH FR4

<400> SEQUENCE: 45

```
Trp Gly Gln Gly Ile Ser Val Thr Val Ser Ser
1               5                   10
```

<210> SEQ ID NO 46
<211> LENGTH: 26
<212> TYPE: PRT
<213> ORGANISM: Artificial Sequence
<220> FEATURE:
<223> OTHER INFORMATION: RBD-mAb-1 VL FR1

<400> SEQUENCE: 46

```
Asp Ile Val Met Ser Gln Ser Pro Ser Ser Leu Ala Val Ser Val Gly
1               5                   10                  15

Glu Lys Val Thr Met Ser Cys Lys Ser Ser
            20                  25
```

<210> SEQ ID NO 47
<211> LENGTH: 12
<212> TYPE: PRT
<213> ORGANISM: Artificial Sequence
<220> FEATURE:
<223> OTHER INFORMATION: RBD-mAb-1 VL CDR1

<400> SEQUENCE: 47

```
Gln Ser Leu Leu Phe Ser Ser Ser Gln Lys Asn Tyr
1               5                   10
```

<210> SEQ ID NO 48
<211> LENGTH: 17
<212> TYPE: PRT
<213> ORGANISM: Artificial Sequence
<220> FEATURE:
<223> OTHER INFORMATION: RBD-mAb-1 VL FR2

<400> SEQUENCE: 48

Leu Ala Trp Tyr Gln Gln Lys Ala Gly Gln Ser Pro Lys Leu Leu Ile
1 5 10 15

Phe

<210> SEQ ID NO 49
<211> LENGTH: 36
<212> TYPE: PRT
<213> ORGANISM: Artificial Sequence
<220> FEATURE:
<223> OTHER INFORMATION: RBD-mAb-1 VL FR3

<400> SEQUENCE: 49

Thr Arg Glu Ser Gly Val Pro Asp Arg Phe Thr Gly Ser Gly Ser Gly
1 5 10 15

Thr Asp Phe Thr Leu Thr Ile Ser Ser Val Lys Ala Glu Asp Leu Ala
20 25 30

Ile Tyr Tyr Cys
35

<210> SEQ ID NO 50
<211> LENGTH: 9
<212> TYPE: PRT
<213> ORGANISM: Artificial Sequence
<220> FEATURE:
<223> OTHER INFORMATION: RBD-mAb-1 VL CDR3

<400> SEQUENCE: 50

Lys Gln Tyr Tyr Lys Tyr Pro Leu Thr
1 5

<210> SEQ ID NO 51
<211> LENGTH: 10
<212> TYPE: PRT
<213> ORGANISM: Artificial Sequence
<220> FEATURE:
<223> OTHER INFORMATION: RBD-mAb-1 VL FR4

<400> SEQUENCE: 51

Phe Gly Ala Gly Thr Lys Leu Asp Ile Lys
1 5 10

<210> SEQ ID NO 52
<211> LENGTH: 26
<212> TYPE: PRT
<213> ORGANISM: Artificial Sequence
<220> FEATURE:
<223> OTHER INFORMATION: RBD-mAb-15 VL FR1

<400> SEQUENCE: 52

Asp Ile Gln Leu Thr Gln Ser Pro Ala Ile Leu Ser Val Ser Pro Gly
1 5 10 15

Glu Arg Val Ser Phe Ser Cys Arg Ala Ser
20 25

<210> SEQ ID NO 53
<211> LENGTH: 6
<212> TYPE: PRT
<213> ORGANISM: Artificial Sequence
<220> FEATURE:
<223> OTHER INFORMATION: RBD-mAb-15 VL CDR1

<400> SEQUENCE: 53

Gln Ser Ile Gly Thr Ser
1 5

<210> SEQ ID NO 54
<211> LENGTH: 17
<212> TYPE: PRT
<213> ORGANISM: Artificial Sequence
<220> FEATURE:
<223> OTHER INFORMATION: RBD-mAb-15 VL FR2

<400> SEQUENCE: 54

Ile His Trp Tyr Gln Gln Arg Thr Asn Gly Ser Pro Arg His Leu Ile
1 5 10 15

Lys

<210> SEQ ID NO 55
<211> LENGTH: 36
<212> TYPE: PRT
<213> ORGANISM: Artificial Sequence
<220> FEATURE:
<223> OTHER INFORMATION: RBD-mAb-15 VL FR3

<400> SEQUENCE: 55

Glu Ser Ile Ser Gly Ile Pro Ser Arg Phe Ser Gly Ser Gly Ser Gly
1 5 10 15

Thr Asp Phe Thr Leu Thr Ile Asn Gly Val Glu Ser Glu Asp Ile Ala
20 25 30

Asp Tyr Tyr Cys
35

<210> SEQ ID NO 56
<211> LENGTH: 9
<212> TYPE: PRT
<213> ORGANISM: Artificial Sequence
<220> FEATURE:
<223> OTHER INFORMATION: RBD-mAb-15 VL CDR3

<400> SEQUENCE: 56

Gln Gln Gly His Asn Trp Pro Leu Thr
1 5

<210> SEQ ID NO 57
<211> LENGTH: 10
<212> TYPE: PRT
<213> ORGANISM: Artificial Sequence
<220> FEATURE:
<223> OTHER INFORMATION: RBD-mAb-15 VL FR4

<400> SEQUENCE: 57

Phe Gly Ala Gly Thr Lys Leu Asp Ile Lys
1 5 10

<210> SEQ ID NO 58
<211> LENGTH: 26
<212> TYPE: PRT
<213> ORGANISM: Artificial Sequence
<220> FEATURE:
<223> OTHER INFORMATION: RBD-mAb-25 VL FR1

<400> SEQUENCE: 58

Gln Ile Val Leu Thr Gln Ser Pro Ala Ile Met Ser Val Ser Leu Gly
1 5 10 15

Glu Arg Val Thr Met Thr Cys Thr Ala Ser
20 25

<210> SEQ ID NO 59
<211> LENGTH: 7
<212> TYPE: PRT
<213> ORGANISM: Artificial Sequence
<220> FEATURE:
<223> OTHER INFORMATION: RBD-mAb-28 VL CDR1

<400> SEQUENCE: 59

Ser Ser Val Ser Ser Ser Tyr
1 5

<210> SEQ ID NO 60
<211> LENGTH: 17
<212> TYPE: PRT
<213> ORGANISM: Artificial Sequence
<220> FEATURE:
<223> OTHER INFORMATION: RBD-mAb-28 VL FR2

<400> SEQUENCE: 60

Leu His Trp Tyr Gln Gln Lys Pro Gly Ser Ser Pro Lys Leu Trp Ile
1 5 10 15

Tyr

<210> SEQ ID NO 61
<211> LENGTH: 36
<212> TYPE: PRT
<213> ORGANISM: Artificial Sequence
<220> FEATURE:
<223> OTHER INFORMATION: RBD-mAb-28 VL FR3

<400> SEQUENCE: 61

Asn Leu Ala Ser Gly Val Pro Ala Arg Phe Ser Gly Ser Gly Ser Gly
1 5 10 15

Thr Ser Tyr Ser Leu Thr Ile Ser Ser Met Glu Ala Glu Asp Ala Ala
20 25 30

Thr Tyr Tyr Cys
35

<210> SEQ ID NO 62
<211> LENGTH: 9
<212> TYPE: PRT
<213> ORGANISM: Artificial Sequence
<220> FEATURE:
<223> OTHER INFORMATION: RBD-mAb-28 VL CDR3

<400> SEQUENCE: 62

His Gln Tyr His Arg Ser Pro Tyr Thr
1 5

<210> SEQ ID NO 63
<211> LENGTH: 10
<212> TYPE: PRT
<213> ORGANISM: Artificial Sequence
<220> FEATURE:
<223> OTHER INFORMATION: RBD-mAb-28 VL FR4

<400> SEQUENCE: 63

Phe Gly Gly Gly Thr Lys Leu Glu Ile Lys
1 5 10

<210> SEQ ID NO 64
<211> LENGTH: 26

<212> TYPE: PRT
<213> ORGANISM: Artificial Sequence
<220> FEATURE:
<223> OTHER INFORMATION: RBD-mAb-28 VL FR1

<400> SEQUENCE: 64

Asp Ile Gln Met Thr Gln Thr Thr Ser Ser Leu Ser Ala Ser Leu Gly
1 5 10 15

Asp Arg Val Thr Ile Ser Cys Ser Ala Ser
20 25

<210> SEQ ID NO 65
<211> LENGTH: 6
<212> TYPE: PRT
<213> ORGANISM: Artificial Sequence
<220> FEATURE:
<223> OTHER INFORMATION: RBD-mAb-28 VL CDR1

<400> SEQUENCE: 65

Gln Gly Ile Arg Tyr Tyr
1 5

<210> SEQ ID NO 66
<211> LENGTH: 17
<212> TYPE: PRT
<213> ORGANISM: Artificial Sequence
<220> FEATURE:
<223> OTHER INFORMATION: RBD-mAb-28 VL FR2

<400> SEQUENCE: 66

Leu Asn Trp Tyr Gln Gln Lys Pro Asp Gly Thr Val Lys Leu Leu Ile
1 5 10 15

Tyr

<210> SEQ ID NO 67
<211> LENGTH: 36
<212> TYPE: PRT
<213> ORGANISM: Artificial Sequence
<220> FEATURE:
<223> OTHER INFORMATION: RBD-mAb-28 VL FR3

<400> SEQUENCE: 67

Asn Leu His Ser Gly Val Pro Ser Arg Phe Ser Gly Ser Gly Ser Gly
1 5 10 15

Thr Asp Tyr Ser Leu Thr Ile Ser Asn Leu Glu Pro Glu Asp Ile Ala
20 25 30

Thr Tyr Tyr Cys
35

<210> SEQ ID NO 68
<211> LENGTH: 9
<212> TYPE: PRT
<213> ORGANISM: Artificial Sequence
<220> FEATURE:
<223> OTHER INFORMATION: RBD-mAb-28 VL CDR3

<400> SEQUENCE: 68

Gln Gln Tyr Asn Lys Leu Pro Tyr Thr
1 5

<210> SEQ ID NO 69
<211> LENGTH: 10
<212> TYPE: PRT
<213> ORGANISM: Artificial Sequence
<220> FEATURE:

<223> OTHER INFORMATION: RBD-mAb-28 VL FR4

<400> SEQUENCE: 69

Phe Gly Gly Gly Thr Lys Leu Asp Ile Lys
1 5 10

<210> SEQ ID NO 70
<211> LENGTH: 26
<212> TYPE: PRT
<213> ORGANISM: Artificial Sequence
<220> FEATURE:
<223> OTHER INFORMATION: RBD-mAb-45 VL FR1

<400> SEQUENCE: 70

Asp Ile Leu Met Thr Gln Ser Gln Lys Phe Met Ser Thr Ser Val Gly
1 5 10 15

Asp Arg Val Ser Val Thr Cys Lys Ser Ser
20 25

<210> SEQ ID NO 71
<211> LENGTH: 6
<212> TYPE: PRT
<213> ORGANISM: Artificial Sequence
<220> FEATURE:
<223> OTHER INFORMATION: RBD-mAb-45 VL CDR1

<400> SEQUENCE: 71

Gln Asn Val Gly Thr Asn
1 5

<210> SEQ ID NO 72
<211> LENGTH: 17
<212> TYPE: PRT
<213> ORGANISM: Artificial Sequence
<220> FEATURE:
<223> OTHER INFORMATION: RBD-mAb-45 VL FR2

<400> SEQUENCE: 72

Val Ala Trp Tyr Gln Gln Lys Pro Gly Gln Ser Pro Lys Ala Leu Ile
1 5 10 15

Tyr

<210> SEQ ID NO 73
<211> LENGTH: 36
<212> TYPE: PRT
<213> ORGANISM: Artificial Sequence
<220> FEATURE:
<223> OTHER INFORMATION: RBD-mAb-45 VL FR3

<400> SEQUENCE: 73

Tyr Arg Tyr Ser Gly Val Pro Asp His Phe Thr Gly Ser Gly Ser Gly
1 5 10 15

Thr Asp Phe Thr Leu Thr Ile Ser Asn Val Gln Ser Ala Asp Leu Ala
20 25 30

Glu Tyr Phe Cys
35

<210> SEQ ID NO 74
<211> LENGTH: 9
<212> TYPE: PRT
<213> ORGANISM: Artificial Sequence
<220> FEATURE:
<223> OTHER INFORMATION: RBD-mAb-45 VL CDR3

<400> SEQUENCE: 74

Gln Gln Tyr Asn Asn Tyr Pro Trp Thr
1 5

<210> SEQ ID NO 75
<211> LENGTH: 10
<212> TYPE: PRT
<213> ORGANISM: Artificial Sequence
<220> FEATURE:
<223> OTHER INFORMATION: RBD-mAb-45 VL FR4

<400> SEQUENCE: 75

Phe Gly Gly Gly Thr Lys Leu Asp Ile Lys
1 5 10

<210> SEQ ID NO 76
<211> LENGTH: 26
<212> TYPE: PRT
<213> ORGANISM: Artificial Sequence
<220> FEATURE:
<223> OTHER INFORMATION: RBD-mAb-51 VL FR1

<400> SEQUENCE: 76

Asp Ile Val Met Thr Gln Ser Gln Lys Phe Met Ser Thr Ser Val Gly
1 5 10 15

Asp Arg Val Ser Val Thr Cys Lys Ala Arg
20 25

<210> SEQ ID NO 77
<211> LENGTH: 6
<212> TYPE: PRT
<213> ORGANISM: Artificial Sequence
<220> FEATURE:
<223> OTHER INFORMATION: RBD-mAb-51 VL CDR1

<400> SEQUENCE: 77

Gln Ile Val Gly Thr Asn
1 5

<210> SEQ ID NO 78
<211> LENGTH: 17
<212> TYPE: PRT
<213> ORGANISM: Artificial Sequence
<220> FEATURE:
<223> OTHER INFORMATION: RBD-mAb-51 VL FR2

<400> SEQUENCE: 78

Val Ala Trp Tyr Gln Gln Lys Pro Gly Gln Ser Pro Lys Ala Leu Ile
1 5 10 15

Tyr

<210> SEQ ID NO 79
<211> LENGTH: 36
<212> TYPE: PRT
<213> ORGANISM: Artificial Sequence
<220> FEATURE:
<223> OTHER INFORMATION: RBD-mAb-51 VL FR3

<400> SEQUENCE: 79

Tyr Arg Tyr Ser Gly Val Pro Asp Arg Phe Thr Gly Ser Gly Ser Gly
1 5 10 15

Thr Asp Phe Thr Leu Thr Ile Thr Asn Val His Ser Glu Asp Leu Ala
20 25 30

```
Glu Phe Phe Cys
        35


<210> SEQ ID NO 80
<211> LENGTH: 9
<212> TYPE: PRT
<213> ORGANISM: Artificial Sequence
<220> FEATURE:
<223> OTHER INFORMATION: RBD-mAb-51 VL CDR3

<400> SEQUENCE: 80

His Gln Tyr Asn Ser Tyr Pro Trp Thr
1               5


<210> SEQ ID NO 81
<211> LENGTH: 10
<212> TYPE: PRT
<213> ORGANISM: Artificial Sequence
<220> FEATURE:
<223> OTHER INFORMATION: RBD-mAb-51 VL FR4

<400> SEQUENCE: 81

Phe Gly Gly Gly Thr Lys Leu Asp Ile Lys
1               5                   10


<210> SEQ ID NO 82
<211> LENGTH: 120
<212> TYPE: PRT
<213> ORGANISM: Artificial Sequence
<220> FEATURE:
<223> OTHER INFORMATION: RBD-mAb-45 VH

<400> SEQUENCE: 82

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Ile Tyr Trp Val Lys Gln Ser Leu Gly Lys Ser Leu Glu Trp Ile
        35                  40                  45

Gly Gly Asn Asn Pro Asn Asn Asp Asp Thr Thr Tyr Lys Gln Phe Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Asp Gly Tyr Pro Tyr Tyr Tyr Ala Leu Asp Phe Trp Gly Gln
            100                 105                 110

Gly Thr Ser Val Thr Val Ser Ser
        115                 120


<210> SEQ ID NO 83
<211> LENGTH: 107
<212> TYPE: PRT
<213> ORGANISM: Artificial Sequence
<220> FEATURE:
<223> OTHER INFORMATION: RBD-mAb-45 VL

<400> SEQUENCE: 83

Asp Ile Leu Met Thr Gln Ser Gln Lys Phe Met Ser Thr Ser Val Gly
1               5                   10                  15

Asp Arg Val Ser Val Thr Cys Lys Ser Ser Gln Asn Val Gly Thr Asn
            20                  25                  30
```

```
Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp His Phe Thr Gly
    50                  55                  60

Ser Gly Ser Gly Thr Asp Phe Thr Leu Thr Ile Ser Asn Val Gln Ser
65                  70                  75                  80

Ala Asp Leu Ala Glu Tyr Phe Cys Gln Gln Tyr Asn Asn Tyr Pro Trp
                85                  90                  95

Thr Phe Gly Gly Gly Thr Lys Leu Asp Ile Lys
            100                 105


<210> SEQ ID NO 84
<211> LENGTH: 122
<212> TYPE: PRT
<213> ORGANISM: Artificial Sequence
<220> FEATURE:
<223> OTHER INFORMATION: RBD-mAb-28 VH

<400> SEQUENCE: 84

Gln Val Gln Leu Gln Gln Pro Gly Thr Glu Leu Val Met Pro Gly Ala
1               5                   10                  15

Ser Val Lys Met Ser Cys Lys Ala Ser Gly Tyr Thr Phe Thr Asp Tyr
            20                  25                  30

Tyr Leu His Trp Met Lys Gln Arg Pro Gly Gln Gly Leu Glu Trp Ile
        35                  40                  45

Gly Ala Ile Asp Ser Ser Asp Ser Tyr Thr Asp Tyr Asn Gln Asn Phe
    50                  55                  60

Lys Gly Lys Ala Thr Leu Thr Val Asp Glu Ser Ser Ser Thr Ala Tyr
65                  70                  75                  80

Met His Leu Ser Ser Leu Thr Ser Glu Asp Ser Ala Val Tyr Tyr Cys
                85                  90                  95

Ala Arg Gly Lys Asp Ala Tyr Asp Arg Arg Pro Trp Phe Ala Tyr Trp
            100                 105                 110

Gly Gln Gly Thr Leu Val Thr Val Ser Ala
        115                 120


<210> SEQ ID NO 85
<211> LENGTH: 107
<212> TYPE: PRT
<213> ORGANISM: Artificial Sequence
<220> FEATURE:
<223> OTHER INFORMATION: RBD-mAb-28 VL

<400> SEQUENCE: 85

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Arg Tyr Tyr
            20                  25                  30

Leu Asn Trp Tyr Gln Gln Lys Pro Asp Gly Thr Val Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Asn Lys Leu Pro Tyr
                85                  90                  95

Thr Phe Gly Gly Gly Thr Lys Leu Asp Ile Lys
            100                 105
```

<210> SEQ ID NO 86
<211> LENGTH: 120
<212> TYPE: PRT
<213> ORGANISM: Artificial Sequence
<220> FEATURE:
<223> OTHER INFORMATION: RBD-mAb-15 VH

<400> SEQUENCE: 86

```
Glu Val Gln Leu Glu Glu Ser Gly Pro Gly Leu Val Gln Pro Ser Gln
1               5                   10                  15

Ser Leu Ser Ile Thr Cys Thr Val Ser Asp Phe Ser Leu Thr Thr Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Thr Asn Asp Thr Ala Ile Tyr Tyr Cys Ala
                85                  90                  95

Arg Met Gly Asp Gly Tyr Tyr Val Gly Ala Met Asp Tyr Trp Gly Gln
            100                 105                 110

Gly Thr Ser Val Thr Val Ser Ser
        115                 120
```

<210> SEQ ID NO 87
<211> LENGTH: 107
<212> TYPE: PRT
<213> ORGANISM: Artificial Sequence
<220> FEATURE:
<223> OTHER INFORMATION: RBD-mAb-15 VL

<400> SEQUENCE: 87

```
Asp Ile Gln Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg His Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Asn Gly Val Glu Ser
65                  70                  75                  80

Glu Asp Ile Ala Asp Tyr Tyr Cys Gln Gln Gly His Asn Trp Pro Leu
                85                  90                  95

Thr Phe Gly Ala Gly Thr Lys Leu Asp Ile Lys
            100                 105
```

<210> SEQ ID NO 88
<211> LENGTH: 118
<212> TYPE: PRT
<213> ORGANISM: Artificial Sequence
<220> FEATURE:
<223> OTHER INFORMATION: RBD-mAb-25 VH

<400> SEQUENCE: 88

```
Glu Val Gln Leu Glu Glu Ser Gly Gly Gly Leu Val Lys Pro Gly Gly
1               5                   10                  15
```

```
Ser Leu Lys Leu Ser Cys Ala Ala Ser Gly Phe Thr Phe Ser Ser Tyr
            20                  25                  30

Thr Met Ser Trp Val Arg Gln Ser Pro Glu Lys Arg Leu Glu Trp Val
        35                  40                  45

Ala Glu Ile Ser Ser Gly Gly Thr Tyr Thr Asn Tyr Pro Asp Thr Ala
    50                  55                  60

Thr Gly Arg Phe Thr Ile Ser Arg Asp Asn Ala Lys Asn Thr Leu Tyr
65                  70                  75                  80

Leu Glu Met Ser Ser Leu Arg Ser Glu Asp Thr Ala Met Tyr Tyr Cys
                85                  90                  95

Ala Asn Phe Gly Asn Tyr Glu Glu Ile Ala Tyr Trp Gly Gln Gly Thr
            100                 105                 110

Leu Val Thr Val Ser Ala
        115


<210> SEQ ID NO 89
<211> LENGTH: 108
<212> TYPE: PRT
<213> ORGANISM: Artificial Sequence
<220> FEATURE:
<223> OTHER INFORMATION: RBD-mAb-25 VL

<400> SEQUENCE: 89

Gln Ile Val Leu Thr Gln Ser Pro Ala Ile Met Ser Val Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Tyr Thr Phe Gly Gly Gly Thr Lys Leu Glu Ile Lys
            100                 105


<210> SEQ ID NO 90
<211> LENGTH: 120
<212> TYPE: PRT
<213> ORGANISM: Artificial Sequence
<220> FEATURE:
<223> OTHER INFORMATION: RBD-mAb-51 VH

<400> SEQUENCE: 90

Glu Val Gln Leu Gln Gln Ser Gly Pro Glu Leu Val Lys Pro Gly Ala
1               5                   10                  15

Ser Ala Lys Ile Ser Cys Lys Thr Ser Gly Tyr Thr Phe Thr Glu Tyr
            20                  25                  30

Thr Met Tyr Trp Val Lys Gln Ser His Gly Lys Ser Leu Glu Trp Ile
        35                  40                  45

Gly Gly Ile Asn Pro Asn Asn Gly Asp Thr Thr Tyr Asn Gln Thr Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95
```

Ala Arg Asp Gly Tyr Pro Phe Tyr Tyr Ala Leu Asp Tyr Trp Gly Gln
100 105 110

Gly Ile Ser Val Thr Val Ser Ser
115 120

<210> SEQ ID NO 91
<211> LENGTH: 107
<212> TYPE: PRT
<213> ORGANISM: Artificial Sequence
<220> FEATURE:
<223> OTHER INFORMATION: RBD-mAb-51 VL

<400> SEQUENCE: 91

Asp Ile Val Met Thr Gln Ser Gln Lys Phe Met Ser Thr Ser Val Gly
1 5 10 15

Asp Arg Val Ser Val Thr Cys Lys Ala Arg Gln Ile Val Gly Thr Asn
20 25 30

Val Ala Trp Tyr Gln Gln Lys Pro Gly Gln Ser Pro Lys Ala Leu Ile
35 40 45

Tyr Ser Ala Ser Tyr Arg Tyr Ser Gly Val Pro Asp Arg Phe Thr Gly
50 55 60

Ser Gly Ser Gly Thr Asp Phe Thr Leu Thr Ile Thr Asn Val His Ser
65 70 75 80

Glu Asp Leu Ala Glu Phe Phe Cys His Gln Tyr Asn Ser Tyr Pro Trp
85 90 95

Thr Phe Gly Gly Gly Thr Lys Leu Asp Ile Lys
100 105

<210> SEQ ID NO 92
<211> LENGTH: 119
<212> TYPE: PRT
<213> ORGANISM: Artificial Sequence
<220> FEATURE:
<223> OTHER INFORMATION: RBD-mAb-1 VH

<400> SEQUENCE: 92

Glu Val Gln Leu Gln Gln Ser Gly Pro Gln Leu Val Arg Pro Gly Ala
1 5 10 15

Ser Met Lys Ile Ser Cys Lys Ala Ser Gly Tyr Ser Phe Thr Thr Tyr
20 25 30

Trp Met His Trp Val Lys Gln Arg Pro Gly Gln Gly Leu Gln Trp Ile
35 40 45

Gly Met Ile Asp Pro Ser Asp Ser Glu Thr Arg Leu Asn Gln Lys Phe
50 55 60

Lys Asp Lys Ala Thr Leu Thr Val Asp Lys Ser Ser Ser Thr Ala Tyr
65 70 75 80

Met Gln Leu Ser Ser Pro Thr Ser Glu Asp Ser Ala Val Tyr Tyr Cys
85 90 95

Ala Arg Asp Phe Asp Tyr Asp Arg Thr Met Asp Tyr Trp Gly Gln Gly
100 105 110

Thr Ser Val Thr Val Ser Ser
115

<210> SEQ ID NO 93
<211> LENGTH: 113
<212> TYPE: PRT
<213> ORGANISM: Artificial Sequence
<220> FEATURE:
<223> OTHER INFORMATION: RBD-mAb-1 VL

<400> SEQUENCE: 93

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Phe Ser
            20                  25                  30

Ser Ser Gln Lys Asn Tyr Leu Ala Trp Tyr Gln Gln Lys Ala Gly Gln
        35                  40                  45

Ser Pro Lys Leu Leu Ile Phe Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Ile Tyr Tyr Cys Lys Gln
                85                  90                  95

Tyr Tyr Lys Tyr Pro Leu Thr Phe Gly Ala Gly Thr Lys Leu Asp Ile
            100                 105                 110

Lys
```

<210> SEQ ID NO 94
<211> LENGTH: 223
<212> TYPE: PRT
<213> ORGANISM: Artificial Sequence
<220> FEATURE:
<223> OTHER INFORMATION: SARS-CoV-2 S RBD

<400> SEQUENCE: 94

```
Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220
```

POTENT NEUTRALIZING ANTIBODIES FOR PREVENTION AND TREATMENT OF COVID-19

REFERENCE TO RELATED APPLICATION

This application is a national stage application (under 35 U.S.C. 371) of PCT/US2021/052650 filed 29 Sep. 2021, which claims priority to U.S. provisional applications 63/086,206 filed on 1 Oct. 2020 and 63/167,109 filed on 28 Mar. 2021, all of which are herein incorporated by reference in their entireties.

FIELD OF THE INVENTION

The present invention relates generally to SARS-COV-2 neutralizing antibody and antibody cocktail.

BACKGROUND OF THE INVENTION

Severe acute respiratory syndrome coronavirus 2 (SARS-COV-2) is responsible for the coronavirus disease 2019 (COVID-19) pandemic, with more than 205 million people infected and 4.32 million dead as of August 2021. SARS-COV-2 infection is initiated by the engagement of the spike(S) protein receptor-binding domain (RBD) to the host receptor molecule, angiotensin-converting enzyme 2 (ACE2). This binding triggers subsequent conformational changes within the S protein that enable viral entry. Most neutralizing antibodies (nAbs) therefore target the RBD to compete with ACE2 and prevent viral entry.

To optimize the efficacy of antibody treatment, it may be desirable to develop cocktails of neutralizing Abs that can simultaneously bind different sites of the RBD and synergistically neutralize SARS-COV-2. As the emergence of variant lineages is a major challenge preventing effective control of the COVID-19 pandemic, next-generation vaccines and therapeutic Abs must target variant epitopes, especially those with a high possibility to alter transmission or infectivity. With regard to the efficacies of antibody therapies or vaccines, it will be crucial to understand the implications of antigenic variation on agents for clinical use.

SUMMARY OF THE INVENTION

In one aspect, the invention provides a human chimeric antibody (RBD-chAb), specifically against SARS-COV-2 Spike(S) receptor-binding domain (RBD), which is referred to as RBD-chAb-45, the RBD-chAb-45 comprising a heavy chain variable region ($V_H$) and a light chain variable region ($V_L$), wherein:

(i) the $V_L$ comprises the amino acid sequence of SEQ ID NO: 82; and (ii) the $V_L$ comprises the amino acid sequence of SEQ ID NO: 83.

In another aspect, the invention provides a human chimeric antibody (RBD-chAb) cocktail, specifically against SARS-COV-2 S RBD, comprising:

(i) a human chimeric antibody (RBD-chAb) referred to as RBD-chAb-45 as defined above; and (ii) one or more additional human chimeric antibodies (RBD-chAbs), specifically against SARS-COV-2 S RBD, which is selected from the group consisting of: (1) RBD-chAb-28; (2) RBD-chAb-15; (3) RBD-chAb-25; (4) RBD-chAb-51; (5) RBD-chAb-1; and (6) any combination thereof;

wherein the RBD-chAb-28, -15, -25, -51 and -1 each comprise a $V_H$ and a $V_L$ as defined below:

(1) the RBD-chAb-28 (-28):

(i) the $V_H$ comprises the amino acid sequence of SEQ ID NO: 84; and (ii) the $V_L$ comprises the amino acid sequence of SEQ ID NO: 85;

(2) RBD-chAb-15 (-15):

(i) the $V_H$ comprises the amino acid sequence of SEQ ID NO: 86; and (ii) the $V_L$ comprises the amino acid sequence of SEQ ID NO: 87;

(3) RBD-chAb-25 (-25):

(i) the $V_H$ comprises the amino acid sequence of SEQ ID NO: 88; and (ii) the $V_L$ comprises the amino acid sequence of SEQ ID NO: 89;

(4) RBD-chAb-51 (-51):

(i) the $V_H$ comprises the amino acid sequence of SEQ ID NO: 90; and (ii) the $V_L$ comprises the amino acid sequence of SEQ ID NO: 91;

(5) RBD-chAb-1 (-1):

(i) the $V_H$ comprises the amino acid sequence of SEQ ID NO: 92; and (ii) the $V_L$ comprises the amino acid sequence of SEQ ID NO: 93.

In one embodiment, the RBD-chAb cocktail of the invention comprises at least two RBD-chAbs selected from the group consisting of: (1) RBD-chAb-45 and -25; (2) RBD-chAb-45 and -15; and (3) RBD-chAb-45 and -28.

Further in another aspect, the invention provides a human chimeric antibody (RBD-chAb), specifically against SARS-COV-2 S RBD protein, the RBD-chAb being selected from the group consisting of:

(1) RBD-chAb-45 (-45); (2) RBD-chAb-28 (-28); (3) RBD-chAb-15 (-15); (4) RBD-chAb-25 (~25); (5) RBD-chAb-51 (-51); and (6) RBD-chAb-1 (-1), wherein the RBD-chAb-45, -28, -15, -25, -51 and -1 each comprise a $V_H$ and a $V_L$ as defined above.

The invention further provides a human chimeric antibody (RBD-chAb) cocktail, specifically against SARS-COV-2 S RBD protein, comprising more than one of the RBD-chAb of the invention.

In one embodiment, the RBD-chAb cocktail of the invention comprises two RBD-chAbs selected from the group consisting of: (1) RBD-chAb-45 and -25; (2) RBD-chAb-45 and -15; (3) RBD-chAb-45 and -28; (4) RBD-chAb-51 and -15; and (5) RBD-chAb-51 and -28.

Further in another aspect, the invention provides a human chimeric antibody (RBD-chAb) cocktail comprising at least two human chimeric antibodies (RBD-chAbs), specifically against SARS-COV-2 S RBD protein, the at least two RBD-chAbs being any combination of RBD-chAbs selected from the group consisting of: (1) RBD-chAb-45 (-45); (2) RBD-chAb-28 (-28); (3) RBD-chAb-15 (-15): (4) RBD-chAb-25 (-25); (5) RBD-chAb-51 (-51); and (6) RBD-chAb-1 (-1), wherein the RBD-chAb-45, -28, -15, -25, -51 and -1 each comprise a $V_H$ and a $V_L$ as defined in claim 2.

In one embodiment, the at least two RBD-chAbs are selected from the group consisting of: (1) RBD-chAb-45 and -25; (2) RBD-chAb-45 and -15; (3) RBD-chAb-45 and -28; (4) RBD-chAb-51 and -15; (5) RBD-chAb-51 and -28; (6) RBD-chAb-25, -28, and -45; and (7) RBD-chAb-25, -28, and -51.

The RBD-chAb-45, -28, -15, -25, -51 and -1 each comprise a $V_H$ and a $V_L$, the $V_H$ comprising $V_H$ CDR1, $V_H$ CDR2, and $V_K$ CDR3, and the $V_L$ comprising $V_L$ CDR1, $V_L$ CDR2, and $V_L$ CDR3, as defined below:

(1) the RBD-chAb-45 (-45);

(a) the $V_H$ CDR1, $V_H$ CDR2, and $V_H$ CDR3 comprise the amino acid sequence of SEQ ID NO: 33, SEQ ID NO: 35, and SEQ ID NO: 37, respectively; and (b) the $V_L$ CDR1, $V_L$ CDR2, and $V_L$ CDR3 comprise the amino acid sequence of SEQ ID NO: 71, Ser Ala Ser (SAS), and SEQ ID NO: 74, respectively;

(2) the RBD-mAb-28 (-28):

(a) the $V_H$ CDR1, $V_H$ CDR2, and Var CDR3 comprise the amino acid sequence of SEQ ID NO: 26, SEQ ID NO: 28, and SEQ ID NO: 30, respectively; and (b) the $V_L$ CDR1, $V_L$ CDR2, and $V_L$ CDR3 comprise the amino acid sequence of SEQ ID NO: 65, Tyr Thr Ser (YTS), and SEQ ID NO: 68, respectively;

(3) RBD-mAb-15 (~15):

(a) the $V_H$ CDR1, $V_H$ CDR2, and $V_H$ CDR3 comprise the amino acid sequence of SEQ ID NO: 12, SEQ ID NO: 14, and SEQ ID NO: 16, respectively; and (b) the $V_L$ CDR1, $V_L$ CDR2, and $V_L$ CDR3 comprise the amino acid sequence of SEQ ID NO: 53, Tyr Ala Ser (YAS), and SEQ ID NO: 56, respectively;

(3) RBD-mAb-25 (-25):

(a) the $V_H$ CDR1, $V_H$ CDR2, and $V_H$ CDR3 comprise the amino acid sequence of SEQ ID NO: 19, SEQ ID NO: 21, and SEQ ID NO: 23, respectively; and (b) the $V_L$ CDR1, $V_L$ CDR2, and $V_L$ CDR3 comprise the amino acid sequence of SEQ ID NO: 59, Ser Thr Ser (STS), and SEQ ID NO: 62, respectively;

(4) RBD-mAb-51 (-51):

(a) the $V_H$ CDR1, $V_H$ CDR2, and $V_H$ CDR3 comprise the amino acid sequence of SEQ ID NO: 40, SEQ ID NO: 42, and SEQ ID NO: 44, respectively; and (b) the $V_L$ CDR1, $V_L$ CDR2, and $V_L$ CDR3 comprise the amino acid sequence of SEQ ID NO: 77, Ser Ala Ser (SAS), and SEQ ID NO: 80, respectively; and (5) RBD-mAb-1 (-1):

(a) the $V_H$ CDR1, $V_H$ CDR2, and $V_K$ CDR3 comprise the amino acid sequence of SEQ ID NO: 5, SEQ ID NO: 7, and SEQ ID NO: 9, respectively; and (b) the $V_L$ CDR1, $V_L$ CDR2, and Vt, CDR3 comprise the amino acid sequence of SEQ ID NO: 47, Trp Ala Ser (WAS), and SEQ ID NO: 50, respectively.

Further in another aspect, the invention provides a neutralizing antibody or an antigen-binding fragment thereof, specifically against SARS-Cov2 spike (S)-protein receptor-binding domain (RBD), being selected from the group consisting of: (1) RBD-mAb-45 (-45); (2) RBD-mAb-28 (-28); (3) RBD-mAb-15 (-15); (4) RBD-mAb-25 (-25); (5) RBD-mAb-51 (-51); and (6) RBD-mAb-1 (-1), wherein the RBD-mAb-45, ~28, -15, -25, -51 and -1 each comprise a $V_H$ domain and a $V_L$ domain as defined below:

(1) RBD-mAb-45 (-45);

(i) the $V_H$ comprises the amino acid sequence of SEQ ID NO: 82; and (ii) the $V_L$ comprises the amino acid sequence of SEQ ID NO: 83;

(2) the RBD-mAb-28 (-28):

(i) the $V_H$ comprises the amino acid sequence of SEQ ID NO: 84; and (ii) the $V_L$ comprises the amino acid sequence of SEQ ID NO: 85;

(3) the RBD-mAb-15 (-15);

(i) the Var comprises the amino acid sequence of SEQ ID NO: 86; and (ii) the $V_L$ comprises the amino acid sequence of SEQ ID NO: 87;

(4) the RBD-mAb-25 (-25):

(i) the $V_H$ comprises the amino acid sequence of SEQ ID NO: 88; and (ii) the $V_L$ comprises the amino acid sequence of SEQ ID NO: 89;

(5) the RBD-mAb-51 (-51);

(i) the $V_H$ comprises the amino acid sequence of SEQ ID NO: 90; and (ii) the $V_L$ comprises the amino acid sequence of SEQ ID NO: 91;

(6) the RBD-mAb-1 (-1):

(i) the $V_H$ comprises the amino acid sequence of SEQ ID NO: 92; and (ii) the $V_L$ comprises the amino acid sequence of SEQ ID NO: 93.

In one embodiment, the neutralizing antibody or antigen-binding fragment thereof of the invention is a human chimeric antibody (RBD-chAb), specifically against SARS-Cov2 S RBD, being selected from the group consisting of: (1) RBD-chAb-45 (-45); (2) RBD-chAb-28 (-28); (3) RBD-chAb-15 (-15); (4) RBD-chAb-25 (-25); (5) RBD-chAb-51 (-51); and (6) RBD-chAb-1 (-1), wherein the RBD-chAb-45, -28, -15, -25, -51 and -1 each comprise a $V_H$ and a $V_L$ as defined above.

In another embodiment, the neutralizing antibody or the antigen-binding fragment thereof of the invention is a single-chain variable fragment, a Fab fragment, or a Fv fragment.

Further in another aspect, the invention provides a vaccine composition, comprising a human chimeric antibody (RBD-chAb) of the invention, or a human chimeric antibody (RBD-chAb) cocktail of the invention.

The vaccine composition of the invention may further comprise a buffered saline or a pharmaceutically acceptable carrier or vehicle, or an adjuvant, or any combination thereof.

Yet in another aspect, the invention provides use of a human chimeric antibody (RBD-chAb) of the invention, or a RBD-chAb cocktail of the invention, or a vaccine composition of the invention, in the manufacture of a medicament for protection and/or treatment of COVID-19 in a subject in need thereof.

In another embodiment, the neutralizing antibody or antigen-binding fragment thereof of the invention comprises $V_H$ and $V_L$ domains, wherein the $V_H$ and $V_L$ domains are grafted onto a human IgG1 and kappa backbone and form a human chimeric antibody (RBD-chAb).

In one embodiment, the vaccine composition comprises a RBD-chAb cocktail that comprises RBD-chAbs selected from the group consisting of: (1) RBD-chAb-25 and -45; (2) RBD-chAb-25, -28, and -45; (3) RBD-chAb-25, -28, and -51; and (4) RBD-chAb-15 and -45.

The invention further provides use of a human chimeric antibody (RBD-chAb), or a human chimeric antibody (RBD-chAb) cocktail of the invention in the manufacture of a medicament for protection against COVID-19 infection or for minimizing infection in lung in a subject in need thereof.

In one embodiment of the use of the antibody cocktail, the cocktail comprises RBD-chAbs selected from the group consisting of: (1) RBD-chAb-25 and -45; (2) RBD-chAb-15 and -45; (3) RBD-chAb-45, -25, and -28; and (4) RBD-chAb-25, -28, and -51.

In one embodiment of the use of RBD-chAb, the RBD-chAb is selected from the group consisting of RBD-chAb-45, -25, -28 and -51.

A method for protection and/or treatment of COVID-19, comprising: administering to a subject in need thereof a therapeutically effective amount of a RBD-chAb, a RBD-chAb cocktail, or a vaccine composition of the invention for protection and/or treatment of the COVID-19 in the subject in need thereof.

A method for protection against COVID-19 infection or minimizing infection in lung in a subject in need thereof, comprising: administering to the subject in need thereof a therapeutically effective amount of a RBD-chAb, or a RBD-chAb cocktail of the invention for protection against COVID-19 infection or minimizing infection in the lung in the subject in need thereof.

In one embodiment, the COVID-19 is a variant selected from the group consisting of United Kingdom variant B.1.1.7 (Alpha), South African variant B.1.351 (Beta), Brazil variant P1 (Gamma), California variant B.1.429 (Epsilon), New York variant B.1.526 (Iota), Indian variant B.1.617.1 (Kappa) and B.1.617.2 (Delta).

The invention also provides use of a RBD-chAb for neutralizing, preventing, protecting and/or treating COVID-19 in a subject in need thereof, wherein the RBD-chAb is selected from the group consisting of (1) RBD-chAb-45; (2) RBD-chAb-51; (3) RBD-chAb-1 (4) RBD-chAb-15; (5) RBD-chAb-28, and (6) RBD-chAb-25; and further wherein the COVID-19 is a variant selected from the group consisting of United Kingdom variant B. 1.1.7 (Alpha), South African variant B.1,351 (Beta), Brazil variant P1 (Gamma), California variant B.1.429 (Epsilon), New York variant B. 1.526 (Iota) and Indian variants B.1.617.1 (Kappa) and B.1.617.2 (Delta).

BRIEF DESCRIPTION OF THE DRAWINGS

FIG. 1 shows identification of SARS-COV-2-neutralizing chAbs. (A) Neutralization potency measured with a pseudotyped virus neutralization assay. Data for each chAb are from a representative neutralization experiment. Each assay was performed in triplicate and data points represent the mean (n=3). (B) Neutralizing chAbs inhibiting SARS-COV-2 infection were assessed by PRNT. ChAbs were serially diluted in PBS and used to block infection of Vero E6 cells with SARS-COV-2. Virus without chAb served as a control. Plaques formed at each dilution were counted 4 days after virus infection. n=3. (C) The kinetics of chAb binding to SARS-COV-2 RBD. $K_D$, affinity constant calculated using 1:1 binding model. $k_a$, association constant; $k_d$, dissociation constant.

FIGS. 13A-B show amino acid sequences of $V_H$ and $V_L$ domains of anti-RBD mAbs.

DETAILED DESCRIPTION OF THE INVENTION

Definitions

Figure 2:
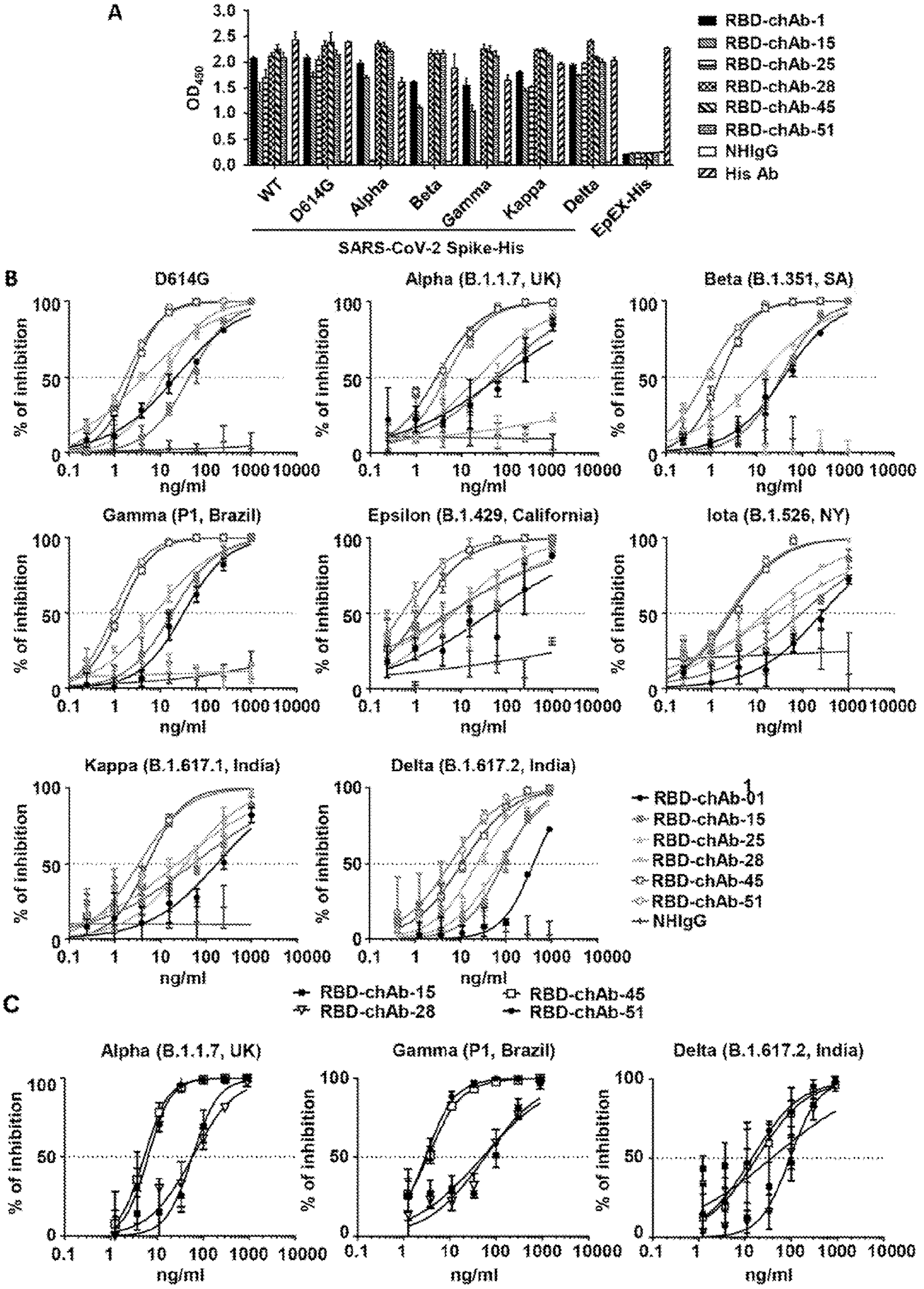
FIG. 2 shows single chAbs binding and neutralizing capacities toward SARS-COV-2 variants. (A) The binding of anti-RBD chAbs to S-His protein of SARS-COV-2 variants was probed by ELISA. n=3. (B) Neutralization assay of SARS-COV-2 variant pseudoviruses with RBD-chAbs. n=3. (C) Neutralizing RBD-chAbs inhibit SARS-COV-2 variants, Alpha, Gamma and Delta; infection was assessed by PRNT. n=3.

Unless otherwise defined, all technical and scientific terms used herein have the same meaning as commonly understood by one of ordinary skill in the art to which this invention pertains. In the case of conflict, the present document, including definitions will control.

The term "treating", or "treatment" refers to administration of an effective amount of the compound to a subject in need thereof with the purpose of cure, alleviate, relieve, remedy, or ameliorate the disease, the symptoms of it, or the predisposition towards it. Such a subject can be identified by a health care professional based on results from any suitable diagnostic method.

"An effective amount" refers to the amount that is required to confer a therapeutic effect on the treated subject. Effective doses will vary, as recognized by those skilled in the art, depending on rout of administration, excipient usage, and the possibility of co-usage with other therapeutic treatment.

The "Guidance for Industry and Reviewers Estimating the Safe Starting Dose in Clinical Trials for Therapeutics in Adult Healthy Volunteers" published by the U.S. Department of Health and Human Services Food and Drug Administration discloses a "therapeutically effective amount" may be obtained by calculations from the following formula:

$$\text{HED}=\text{animal dose in mg/kg}\times(\text{animal weight in kg/human weight in kg})^{0.33}.$$

Abbreviations: COVID-19, Coronavirus disease 2019; SARS-COV-2, severe acute respiratory syndrome coronavirus 2; RBD, receptor-binding domain; RBM, receptor binding motif; RBD-chAbs, chimeric anti-RBD antibodies; chAbs, chimeric antibodies; VOCs, variants of concern; RT, room temperature; BSA, bovine serum albumin; TMB, 3,3'5,5-Tetramethylbenzidine; CDR8, complementarity-determining regions; dNTP, deoxy-ribonucleoside triphosphate; IP, intraperitoneal; LOD, limit of detection; i.n., intranasal; SEC, size-exclusion chromatography; TCID, tissue culture infectious dose; TCID50, median TCID or 50% TCID; $TCID_{50}$/ml, TCID50 per ml; $OD_{450}$, optical density at 450 nm; PRNT, plaque reduction neutralization test; FAM, Fluorescein amidite; BBQ, blackberry quencher; PFU, plaque-forming units.

SEQUENCE LISTING $V_H$: The amino acid sequences of the $V_H$ domain of RBD-chAb-45, -28, -15, -25, -51, and -1 are SEQ ID NO: 82, 84, 86, 88, 90, 92, respectively. Vi.: The amino acid sequences of the $V_L$ domain of RBD-chAb-45, -28, -15, -25, -51, and -1 are SEQ ID NO: 83, 85, 87, 89, 91, 93, respectively. The amino acid sequences of CDR1, CDR2, CDR3 of Var and $V_L$ domains of each RBD-chAb are listed in FIGS. 13A-B, respectively.

SARS-COV-2 S RBD: SEQ ID NO: 94 (Nature volume 581, pages 215-220 (2020).

Utilities and Advantages of the Invention

The current supply of therapeutic antibodies for COVID-19 is insufficient to fill the enormous demand, and escape mutants may compromise the utility of existing drugs. Thus, there is an urgent worldwide need to develop highly potent neutralizing antibody cocktails. The invention provides novel therapeutic antibodies for the prevention and treatment of COVID-19. A cocktail of therapeutic chAbs that target three separate epitopes on the RBM of SARS-COV-2 spike protein may increase therapeutic efficacy and decrease the potential for virus escape mutants, serving to benefit a wide range of COVID-19 patients. Thus, the potent neutralizing antibody cocktail has strong potential for development as an effective therapeutic drug to prevent and treat SARS-COV-2 infection.

Materials and Methods

Animals

Mice and hamsters were housed individually in cages on a 12-hr light/dark cycle at 20-24° C. and given free access to food and water. To minimize suffering, animals were euthanized upon loss of over 20% body weight or when the animal exhibited hunching, lack of movement, ruffled fur, and poor grooming. The mice were killed by CO2 asphyxiation. The average body weight of animals is as follows: Balb/cJ mice (antigen immunized mice, 4-6 weeks old female): 16.1~19.1 g. C57BL/6J mice (AAV/ACE2 mice, 8-10 weeks old female): 19.6-20.7 g. Hamster (SARS-COV-2 infection model, females): 102-128 g. Syrian hamster (8 weeks old, female): 114.2 g.

Binding of Antibodies Against SARS-COV-2 by ELISA

The ELISA plates were coated with 0.5 g/ml RBD-His, S-His, or EpEX-His protein in 0.1 M $NaHCO_3$ (pH 8.6)

buffer at 4° C. overnight, followed by blocking with PBS containing 1% BSA at RT for 2 h. After blocking, the wells were washed twice with PBS; the plates were then stored at −20° C.

The protein contents of the culture supernatants from hybridoma or antibodies were quantified by the BCA assay and serially diluted with 1% BSA in PBS. Fifty µl supernatant or antibody was added into each well, and the plate was incubated for 1 h at RT. The plates were washed with PBS containing 0.1% TWEEN®-20 ($PBST_{0.1}$) three times and incubated for 1 h with Peroxidase AffiniPure Goat Anti-mouse IgG or Peroxidase AffiniPure Goat Anti-human IgG (1:5000 dilution). After three washes with $PBST_{0.1}$, signal was produced using TMB color development. The reaction was stopped with 3 N HCl, and absorbance measured at 450 nm by ELISA reader.

Histological Analysis

Viral antigen detection in SARS-COV-2 animal models was accomplished by immunofluorescence staining. The lung was fixed with 4% paraformaldehyde, paraffin embedded and cut into 3-µm sections. Slides were deparaffinized and rehydrated, then incubated with PBS/0.02% TRITON™ X-100 and blocked with 5% BSA at RT for 1 h. The anti-SARS-COV-2 N protein antibody was added to the sections, followed by washing and incubation with ALEXA FLUOR® 568 goat-anti-human IgG at 1:200 dilution. After washing in PBS, slides were stained with DAPI at 1:100 dilution. The images were acquired using a ZEN 2011 Black Edition and LSM 700 confocal microscopy.

Cloning and Sequencing of Neutralizing mAbs

Total RNA was extracted from hybridoma cells using PURELINK™ RNA Mini Kit. Purified RNA was reverse transcribed by SUPERSCRIPT™ III using oligo (dT) as a primer. The variable heavy- and light-chain domains ($V_H$ and $V_L$) were amplified from the cDNA product by PCR with various primer sets. PCR products were cloned using the TA kit, and the subcloned $V_H$ and Vi sequences were determined by DNA sequencing. The framework regions (FRs) and complementarity-determining regions (CDRs) were analyzed with the ImMunoGeneTics database.

Construction and Expression of Chimeric Antibodies (chAbs)

The $V_H$ and $V_K$ gene segments of mAbs were introduced via appropriate restriction enzyme sites and amplified by PCR with KAPA HiFi DNA polymerase. The $V_H$ genes were cloned separately in-frame into a modified expression vector with a signal peptide and human IgG1 constant region. The $V_L$ genes were also separately cloned into a modified expression vector with a signal peptide and human kappa chain constant region. The $V_H$- and $V_L$-encoding plasmids were co-transfected into EXPI293™ cells, which were cultured for 5 days to produce antibody. The culture supernatant from the transfected cells was filtered through a 0.45-µm membrane and then subjected to protein G column chromatography for purification of human IgG. After the dialysis of eluents with PBS, the antibody concentration was assessed using the Bradford assay.

Pseudovirus Neutralization Assay

The pseudovirus neutralization assays were performed using HEK293T cells that stably expressed human ACE2 (HEK293T/hACE2); SARS-COV-2 pseudotyped lentivirus expressing full-length S protein of different variants was provided by the National RNAi Core Facility (Taiwan). HEK293T/hACE2 cells were seeded into 96-well plate at $1\times10^4$ cells per well, and cultivated for 16 h at 37° C. Serial dilutions of RBD-chAbs were pre-incubated with 1000 TU SARS-COV-2 pseudovirus in a 96-well microtiter plate for 1 h at 37° C., and then, the mixtures were added to pre-seeded HEK293T/hACE2 cells for 24 h at 37° C. The pseudovirus-containing culture medium was removed and replaced with 50 µl/well DMEM for an additional 48-h incubation. Fifty µl ONE-GLO™ luciferase reagent was added to each well for 3-min incubation at 37° C. The luminescence was measured with a microplate spectrophotometer. Inhibitions of 0% or 100% were respectively calculated based on pseudovirus only and cells only. The half maximal inhibitory concentration ($IC_{50}$) was calculated by nonlinear regression using Prism software version 8.1.0. The average $IC_{50}$ value for each antibody was determined from at least two independent experiments.

Plaque Reduction Neutralization Test (PRNT)

RBD-chAbs were serially diluted in PBS and pre-incubated with 100 PFU SARS-COV-2 for 1 h at 37° C. The mixtures were added to pre-seeded Vero E6 cells for 1 h at 37° C.'. The viral-containing culture medium was removed and replaced with DMEM containing 2% FBS and 1% methyl-cellulose for an additional 4-day incubation. The cells were fixed with 10% formaldehyde overnight and stained with 0.5% crystal violet for 20 min. The plates were then washed with tap water, and plaque numbers formed at each dilution were counted. Virus without RBD-chAb served as a control. Plaque reduction was calculated as: Inhibition percentage=: 100×[1−(plaque number incubated with mAb/plaque number without mAb)]. The 50% plaque reduction ($PRNT_{50}$) value was calculated with Prism software. The SARS-COV-2 used in this study, the clinical isolate TCDC #4 (hCoV-19/Taiwan/4/2020), Alpha variant (hCoV-19/Taiwan/792/2020), Gamma variant (hCoV-19/Taiwan/906/2021) and Delta variant (hCoV-19/Taiwan/1144/2021), were obtained from Taiwan Centers of Disease Control (CDC). The PRNT assay was performed (n=3) at the BSL-3 facility.

Equilibrium Dissociation Constant ($K_D$) of SARS-COV-2-RBD Binding to chAbs

Binding kinetic measurements were performed using a Biacore 8K. All assays were performed with a running buffer of PBS pH 7.4 supplemented with 0.005% (v/v) Surfactant P20 at 25° C. Anti-RBD chimeric antibodies were immobilized onto a protein A sensor chip surface to a level of ~180 response units (RUS). SARS-COV-2 RBD-His protein was injected in a two-fold dilution series from 40 µM to 0.625 nM, at a flow rate of 50 µl/min using a Multi-cycle kinetics program with an association time of 150 sec and a dissociation time of 300 sec. Running buffer was also injected using the same program for background subtraction. $K_D$ values (affinity constant or dissociation equilibrium constant) were calculated from all the binding curves based on their global fit to a 1:1 binding model by Biacore 8K data analysis software.

Site-Directed Mutagenesis of ACE2-Binding Residues within the RBD

The residues K417, Y453, Q474, F486, Q498, T500, and N501 within the RBD of S protein are responsible for interaction with ACE2. Each ACE2-binding residue was individually replaced with alanine by site-directed mutagenesis using KAPA HiFi Polymerase and Dpul digestion. RBD mutants were constructed with a single mutation at each ACE2-binding residue or multiple mutations if the residues were neighbors. All mutant constructs were confirmed by sequencing.

Epitope Mapping by ELISA

RBD-chAbs were biotin-labeled using EZ-LINK™ Sulfo-NHS-Le-Biotin and purified using an Amicon Ultra-0.5 Centrifugal Filter Unit. Each RBD-chAb (50 ng/well)

was pre-coated to ELISA plates, RBD-His or EpEx-His protein (5 ng/well) in BSA was added to capture Ab-pre-coated ELISA plates, followed by the addition of RBD-chAb (7.8 ng/well) in BSA. Then plates were added biotinylated antibodies (0.78 ng/well) in BSA and incubated at 25° C. for 1 h, and 50 μl of 2000-fold diluted Peroxidase Streptavidin was added into each well and incubated for 1 h at 25° C. The BSA without biotinylated antibodies was as a control. The plates were washed with PBST between each step. After a final wash, the plates were developed with TMB, and absorbance was read at 450 nm after the reaction was stopped.

Prophylactic and Therapeutic Assays for SARS-COV-2 Infection

To assess the in vivo potency of neutralizing chAbs against SARS-COV-2 RBD, mouse and hamster models of SARS-COV-2 infection were utilized. AAV-hACE2 mice were prepared by intratracheal injection of AAV6 expressing hACE2 and IP injection of AAV9 expressing hACE2. The AAV-hACE2-transduced mice or hamsters were first given an IP injection of antibody or normal mouse IgG. Intranasal inoculations of 105 tissue-culture infectious dose (TCID) SARS-COV-2 WT strain (hCoV-19/Taiwan/4/2020) were administered to mice or 103 plaque-forming units (PFU) were administered hamsters 24 h later. Five days or 3 days after the virus challenge to mice or hamsters, lung tissues were harvested to quantify the viral load. Lung tissues were weighed and homogenized using the SpeedMill PLUS for two rounds of 2 min each in 0.6 ml of DMEM with 1% penicillin/streptomycin or RLT buffer. Homogenates were centrifuged at 3,000 rpm for 5 min at 4° C. The supernatant was collected and stored at −80° C. for $TCID_{50}$ assay or RNA extraction. After tissue homogenization, serial 10-fold dilutions of each sample were inoculated in a Vero-E6 cell monolayer in quadruplicate and cultured in DMEM with 1% FBS and penicillin/streptomycin. The plates were observed for cytopathic effects for 4 days. $TCID_{50}$ was interpreted as the amount of virus that caused cytopathic effects in 50% of inoculated wells. Virus titers are expressed as $TCID_{50}$/ml tissue.

The in vivo assays to assess therapeutic activities of chAbs cocktails were conducted by IP injecting mixtures of RBD-chAb-25 and -45. AAV-hACE2 mice or hamsters were i.n. infected with $1\times10^5$ $TCID_{50}$ virus. Antibodies were IP injected into mice or hamsters at day 2 after SARS-Cov-2 inoculation. The mice or hamsters were sacrificed to collect tissue and blood samples at day 5 or 3 post-infection, respectively. The SARS-COV-2 strains are clinical isolates of WT strain (hCoV-19/Taiwan/4/2020) and Delta variant (hCoV-19/Taiwan/1144/2021) obtained from Taiwan CDC.

In Vivo Prophylactic Assays for Low Dose of Neutralizing mAbs Against SARS-COV-2 Infection To assess the in vivo potency of low dose neutralizing mAbs against SARS-CoV-2 RBD, hamster models of SARS-COV-2 infection were utilized. The hamsters were first given an IP injection of antibody or normal mouse IgG. Intranasal inoculations of $10^5$ TCID SARS-COV-2 WT strain (hCoV-19/Taiwan/4/2020) were administered to mice or $10^5$ PFU were administered hamsters 3 or 5 days later. Three days after the virus challenge to mice or hamsters, lung tissues were harvested to quantify the viral load. Lung tissues were weighed and homogenized using the SpeedMill PLUS for two rounds of 2 min each in 0.6 ml of DMEM with 1% penicillin/streptomycin or RLT buffer. Homogenates were centrifuged at 3,000 rpm for 5 min at 4° C. The supernatant was collected and stored at −80° C. for $TCID_{50}$ assay or RNA extraction. After tissue homogenization, serial 10-fold dilutions of each sample were inoculated in a Vero-E6 cell monolayer in quadruplicate and cultured in DMEM with 1% FBS and penicillin/streptomycin. The plates were observed for cytopathic effects for 4 days. $TCID_{50}$ was interpreted as the amount of virus that caused cytopathic effects in 50% of inoculated wells. Virus titers are expressed as $TCID_{50}$/ml tissue.

Real-Time RT-PCR for SARS-COV-2 RNA Quantification

To quantitate SARS-COV-2 RNA, primers targeting the envelope (E) gene of SARS-COV-2 genome were used for TAQMAN™ real-time RT-PCR method. Forward primer E-Sarbeco-FI (5'-ACAGGTACGTTAATAGTTAATAGCGT-3'; SEQ ID NO: 1), reverse primer E-Sarbeco-R2 (S'-ATATTGCAGCAGTACGCACACA-3'; SEQ ID NO: 2), and the probe E-Sarbeco-P1 (5'-FAM-ACACTAGCCATCCTTACTGCGCTTCG-BBQ-3*; SEQ ID NO: 3) were used. RNA solution was collected by using RNeasy Mini Kit. The RNA sample (5 μl) was added in a total 25 μl mixture using SUPERSCRIPT™ III one-step RT-PCR system with PLATINUM™ Taq Polymerase. The final reaction mix contained 400 nM forward and reverse primers, 200 nM probe, 1.6 mM of deoxy-ribonucleoside triphosphate (dNTP), 4 mM magnesium sulphate, 50 nM ROX reference dye and 1 μl of enzyme mixture from the kit. A one-step PCR was performed: 55° C., 10 min for cDNA synthesis, followed by 3 min at 94° C., and 45 amplification cycles at 94° C. for 15 sec and 58° C. for 30 sec. Data were collected and calculated with the APPLIED BIOSYSTEMS™ 7500 Real-Time PCR System. A synthetic 113-bp oligonucleotide fragment was used as a qPCR standard to estimate copy numbers of viral genome.

Cryo-EM Sample Preparation and Data Collection

To prepare S-mAb complexes, purified recombinant SARS-COV-2 $S_{fm2P}$ was mixed individually with RBD-chAb-45, chAb-25, and chAb-15 at a molar ratio of 1:1.4 at RT for 1 h. The mixture was loaded into a size-exclusion column (SUPEROSE® 6 increase 10/300 GL) to separate the S-mAb complex from free mAbs. Fractions corresponding to the S-mAb complex were confirmed by SDS-PAGE and concentrated to 1 mg/ml for cryo-grid preparation. To collect the ternary complex of S protein in complex with RBD-chAb-25 and -45, the SEC fractions corresponding to the ternary complex were collected and concentrated to 1 mg/ml for cryo-grid preparation. Three microliters of each sample were applied onto 300-mesh QUANTIFOIL® R1.2/1.3 holey carbon grids. The grids were glow-charged at 20 mA for 30 sec. After 30-see incubation, the grids were blotted for 2.5 sec at 4° C. and 100% humidity and vitrified using a VITROBOT™ Mark IV.

Cryo-EM data acquisition was performed on a 300 keV TITAN KRIOS™ transmission electron microscope equipped with a Gatan K3® direct detector in a super-resolution mode using the EPU software (THERMOFISHER SCIENTIFIC™). Movies were collected with a defocus range of −1.2 to −1.7 μm at a magnification of 81000×, which results in a pixel size of 0.55 Å. A total of 48-50 e−/Å2 was distributed over 50 frames with an exposure time of 1.8 sec. The datasets were energy-filtered with a slit width of 15-30 eV, and the dose rates were adjusted to 8-10 e-/pix/sec.

Cryo-EM Data Processing

All 2× binned super-resolution raw movies of each S-chAb complex were subject to Relion-3.0 with dose-weighting and 5×5 patch-based alignment using GPU-based software MOTIONCOR2. After motion correction, the corrected micrographs were transferred to cryoSPARC v2.14. Contrast transfer function (CTF) estimation was performed by patch-based CTF. The exposures with "CTF fit to_Res" parameters between 2.5 and 4 Å were selected and applied to particle picking. A small subset of micrographs was used for template-free blob picker, followed by iterative rounds of 2D classification for filtering junk particles. The best 2D classes were then used as templates for particle picking on the remaining micrographs. The picked particles were cleaned and re-extracted with a box size of 384 pixels.

For each S-mAb complex, the particle images were initially classified by ab-initio reconstruction with CI symmetry (class=3). The particles and three ab-initio models were used in heterogeneous refinement to generate three distinct classes (class=3). For both RBD-chAb-25 and -45, the majority of classes corresponded to an all-open state for all three RBDs. Particles within the best class were used for further processing by using non-uniform 3D refinement imposed with CI symmetry. The overall resolution of the EM map was estimated by the gold-standard Fourier shell correlation (FSC)=0.143. To improve the resolution at the mAb binding interface of S-chAb-25 and S-chAb-45 complexes, a focused refinement procedure was employed. For S-chAb-25, a further local refinement with a focus mask covering the NTD, RBD and chAb-25 was performed in eryoSPARC. For S-chAb-45, the particles of NU-refinement were symmetrically expanded by C3 symmetry, then converted to Relion-3.0 using the pyem script (developed by Daniel Asamow). A further focus classification with a focus mask corresponding to the RBD and chAb-45 was implemented in Relion. The particles of the best 3D class were selected and transferred to cryoSPARC for another round of local refinement with same focus mask. Focused masks were generated by a combination of UCSF-Chimera, cryoSPARC and Relion. Local resolution analysis was calculated using ResMap. For the ternary complex of S-chAb-25 and -45, the curated particle images were analyzed by 3D variability analysis within cryoSPARC to identify the subclass of structures with the most abundant chAb-25 EM density on the RBD in addition to the well-defined chAb-45 density on each of the three RBDs.

Model Building and Refinement

The atomic model of SARS-COV-2 S protein in complex with RBD-chAb-25 and -45 were built using Phenix and Coot software. An initial coordinate was generated by using the PDB entry 6XLU as a template in SWISS-MODEL. The atomic models of the Fabs of RBD-chAb-25 and -45 were generated by SWISS-MODEL using default settings. The atomic coordinates of the S protein and the Fabs of RBD-chAb-25 and -45 were manually fit into the cryoEM map using UCSF-Chimera, UCSF-ChimeraX and Coot. After iterative manual refinement steps, the coordinates were refined by the real-space refinement module within Phenix. N-linked glycans were built by using the extension module "Glyco" within Coot from the asparagine side chains at which additional EM densities were observed. These asparagine residues comply with the rule of the N-glycosylation sequon (N-X-S/T). The final model was assessed by MolProbity in Coot. For the ternary complex of S-chAb-25 and -45, the refined atomic models of S-chAb-25 and S-chAb-45 were individually fit to the eryo-EM map of the ternary complex. Manual fitting of the substructure of Fab in complex with the RBD was carried out within UCSF-ChimeraX, followed by application of the automated volume fitting function within UCSF-ChimeraX. Additional manual adjustments of the Fab of RBD-chAb-45 were carried out by visual inspection to optimize rigid body docking, Structural visualization and representations were accomplished by a combination of UCSF-Chimera, UCSF-ChimeraX, and Pymol.

Size-Exclusion Chromatography Analysis of S+RBD-chAb Complex Formation

RBD-chAb binding to the SARS-COV-2 S protein was analyzed by using a gel filtration column (SUPEROSE® 6 increase 10/300 GL) in 50 mM Tris-HCl (pH 8.0), 150 mM NaCl, 0.02% $NaN_3$ at RT. RBD-chAb-25 or -45 was mixed with the SARS-Cov-2 S protein (1 mg/ml) at a 1.4:1 molar ratio and incubated at RT for 1 h prior to injection into an FPLC system (AKTA UPC10) for size-exclusion chromatography (SEC). Fractions that correspond to the binary complex of the S protein and RBD-chAb-25 or -45 were collected, pooled and concentrated using a 50-ml centrifugal concentrator with a 50-kDa molecular weight cutoff before addition of the complementary RBD-chAb-45 or -25 followed by 1 h incubation at RT to allow formation of a ternary complex. The mixture was analyzed by the same SEC analysis to confirm stable complex formation. The ternary complex formed by incubation of S protein and RBD-chAb-25 followed by addition of RBD-chAb-45 was collected as elution fractions (10-12 ml total elution volume) and concentrated by the same procedure used for cryo-EM grid preparation.

Immunohistochemical Analysis of RBD-chAb Reactivity to Normal Human Tissues

To determine appropriate concentrations for the use of mAbs for IHC, immunocytochemistry of RBD protein expressed in human 293T cells was optimized. The recombinant RBD expression vector was transfected into 293T cells by POLYJET™ (SignaGen) in 96-well plates. At 48 h post-transfection, the cells were fixed with 4% paraformaldehyde 30 min. The fixed cells or multi-normal human tissue array (FDA999w) sections were incubated with an anti-SARS-Cov-2 RBD mAb for 1 h at RT, which was detected using the SUPER SENSITIVE™ IHC Detection System. After 3,3'-Diaminobenzidine (DAB) chromogen staining, the specimens were counterstained with hematoxylin. Images were acquired with a Leica DM6000 microscope.

Results

Generation and Characterization of Anti-SARS-Cov-2 RBD chAbs

Six monoclonal antibodies (mAbs) were identified using hybridoma screening. To improve the clinical applicability of these mAbs, these SARS-COV-2 S RBD-specific mAbs were engineered into human IgG1 chimeric antibodies (chAbs). The $V_H$ and $V_L$ domains of the neutralizing mAbs from hybridoma cell lines were identified and grafted onto a human IgG1 and kappa backbone to generate 6 chAb clones. The six RBD-chAbs, namely RBD-chAb-1, -15, -25, -28, -45, and -51 showed $PRNT_{50}$ values of less than 36 ng/ml (FIG. 1B). These six chAbs were highly specific to SARS-COV-2 S protein. None were found to cross-react with the S proteins of the other six human CoVs, namely SARS-COV, MERS-COV, hCoV-OC43, hCoV-HKU1, hCoV-NL63, and hCoV-229E, with the sole exception of RBD-chAb-15, which exhibited partial cross-reactivity to the SI domain of SARS-COV S protein. Additional assessments of antibody specificity (lack of cross-reactivity with whole organs) were performed by staining the FDA human normal organ tissue array. The appropriate amounts of antibodies required for immunocytochemistry staining were assessed using RBD-expressing 293T cells as a reference. All six chAbs showed clear binding to RBD-expressing cells at 1 μg/ml (Table A). We then used a higher concentration of 5 μg/ml to examine the cross-reactivity of each chAb with a multi-normal tissue array. No tissue cross-reactivity was observed for six major target organs (lungs, liver, spleen, heart, kidney, and larynx) for any of the tested chAbs. Further analyses with 27 other human organs, including the cerebrum, cerebellum, adrenal gland, ovary, pancreas, parathyroid gland, hypophysis, testis, thyroid gland, breast, tonsil, thymus, bone marrow, cardiac muscle, esophagus, stomach, small intestine, colon, salivary gland, prostate, endometrium, uterine cervix, skeletal muscle, skin, peripheral nerve, mesothelium, and retina, also did not show cross-reactivity for any of the chAbs (Table A). Table A presents Immunohistochemical staining evaluation of RBD-expression human 293T cell and human organ/tissue.

TABLE A

| Human organ/tissue | RBD-mab-1 | RBD-mab-15 | RBD-mab-25 | RBD-mab-28 | RBD-mab-45 | RBD-mab-51 |
|---|---|---|---|---|---|---|
| RBD-expression human 293T cells | + | + | + | + | + | + |
| Lung | – | – | – | – | – | – |
| Liver | – | – | – | – | – | – |
| Spleen | – | – | – | – | – | – |
| Heart | – | – | – | – | – | – |
| Kidney | – | – | – | – | – | – |
| Larynx | – | – | – | – | – | – |
| Cerebrum | – | – | – | – | – | – |
| Cerebellum | – | – | – | – | – | – |
| Adrenal gland | – | – | – | – | – | – |
| Ovary | – | – | – | – | – | – |
| Pancreas | – | – | – | – | – | – |
| Parathyroid gland | – | – | – | – | – | – |
| Hypophysis | – | – | – | – | – | – |
| Testis | – | – | – | – | – | – |
| Thyroid gland | – | – | – | – | – | – |
| Breast | – | – | – | – | – | – |
| Tonsil | – | – | – | – | – | – |
| Thymus | – | – | – | – | – | – |
| Bone marrow | – | – | – | – | – | – |
| Cardiac muscle | – | – | – | – | – | – |
| Esophagus | – | – | – | – | – | – |
| Stomach | – | – | – | – | – | – |
| Small intestine | – | – | – | – | – | – |
| Colon | – | – | – | – | – | – |
| Salivary gland | – | – | – | – | – | – |
| Prostate | – | – | – | – | – | – |
| Endometrium | – | – | – | – | – | – |
| Uterine cervix | – | – | – | – | – | – |
| Skeletal muscle | – | – | – | – | – | – |
| Skin | – | – | – | – | – | – |
| Peripheral nerve | – | – | – | – | – | – |
| Mesothelium | – | – | – | – | – | – |
| Retina | – | – | – | – | – | – |

+, positive staining;
–, negative staining

Neutralizing Abilities of Anti-RBD chAbs

According to the pseudovirus neutralization assay, RBD-chAb-28, -45 and -51 exhibited very low $IC_{50}$ values of 8.75, 2.30, and 0.98 ng/ml, respectively (FIG. 1A). The PRNT showed that all six RBD-chAbs potently neutralized authentic SARS-COV-2 infection of Vero E6 cells. RBD-chAb-28, -45, and -51 showed the most potent neutralization activities, with $PRNT_{50}$ values of 10.44, 9.90, and 6.47 ng/ml, respectively (FIG. 1B). According to surface plasmon resonance measurements, the dissociation constants ($K_D$) of the six chAbs ranged between 64.3 pM and 6.33 nM (FIG. 1C). The Ko values of RBD-chAb-28, -45, and -51 were less than 500 pM. In light of the global dominance of the D614G variant, we tested the neutralization activity against a pseudovirus of the SARS-Cov-2 D614G mutant and showed that the six chimeric antibodies retained high neutralizing activities, especially RBD-chAb-25, 45, and -51 (FIG. 1B).

Binding and Neutralizing Abilities of Anti-RBD chAbs Against SARS-COV-2 Variants VOCs contain common mutations, such as K417N/T, L452R, E484K/Q, T478K in their RBD domains. We used ELISA to examine the binding ability of our RBD-chAbs to recombinant S protein of SARS-COV-2 variants. The results showed that most of the RBD-chAbs maintained binding ability to S protein from SARS-COV-2 variants; the only exception was RBD-chAb-25 (FIG. 2A). In line with the antibody recognition sites identified, only the binding of RBD-chAb-25 was significantly diminished when tested against the S proteins of Alpha, Beta, and Gamma variants containing the N501Y mutation. This result suggested that besides RBD-chAb-25, most of our neutralizing Abs might retain activity against these VOCs. We further examined the neutralizing abilities of our six most potent RBD-chAbs toward several SARS-COV-2 variant pseudoviruses. Pseudovirus neutralization assays revealed that RBD-chAb-25 exhibited poor neutralizing abilities for the United Kingdom variant B.1.1.7 (Alpha), South African variant B. 1.351 (Beta) and Brazil variant P1 (Gamma), all of which contain the N501Y mutation (FIG. 2B). The rest of the RBD-chAbs retained their abilities to neutralize several common variants, including the United Kingdom variant B.1.1.7 (Alpha), South African variant B.1.351 (Beta), Brazil variant P1 (Gamma), California variant B.1.429 (Epsilon), New York variant B.1.526 (Iota) and India variant B.1.617.1 (Kappa) and B.1.617.2 (Delta) (FIG. 2B). RBD-chAb-45 and -51 exhibited lower $IC_{50}$ values and better neutralizing activities than the other four RBD-chAbs for all variants (Table B).

We evaluated the neutralization potentials of the RBD-chAbs by conducting the in vitro PRNT, RBD-chAb-45 and -51 could effectively block infection with authentic SARS-COV-2 Alpha, Gamma, and Delta variants, with $PRNT_{50}$ values of less than 18 ng/ml; RBD-chAb-15 and -28 were worse at neutralizing the authentic SARS-COV-2 Alpha, Gamma and Delta variants, with $PRNT_{50}$ values ranging from 50 to 94 ng/ml (FIG. 2C and Table C).

Tables B-1 and -2 present half-maximal inhibitory concentrations ($IC_{50}$) values for single RBD-chAbs against pseudovirus of SARS-COV-2 variants.

TABLE B-1

| | SARS-CoV2 pseudovirus $IC_{50}$ (ng/ml) | | | |
|---|---|---|---|---|
| | D614G | B.1.1.7 (UK, Alpha) | B.1.351 (SA, Beta) | P1 (Brazil, Gamma) |
| RBD-chAb-1 | 24.35 ± 5.55 | 33.46 ± 17.9 | 46.71 ± 10.98 | 17.09 ± 7.72 |
| RBD-chAb-15 | 21.25 ± 11.13 | 39.73 ± 16.66 | 30.13 ± 12.03 | 7.18 ± 5.46 |
| RBD-chAb-25 | 9.92 ± 2.04 | Non-N | Non-N | Non-N |
| RBD-chAb-28 | 9.55 ± 4.16 | 11.29 ± 5.93 | 16.52 ± 6.03 | 4.18 ± 1.80 |
| RBD-chAb-45 | 1.58 ± 0.54 | 2.06 ± 0.58 | 2.68 ± 0.84 | 0.76 ± 0.14 |
| RBD-chAb-51 | 1.30 ± 0.27 | 3.07 ± 0.72 | 1.26 ± 0.58 | 0.70 ± 0.19 |

TABLE B-2

| | SARS-CoV-2 pseudovirus $IC_{50}$ (ng/ml) | | | |
|---|---|---|---|---|
| | B.1.429 (California, Epsilon) | B.1.526 (NY, Iota) | B.1.617.1 (India, Kappa) | B.1.617.2 (India, Delta) |
| RBD-chAb-1 | 21.6 ± 11.13 | 428.2 ± 166.3 | 117.7 ± 55.64 | 429.3 ± 36.55 |
| RBD-chAb-15 | 11.72 ± 5.40 | 87.89 ± 5.09 | 67.71 ± 15.84 | 103.6 ± 16.57 |
| RBD-chAb-25 | 6.51 ± 0.73 | 91.95 ± 66.85 | 42.27 ± 7.27 | 35.5 ± 12.14 |
| RBD-chAb-28 | 3.28 ± 1.71 | 44.07 ± 29.58 | 60.62 ± 37.4 | 94.13 ± 22.07 |
| RBD-chAb-45 | 0.91 ± 0.16 | 4.23 ± 1.51 | 5.95 ± 0.72 | 15.51 ± 4.58 |
| RBD-chAb-51 | 1.32 ± 0.75 | 2.28 ± 0.08 | 4.55 ± 1.2 | 8.04 ± 2.11 |

Data are from three independent experiments and are shown as mean ± SEM. Non-N: Non-neutralizing.

Table C presents the 50% plaque reduction ($PRNT_{50}$) value for single RBD-chAbs against Alpha, Gamma, and Delta variants of SARS-COV-2.

TABLE C

| | $PRNT_{50}$ (ng/ml) | | |
|---|---|---|---|
| | B.1.1.7 (UK, Alpha) | P1 (Brazil, Gamma) | B.1.617.2 (India, Delta) |
| RBD-chAb-15 | 58.11 ± 8.52 | 50.92 ± 13.05 | 37.77 ± 26.15 |
| RBD-chAb-28 | 58.51 ± 10.65 | 58.33 ± 11.2 | 94.07 ± 16.29 |
| RBD-chAb-45 | 5.292 ± 0.427 | 3.263 ± 0.298 | 17.99 ± 3.15 |

TABLE C-continued

| | $PRNT_{50}$ (ng/ml) | | |
|---|---|---|---|
| | B.1.1.7 (UK, Alpha) | P1 (Brazil, Gamma) | B.1.617.2 (India, Delta) |
| RBD-chAb-51 | 6.387 ± 0.818 | 2.921 ± 0.198 | 14.23 ± 3.15 |

Each assay was performed in triplicate and data are shown as mean ± SD.

Identification of Neutralizing Epitopes in the RBD

Figure 3:
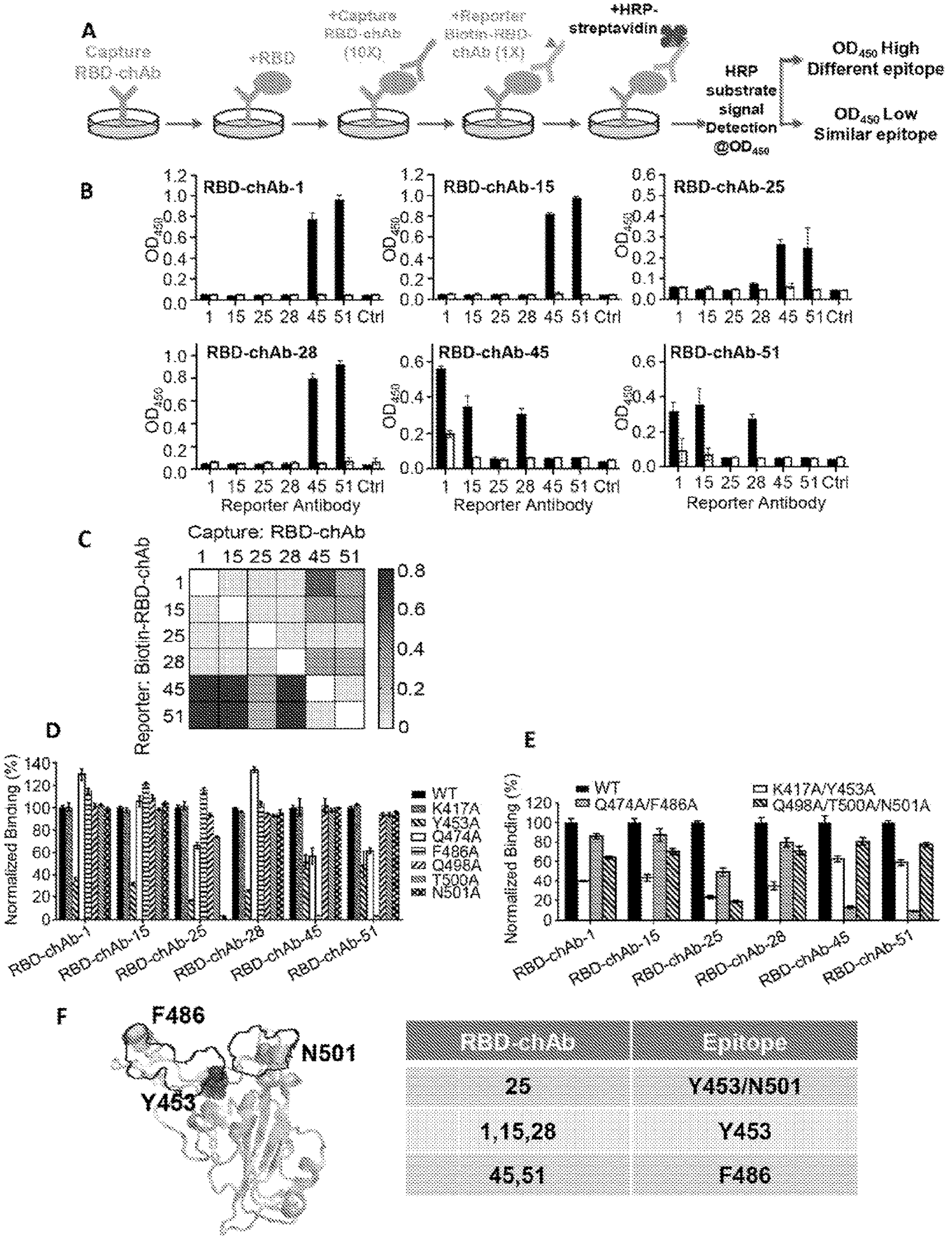
FIG. 3 shows epitope competitive inhibition and mapping of RBD complex formation for SARS-CoV-2-neutralizing chAbs. (A) Schematic illustration of the experimental design of the epitope competition-binding assay. First, RBD-His was captured by RBD-neutralizing chAbs on a 96-well plate. Second, 10-fold capture antibody was added to saturate the RBD. Third, biotinylated RBD-chAb was added to compete with capture RBD-chAb. Finally, HRP-conjugated streptavidin was added to bind the biotinylated reporter RBD-chAb, and competitive binding was detected by $OD_{450}$. (B) Results of triplicate epitope competition-binding assays for RBD-chAb-1, -15, -25, -28, -45, and -51. EpEX-His served as a negative control (Crtl: without biotin-RBD-chAb). (C) Heatmap of the epitope competition-binding assay results. The detected $OD_{450}$ values are colored, the scale bar in the right. (D-E) Epitope mapping of RBD-neutralizing antibodies by mutagenesis. Normalized binding to RBD alanine variants by RBD-chAbs with respect to that of wild type (WT). The human 293T cells were transiently transfected with wild-type or mutant RBD plasmids with combinatorial alanine mutations. The binding of RBD-chAbs to the RBD mutants was examined by cellular ELISA. (F) Structural mapping of key residues on the RBD responsible for the recognition by RBD-chAbs. The crystal structure of SARS-COV-2 S RBD in complex with ACE2 (PDB entry: 6M0J) is shown on the white/grey surface. Regions in the RBD within 4 Å of any atoms of ACE2 (defined as RBM) are outlined in black. The positions of the key residues, Y453, F486 and N501, are indicated.

An ELISA-based competition-binding assay was performed for the six most potent chAbs to examine whether they share overlapping epitopes (FIGS. 3A-C). The results suggested overlapping epitopes exist for RBD-chAb-1, 15 and -28; a similar finding was observed for RBD-chAb-45 and -51. The epitope for RBD-chAb-25 appears to partially overlap with that of RBD-chAb-1, 15 and -28 (FIGS. 3B-F). We classified the six chAbs into three distinct groups, each of which recognized a unique epitope on the RBD (FIGS. 3B-C). Structural analysis of ACE2 in complex with SARS-COV-2 S RBD indicated that K417, Y453, Q474, F486, Q498, T500, and N501 within the RBD make direct contacts with ACE2 forming part of the RBM. These residues are categorized into three clusters, namely Q498, T500 and NS01 at the proximal end of the RBM, K417 and Y453 in the middle of RBM, and Q474 and F486 at the distal end of the RBM (Yan et al., 2020 "Structural basis for the recognition of SARS-COV-2 by full-length human ACE2" Science 367, 1444-1448.). To dissect the contributions of these residues to the neutralizing effects of our RBD-chAbs, we carried out alanine scanning of the residues followed by ELISA to assess their impacts on RBD-chAb binding. The results showed that the singleton mutations at Y453 or N501 significantly decreased the binding signals for RBD-chAb-25, as did the mutation at Y453 for RBD-chAb1, -15, and -28 (FIG. 3D). Moreover, RBD-chAb-45 and -51 responded similarly to different singleton mutations, with the F486 mutation being the most disruptive, suggesting that RBD-chAb-45 and -51 bind to the same epitope (FIG. 3D). We generated combinations of singleton mutations and evaluated the effects on RBD-chAb binding. The K417A/Y453A and Q498A/T500A/N501A mutations were found to substantially reduce binding of RBD-chAb-25. The K417A/Y453A mutations had a similar effect on RBD-chAb1, 15, and -28. The Q474A/F486A mutations were more disruptive for RBD-chAb-45 and RBD-chAb-51 (FIG. 3E). These results suggest that the epitope residues recognized by RBD-chAb-25 are Y453 and N501, while the epitope residue of RBD-chAb1, 15, and -28 is Y453. Moreover, both RBD-chAb-45 and -SI recognize F486 of the RBD (FIG. 3F).

Neutralizing Abilities of Anti-RBD chAbs in Combination

To evaluate the neutralizing abilities of cocktails containing RBD-chAbs with different epitopes, we performed neutralization tests using SARS-COV-2 variant pseudoviruses. Combinations of RBD-chAb-15 or -28 with RBD-chAb-45 or -51 exhibited high neutralizing activities toward different SARS-COV-2 pseudoviruses, including Alpha, Beta, Gamma, Epsilon, Jota, Kappa and Delta variants (FIG. 4A). The RBD-chAb cocktails showed low $IC_{50}$ values ranging from 3 to 27 ng/ml (Table D). To evaluate the RBD-chAbs cocktail neutralization potential against the authentic SARS-COV-2 Alpha, Gamma, and Delta variants, we performed the PRINT and showed that RBD-chAb-15 or -28 combined with RBD-chAb-45 or -51 displayed the high potencies against the authentic virus; the $PRNT_{50}$ values were less than 38 ng/ml (FIG. 4B and Table E).

Tables D-1 and -2 present half-maximal inhibitory concentrations ($IC_{50}$) values for RBD-chAbs combination against pseudovirus of SARS-Cov-2 variants. Table E presents the 50% plaque reduction ($PRNT_{50}$) value for RBD-chAbs combination against Alpha, Gamma, and Delta variants of SARS-COV-2.

TABLES D-1

| | SARS-CoV-2 pseudovirus $IC_{50}$ (ng/ml) | | | |
|---|---|---|---|---|
| | D614G | B.1.1.7 (UK, Alpha) | B.1.351 (SA, Beta) | P1 (Brazil, Gamma) |
| RBD-chAb-15 + 45 | 7.41 ± 2.22 | 7.28 ± 1.40 | 4.27 ± 0.95 | 5.27 ± 2.82 |
| RBD-chAb-28 + 45 | 10.69 ± 1.83 | 11.77 ± 0.80 | 8.25 ± 1.43 | 5.40 ± 0.72 |
| RBD-chAb-15 + 51 | 4.76 ± 0.48 | 4.66 ± 1.25 | 3.55 ± 0.78 | 3.35 ± 0.55 |
| RBD-chAb-28 + 51 | 10.06 ± 2.71 | 12.72 ± 2.81 | 8.73 ± 2.84 | 4.19 ± 0.92 |

TABLES D-2

| | SARS-CoV-2 pseudovirus $IC_{50}$ (ng/ml) | | | |
|---|---|---|---|---|
| | B.1.429 (California, Epsilon) | B.1.526 (NY, Iota) | B.1.617.1 (India, Kappa) | B.1.617.2 (India, Delta) |
| RBD-chAb-15 + 45 | 6.31 ± 2.33 | 21.7 ± 5.36 | 19.35 ± 7.08 | 25.69 ± 8.73 |
| RBD-chAb-28 + 45 | 11.04 ± 0.90 | 6.81 ± 0.49 | 27.06 ± 1.81 | 21.55 ± 2.32 |
| RBD-chAb-15 + 51 | 5.86 ± 0.87 | 8.34 ± 0.2 | 20.29 ± 0.86 | 10.13 ± 1.25 |
| RBD-chAb-28 + 51 | 12.15 ± 2.67 | 11.44 ± 2.85 | 18.61 ± 4.24 | 14.22 ± 6.98 |

Data are from at least two independent experiments and are shown as mean ± SEM.

TABLE E

| | $PRNT_{50}$ (ng/ml) | | |
|---|---|---|---|
| | B.1.1.7 (UK, Alpha) | P1 (Brazil, Gamma) | B.1.617.2 (India, Delta) |
| RBD-chAb-15 + 45 | 9.43 ± 1.42 | 8.81 ± 1.07 | 37.54 ± 6.24 |
| RBD-chAb-28 + 45 | 4.93 ± 0.44 | 8.51 ± 0.73 | 20.58 ± 4.29 |
| RBD-chAb-15 + 51 | 6.86 ± 0.71 | 5.08 ± 0.51 | 15.63 ± 3.12 |
| RBD-chAb-28 + 51 | 5.27 ± 0.49 | 8.02 ± 0.51 | 5.63 ± 4.84 |

Each assay was performed in triplicate and data are shown as mean ± SD.

Cryo-EM Analysis of RBD-chAbs in Complex with SARS-COV-2 S Protein

Figure 5:
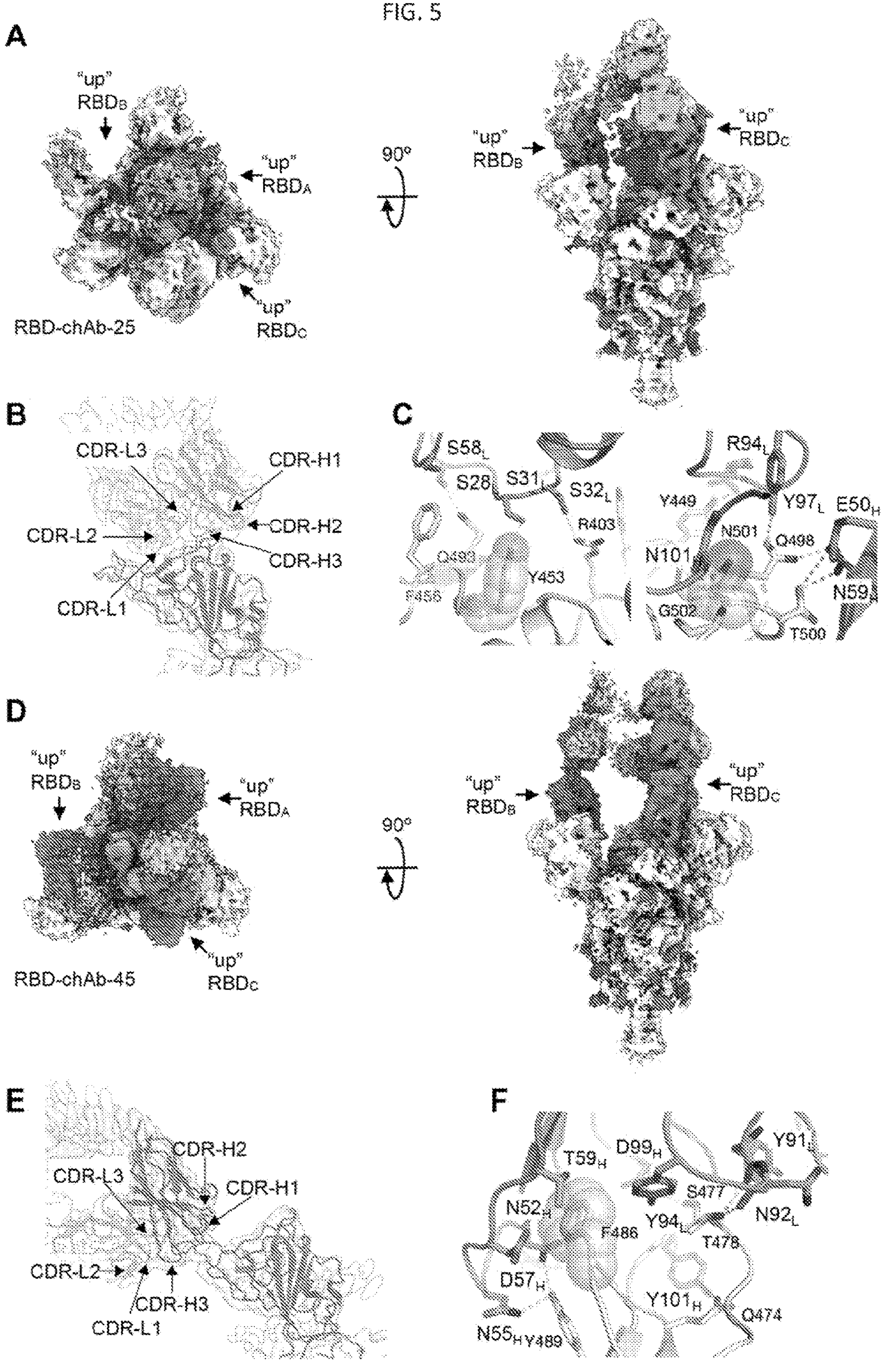
FIG. 5 shows Cryo-EM structure of RBD-chAb-25 and -45 in complex with SARS-Cov-2 S protein. (A, D) Orthogonal views of the EM maps of RBD-chAb-25 (A) and -45 (D) in complex with SARS-COV-2 S protein. The three RBDs are colored in blue, and the glycans are colored in green. The heavy chain and light chain of RBD-chAb-25 are colored in orange and pale yellow, respectively. The HC and LC of RBD-chAb-45 are colored in fuchsia and pink, respectively. (B, F) Expanded views of RBD-chAb-25 (B) and -45 (E) in complex with SARS-COV-2 S protein. The EM maps are shown as transparent surfaces with the atomic models shown as schematic representations. The positions of the CDR loops are indicated. (C, E) Atomic details of the molecular recognition of RBD-chAb-25 (C) and -45 (F). The side-chains of the key recognition residues on the RBD, Y453, F486 and N501, are indicated by transparent spheres. Intermolecular hydrogen bonds are shown as dashed yellow lines. The identities of individual residues are indicated and colored accordingly.

To reveal the structural basis of how the distinct classes of the RBD-chAbs recognize the SARS-CoV-2 S protein, we determined the cryo-EM structures of RBD-chAb-25 and -45 in complex with the ectodomain of the SARS-COV-2 S protein (FIGS. 5A-B). In both cases, the chAbs bound to the SARS-COV-2 S protein in a 3:3 stoichiometry, indicated by the three distinct EM densities protruding from the three RBDs, which were all in the open conformation. The overall nominal resolutions of the S-chAb complexes were between 3.6 and 3.5 Å (S-chAb-25 and S-chAb-45 complex, respectively, Table F). Focused refinement of the cryo-EM maps by masking the Fab and RBD to yield a better definition of the binding interface, thus enabling de novo model building of the Fabs and the S protein to define the atomic details of the epitopes of individual RBD-chAbs (FIGS. 5A-B). Table F presents parameters of cryo-EM data collection, processing and model validation.

TABLE F

| | S · chAb-45 | S · chAb-45 |
|---|---|---|
| Data Collection | | |
| Microscope | Titan Krios (Gatan K3 Summit camera) | |
| Voltage (keV) | 300 | |
| Mode | Counting | |
| Magnification | 81000x | |
| Dose rate ($e^-$/pix/s) | 8 | |
| Total dose ($e^-$/Å$^2$) | 48 | |
| Frames per movie | 50 | |
| Defocus range (μm) | 0.8-2.7 | 0.8-2.7 |
| Pixel size (Å) | 1.1 (2x binned) | |
| Micrographs collected | 3,444 | 5,195 |

TABLE F-continued

| | S · chAb-45 | S · chAb-45 |
|---|---|---|
| Micrographs used | 3,010 | 4,840 |
| Final used particles | 102,537 | 200,245 |
| Symmetry | C1 | C1 |
| Map Resolution (Å) | 3.6 | 3.5 |
| Model refinement and Validation | | |
| Model composition | | |
| Non-hydrogen atoms | 30,043 | 30,101 |
| Protein residues | 3,725 | 3,723 |
| Ligands | 75 | 72 |
| MolProbity score | 1.92 | 1.76 |
| Ramachandran (%) | | |
| Favored | 94.02 | 94.61 |
| Allowed | 5.93 | 5.25 |
| Outliners | 0.05 | 0.14 |
| Rotamer outliners (%) | 0.00 | 0.00 |
| Clashscore | 9.91 | 7.06 |
| r.m.s. deviations | | |
| Bond length (Å) | 0.002 | 0.002 |
| Bond angles (°) | 0.568 | 0.517 |
| Deposition | | |
| PDB code | 7EJ4 | 7EJ5 |
| EMDB code | EMD-30669 | EMD-30670 |

Detailed structural analysis showed that RBD-chAb-25 bound to the RBD via an extensive intermolecular hydrogen bond network around Y453 and N501 (FIG. 5C). Specifically, Y453, Q493 and R403 of the RBD were hydrogen bonded to $S31_L$, $S28_L$ and $S32_L$ of RBD-chAb-25 (subscript L denotes the light chain), respectively. Additionally, G502 (adjacent to N501) of the RBD and $N101_H$ of RBD-chAb-25 (subscript H denotes the heavy chain) formed a backbone-to-backbone hydrogen bond. A cluster of bipartite hydrogen bonds was also formed at the interface of the light chain ($Y97_L$) and heavy chain ($E50_H$ and $N59_H$) of RBD-chAb-25, with Q498 and T500 of the RBD. The overall binding interfaces between the RBD and the light/heavy chains of RBD-chAb-25 were 511 Å$^2$ and 350 Å$^2$, respectively. In the case of RBD-chAb-45, the phenyl ring of the key residue F486 on the RBD was encaged by the side chains of $Y94_L$, $N52_H$, $D57_H$, and $T59_H$ of RBD-chAb-45, adjacent to a bipartite hydrogen bond between Y489 of the RBD and $N52_H$, and $N55_H$ of RBD-chAb-45 in close proximity to F486 of the RBD (FIG. 5F). Additionally, T478 of the RBD was hydrogen-bonded to $Y91_L$ and $N92_L$ of RBD-chAb-45. The overall binding interfaces between the RBD and the light and heavy chains RBD-chAb-45 were 190 Å$^2$ and 362 Å$^2$, respectively.

Figure 6:
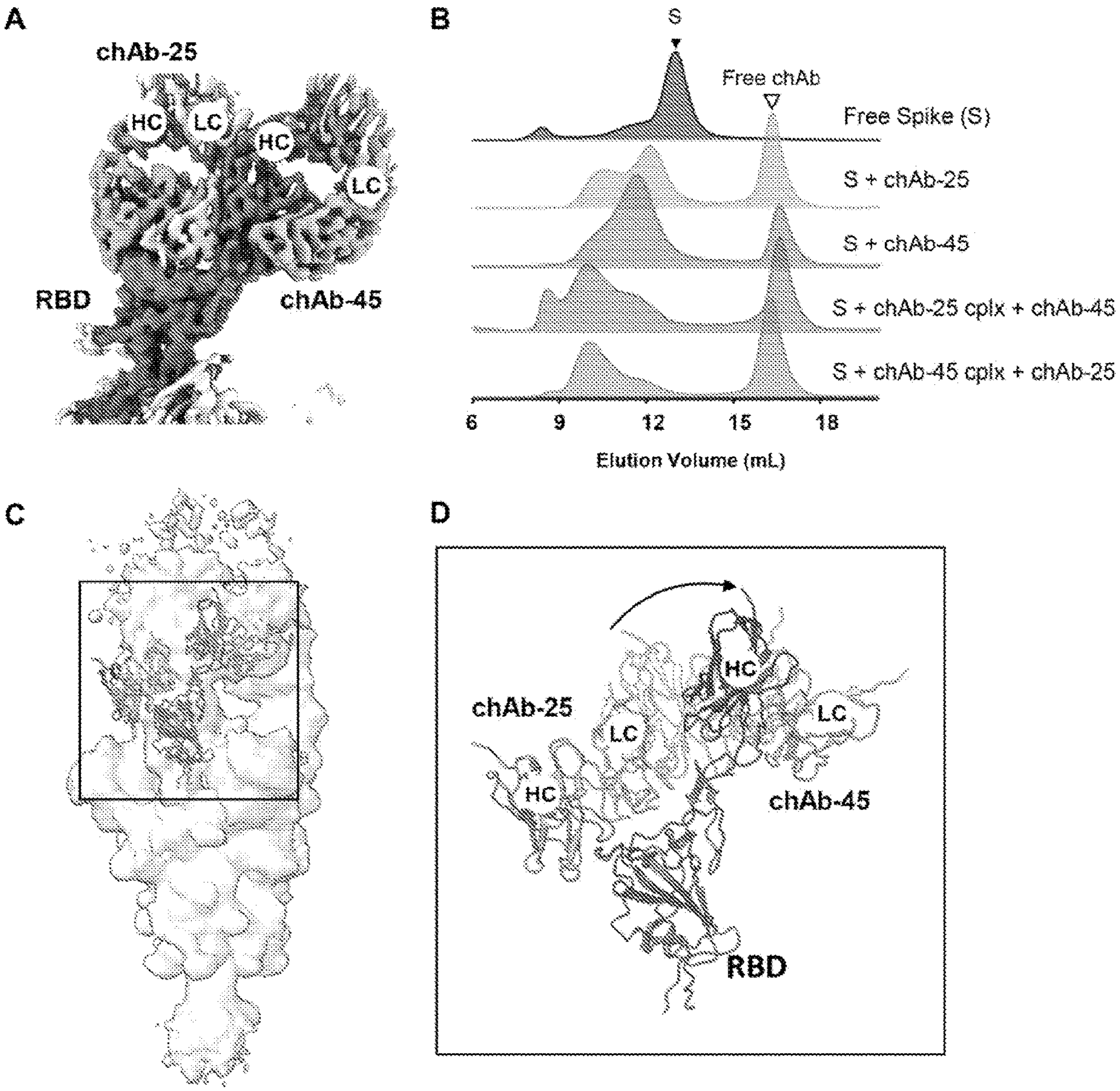
FIG. 6 shows structural and biophysical evidence of simultaneous binding of two RBD-chAbs to SARS-COV-2 S protein. (A) Overlay of cryo-EM maps of the Fabs of chAb-25 and -45 to the same RBD. The color scheme is the same as that of FIG. 4. (B) Size-exclusion chromatograms (SEC) of the free S protein (black), RBD-chAb-25-bound S protein (orange), RBD-chAb-45 bound S protein (fuchsia), addition of RBD-chAb-45 to pre-mixed RBD-chAb-25-bound S protein (green), and addition of RBD-chAb-25 to pre-mixed RBD-chAb-45-bound S protein (blue). Excess RBD-chAbs were added to the mixture, resulting in free RBD-chAb elution peaks, indicated by the open triangle. cplx, complex. (C) Cryo-EM map of the ternary complex of SARS-COV-2 S protein in complex with chAb-25 and 45 with the atomic models of the RBD, Fabs of chAb-25 and 45 fit to the EM map of one of the three protomers. The cartoon representations are colored in the same scheme as (A), (D) Expanded view of the cryo-EM map-derived structural model of RBD-bound to the Fabs of chAb-25 and 45 corresponding to the boxed region in (C). A rigid body rotation of chAb-45 relative to the singly bound chAb-45 (shown in transparent cartoon) is indicated by an arrow.

Despite some overlaps in the structural epitopes of RBD-chAb-25 and -45, superposition of the two resolved Fab structures onto the same RBD showed few steric clashes between the Fabs, suggesting that the two RBD-chAbs could bind simultaneously to the same RBD (FIG. 6A). In other words, RBD-chAb-25 and -45 could potentially be used in a cocktail to synergistically enhance their neutralizing effects. To verify their simultaneous binding, we mixed RBD-chAb-25 and SARS-COV-2 S protein and isolated the binary complex by SEC, followed by addition of RBD-chAb-45 for another round of SEC analysis (FIG. 6B). A clear shift in the elution volume of the main peak was observed, confirming the formation of a ternary complex, wherein RBD-chAb-25 and -45 bind simultaneously to the same SARS-COV-S protein, despite the limited space around the three RBDs to accommodate more than three chAbs (FIGS. 5A, 5D, 6B).

A similar finding was made when isolated RBD was used to form a quaternary complex with RBD-chAb-25 and -45 with more resolved SEC elution profiles (FIGS. 5C-D). The addition of RBD-chAb-25 or RBD-chAb-45 resulted a clear shift of the elution volume of the main elution peak, which indicated the formation of a stable binary complex between the RBD and the individual nAbs. Subsequent addition of a second nAb to a pre-formed RBD-nAb complex resulted in further shift of the elution volume to a higher molecular weight, indicating the formation of a ternary complex formed by two different nAbs and the RBD, regardless of the mixing sequence of the nAbs. The chromatographic data provided strong evidence of the ability of RBD-chAb-25 and -45 to simultaneously bind to the RBD.

To further verify the formation of a ternary complex between RBD-chAb-25 and -45 with the SARS-COV-2 S protein, we determined the cryo-EM map of the ternary complex that was purified by SEC (FIG. 6B, S-chAb-25 cplx+chAb-45). Although the resolution of the EM map was limited, in part due to the conformational heterogeneity of the nAbs in complex with the RBD, it was sufficient for us to dock the Fabs of RBD-chAb-25 and -45 onto the RBD, which revealed significant conformational rearrangements of the relative orientation of the Fab of chAb-45 with respect to the binary S-chAb-45 complex (FIGS. 6C-D). While the cryo-EM map of the ternary complex showed well-defined densities of the Fab of RBD-chAb-45 binding to all three RBDs, the EM map corresponding to the Fab of RBD-chAb-25 was less defined for some of the RBDs. The lack of well-defined cryo-EM map of RBD-chAb-25 could be attributed to either conformational heterogeneity or substoichiometric binding. The SEC and cryo-EM analyses provided good evidence of the simultaneous binding of RBD-chAb-25 and -45 to the SARS-COV-2 S RBD, that could serve as the basis for antibody cocktail therapy developments.

The N501Y Mutation Helps Evade Antibody Neutralization

Figure 7:
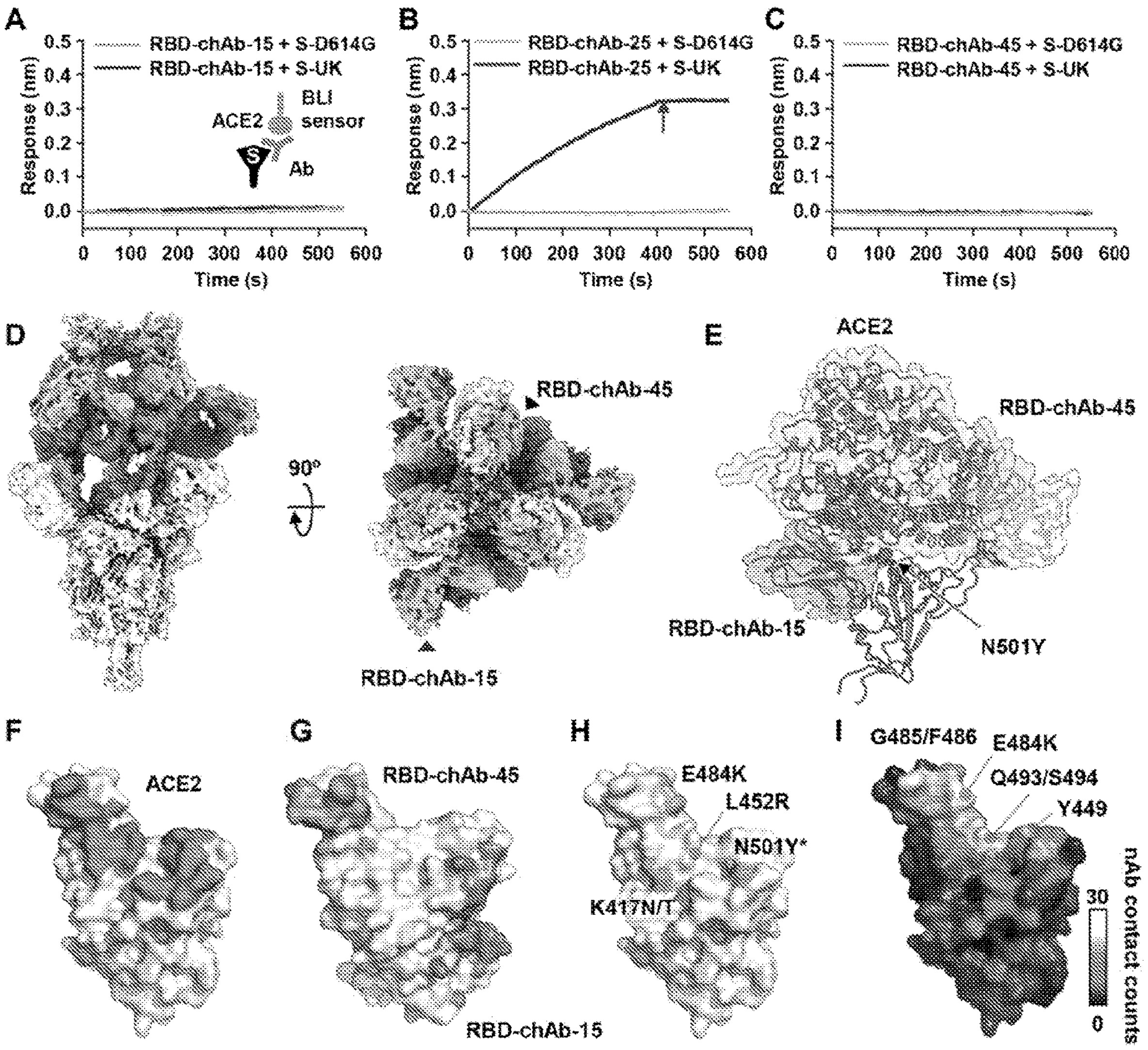
FIG. 7 shows neutralization of ACE2 binding by RBD-specific monoclonal antibodies, (A-C) BLI sensorgrams of immobilized ACE2 binding to S-D614G and 5-UK that were preincubated with RBD-chAb-15 (A), RBD-chAb-25 (B), and RBD-chAb-45 (C). Only S-UK preincubated with RBD-chAb-25 showed significant ACE2 binding, reflecting loss of neutralizing activity of RBD-chAb-25 due to the N501Y mutation. The grey arrow indicates the time point at which the dissociation of the complex was triggered (B). A schematic drawing in (A) illustrates the experimental design. (D) Orthogonal views of the eryo-EM map of S-D614G in complex with RBD-chAb-15 and 45 in a 3:3:3 binding stoichiometry, showing the three RBDs (blue), the heavy chain (amber) and light chain (yellow) of RBD-chAb-15, the heavy chain (forest green) and light chain (apple green) of RBD-chAb-45. (E) Superposition of cryo-EM structure of RBD-bound ACE2 (PDB 7KMS) and the quaternary complex of the antibody cocktail and RBD. The N501Y mutation site is shown in a red sphere. (F) Structural mapping of ACE2 binding interface (magenta), defined as the atoms within RBD that are within 5 Å of ACE2. (G) Structural mapping of antibody cocktail binding interface, showing the binding interface of RBD-chAb-15 (green) and RBD-chAb-45 (orange). (H) Structural mapping of clinically reported mutations within RBD associated with the VOCs B.1.1.7, B.1.351, P1 and B.1.617. The positions of the mutations are colored in orange. N501Y, the only RBD mutation of S-UK, is indicated by an asterisk. (I) Structural mapping of the contacting frequency of nAbs derived from convalescence sera. Forty-six cryo-EM or crystal structures of nAb-bound RBD were analyzed by PISA to define the intermolecular contacts. The frequency of nAb contacts from 0 (Red) to 30 (white) is indicated in the heatmap on the right. The positions such as E484K, Q493/S494, are marked in white (high frequency) and the bottom of structure are marked in red (low frequency). The identities of the most targeted residues are indicated.

We tested the abilities of three RBD-chAbs to compete with ACE2 binding to S-UK. We demonstrated that the RBD-chAb-15, -25 and -45 targeted three distinct sites within the RBM, that each of these RBD-chAbs potently neutralize pseudovirus of the original Wuhan strain of SARS-CoV-2, and that the cocktail of RBD-chAb-25 and -45 can prophylactically protect mice and hamsters from SARS-COV-2 infection. BLI analysis showed that pre-incubation of S-D614G with each of the three RBD-chAbs effectively prevented ACE2 binding. However, RBD-chAb-25 failed to compete ACE2 binding to S-UK while RBD-chAb-15 and -45 remained highly effective ACE2 binding inhibitors (FIGS. 7A-C). The loss of neutralizing activity of RBD-chAb-25 against S-UK can be rationalized by the overlap of its structural epitope and the N501Y mutation revealed by our cryo-EM analysis (FIG. 5C). Instead, epitopes targeted by RBD-chAb-15 and -45 reside on two distal ends of RBM, thus potentially allowing simultaneous binding to the same RBD. To verify our hypothesis, we sequentially mixed RBD-chAb-15 and -45 with S-D6140 shortly before cryo-EM grid vitrification, and determined the cryo-EM structure of the quaternary complex (S-D614G: RBD-chAb-15/45). The resulting cryo-EM map revealed stoichiometric binding of RBD-chAb-15 and -45 to all three RBDs, and the N501 was bypassed by the two RBD-chAbs (FIGS. 7D-7B). Despite the limited space above the three upward pointing RBDs to accommodate six antibodies, the poses of RBD binding by the two RBDs were essentially identical to that of individually bound cryo-EM structures, underscoring their potential to be used as a cocktail therapy for B.1.1.7.

Prophylactic Effect of RBD-chAb in SARS-COV-2-Infected Mice or Hamsters

Figure 8:
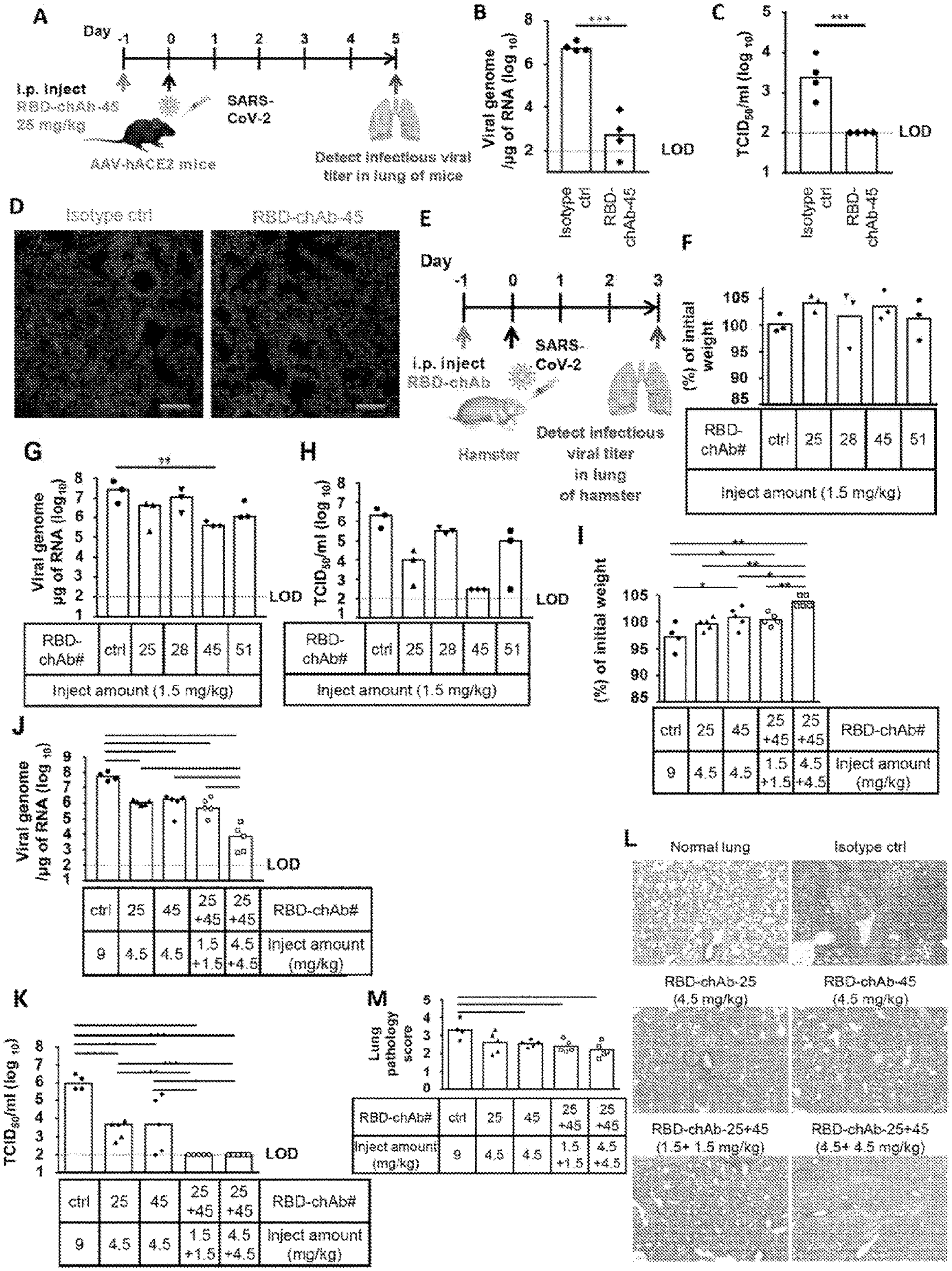
FIG. 8 shows prophylactic efficacy of neutralizing chAbs against SARS-COV-2 infection. (A) Illustration of the study design for prophylactic efficacy of RBD-chAb-45 against SARS-COV-2 in AAV-ACE2 mice. One day prior to intranasal (i.n.) challenge of SARS-COV-2, each group of mice was given a single intraperitoneal (IP) dose of 25 mg/kg of RBD-chAb-45 (n=4), or NHIgG, normal human IgG, as isotype control (n=4). On day 5 after virus inoculation, lung samples were collected for analysis. (B-C) The viral load in the lung of mice treated RBD-chAb-45 was determined by qRT-PCR and median tissue culture infectious dose per ml ($TCID_{50}$/ml) was calculated. (D) Viral antigen was detected by anti-SARS-COV-2 N protein mAb (red) in paraffin embedded lung tissue. Nuclear DNA was stained with DAPI (blue). (E) Illustration of the study design for prophylactic efficacy of RBD-chAb against SARS-COV-2 in hamsters. One day prior to i.n. challenge of SARS-COV-2, each group of hamster was given a single IP injection of RBD-chAbs (n=3 or 5), or NHIgG as isotype control (n=3 or 4). On day 3 after virus inoculation, lung samples were collected for analysis. (F) The percentage of body weight of hamsters treated single RBD-chAb were compared to the body weight in the day of virus inoculation. (G-H) The viral load in the lung of hamsters treated single RBD-chAb was determined by qRT-PCR and $TCID_{50}$/ml was calculated. (I) The percentage of body weight of hamsters treated cocktail RBD-chAbs were compared to the body weight on the day of virus inoculation. (J-K) The viral load in the lung of hamsters treated cocktail RBD-chAbs was determined by qRT-PCR and $TCID_{50}$/ml was calculated. (L-M) The pathologic changes in the lung were assessed by immunohistochemistry. All data points with the median are shown. *p<0.05, p<0.001 (Student's (-test). ctrl, isotype control. LOD, $1\times10^2$ TCID;/ml. Scale bars, 100 μm. The lung pathology score definition is shown Table G.

To assess the in vivo prophylactic potency against SARS-COV-2 infection, we selected RBD-chAb-45 for evaluation based on its high neutralization capacity. An adeno-associated virus (AAV)-mediated human ACE2-expressing (AAV-hACE2) mouse model was administered a single shot of 25 mg/kg antibody one day before SARS-Cov-2 infection (FIGS. 8A-D). The virus titer was significantly lower than controls and the PFU were undetectable in the treatment group at 5 days post-infection (FIGS. 8B-C). This result was confirmed by immunohistochemical staining of tissues from treated animals at 5 days post-infection (FIG. 8D), proving the potent in vivo neutralization activity of RBD-chAb-45 against SARS-COV-2.

We studied antibodies in a hamster model of mild human SARS-COV-2 infection. We administered a single IP injection of low-dose RBD-chAb-25, -28, -45 and -51 at 1.5 mg/kg one day prior to SARS-COV-2 infection (FIGS. 8E-H). The virus titer was determined from the lung tissue of each hamster at the third day after infection. Although no body weights were changed (FIG. 8F) and only RBD-chAb-45 caused a statistically significant decrease in the level of virus RNA measured by RT-qPCR (FIG. 8G), the $TCID_{50}$ values were decreased in all chAb-treated groups, and the effect was especially significant in the RBD-chAb-45-treated group at the third day post-infection compared to the control group (FIG. 8H). The efficacy of the cocktail of the two best RBD-chAbs (RBD-chAb-25 and -45) was assessed on hamsters (FIG. 8I-M). A single IP injection of 1.5 or 4.5 mg/kg both RBD-chAb or 4.5 mg/kg single RBD-chAb one day prior to SARS-COV-2 infection conferred dramatic protection, according to the infectious SARS-COV-2 titers at the third day post infection. Body weights were not changed in the group injected with 1.5 mg/kg antibody and may have even been slightly increased in the group receiving 4.5 mg/kg antibody (FIG. 8I). The virus RNA and $TCID_{50}$ values were decreased drastically in groups that received combinations of RBD-chAb-25 and -45 (1.5 or 4.5 mg/kg of each antibody, 3 or 9 mg/kg of total antibody at 3 days post-infection, FIGS. 8J-K). Lung pathology score definition is shown in Table G.

TABLE G

| Score | Lung status |
|---|---|
| 0 | Normal, no significant finding |
| 1 | Minor inflammation with a slight thickening of alveolar septa and sparse monocyte infiltration |
| 2 | Apparent inflammation, alveolus septa thickening with more interstitial mononuclear inflammatory infiltration |
| 3 | Diffuse alveolar damage, with alveolus septa thickening, and increased infiltration of inflammatory cells |
| 4 | Diffuse alveolar damage, with extensive exudation and septa thickening, shrinking of alveoli, the restricted fusion of the thick septa, obvious septa hemorrhage, and more cell infiltration in alveolar cavities |
| 5 | Diffuse alveolar damage, with massive cell filtration in alveolar cavities and alveoli shrinking, sheets of septa fusion, and hyaline membranes lining the alveolar walls |

Figure 9:
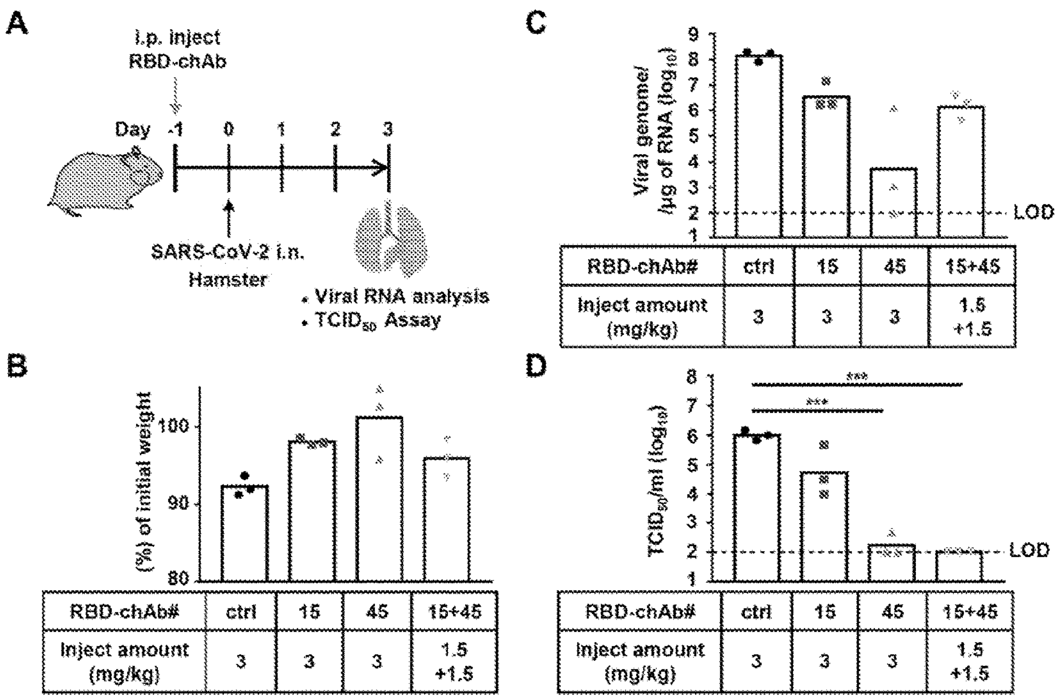
FIGS. 9A-D show prophylactic efficacy of neutralizing RBD-chAbs against SARS-COV-2 infection. (A) Illustration of the study design for prophylactic efficacy of RBD-chAb against SARS-CoV-2 in hamsters. One day prior to intranasal (i.n.) challenge of SARS-COV-2, each group of hamsters was given a single intraperitoneal injection of 3 mg/kg of RBD-chAb-15 (n=3), RBD-chAb-45 (n=3) or 3 mg/kg of RBD-chAb-15 combined RBD-mAb-45 (n=3), 3 mg/kg NHIgG as isotype control (n=3). On day 3 after virus inoculation, lung samples were collected for analysis. (B) The percentage of body weight of hamsters treated RBD-chAb were compared to the body weight in the day of virus inoculation. (C) The viral load in the lung of hamsters treated RBD-chAb was determined by qRT-PCR. (D) The viral load in the lung of hamsters treated RBD-chAb was determined by $TCID_{50}$/ml.

We examined the efficacies of the other two low-dose RBD-chAbs (RBD-chAb-15 and -45) individually and as a cocktail in the hamsters (FIGS. 9A-D). A single IP injection of one RBD-chAb alone (3 mg/kg) or RBD-chAb-15 and -45 in combination (1.5 mg/kg each) were made one day prior to WT SARS-COV-2 infection and conferred dramatic protection; infectious SARS-COV-2 titers were determined from the lung tissue at the third day post-infection. Body weights were not changed in groups receiving 1.5 mg/kg each of RBD-chAb-15 and -45 or 3 mg/kg single RBD-chAbs (FIG. 9B). However, the viral genome RNA (measured by RT-qPCR) could still be detected at the end of the experiment. Nevertheless, the infections SARS-COV-2 titers were just above the LOD ($1\times10^2$ $TCID_{50}$/ml) for almost all hamsters in the RBD-chAb cocktail-treated group (1.5 mg/kg of each RBD-chAb-15 and -45) at 3 days post-infection (FIG. 9D).

Figure 10:
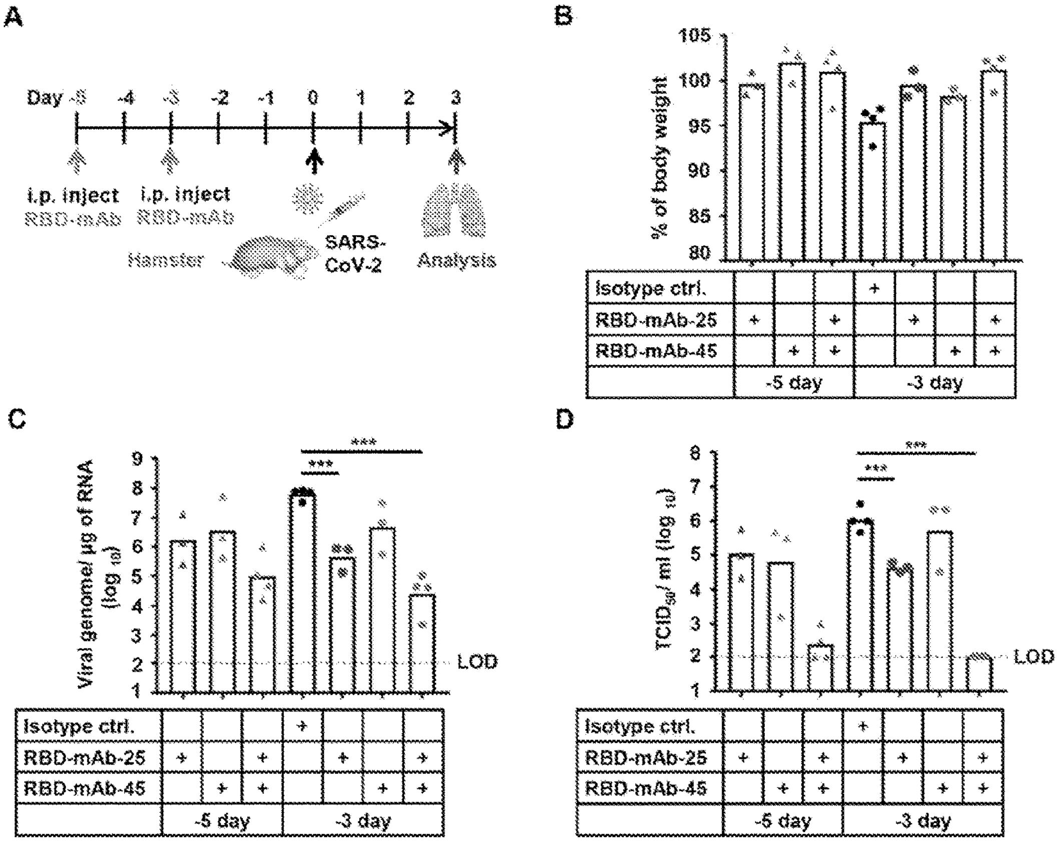
FIGS. 10A-D show prophylactic efficacy of mouse monoclonal neutralizing antibody cocktail against SARAS-Cov-2 infection in hamsters. (A) Illustration of the study design for prophylactic efficacy of monoclonal mouse antibodies, against SARS-COV-2 in hamster. Three or five days prior to i.n. challenge of SARS-Cov-2, each group of hamster was given a single IP dose of 1.5 mg/kg of RBD-mAb-25 (n=3), RBD-mAb-45 (n=3), or 3 mg/kg of RBD-mAb-25 combined RBD-mAb-45 (n=4), 3 mg/kg of NMIgG as isotype control (n=4). On day 3 after virus inoculation, body weights were recorded, and lung samples were collected for analysis. (B) The percentage of body weight were compared to the body weight in the day of virus inoculation. (C) The viral load in the lung was determined by qRT-PCR. (D) The infectious viral load in the lung was determined by $TCID_{50}$/ml was calculated. All data points with the median are shown. ***p<0.001, as determined by Student's t-test. ctrl, isotype control. LOD, $1\times10^a$ TCID5/ml.

A lower dose of neutralizing antibodies may induce antibody-dependent enhancement infection in SARS-COV-2 infected hamsters, we therefore tested 1.5 mg/kg of each RBD-mAb-25, -45, or the combination by treating hamsters at three or five days prior to i.n. challenge of SARS-COV-2 (FIG. 10A). No body weight loss was observed at the third day after the virus challenge (FIG. 10B) and significant reduction of viral load was observed (FIGS. 10C-D). When using the low dose of these two antibodies (1.5 mg/kg) or their combination (3.0 mg/kg), we did not find any of the neutralizing antibodies enhance disease. In groups receiving a combination of RBD-chAb-25 and -45, the neutralizing activity ($TCID_{50}$ values) exhibited a synergistic effect compared to those receiving single treatment of RBD-chAb-25 or ~45 (FIG. 8K and FIG. 10D).

Therapeutic Effect of RBD-chAb Cocktail in SARS-COV-2-Infected Mice or Hamsters

Figure 11:
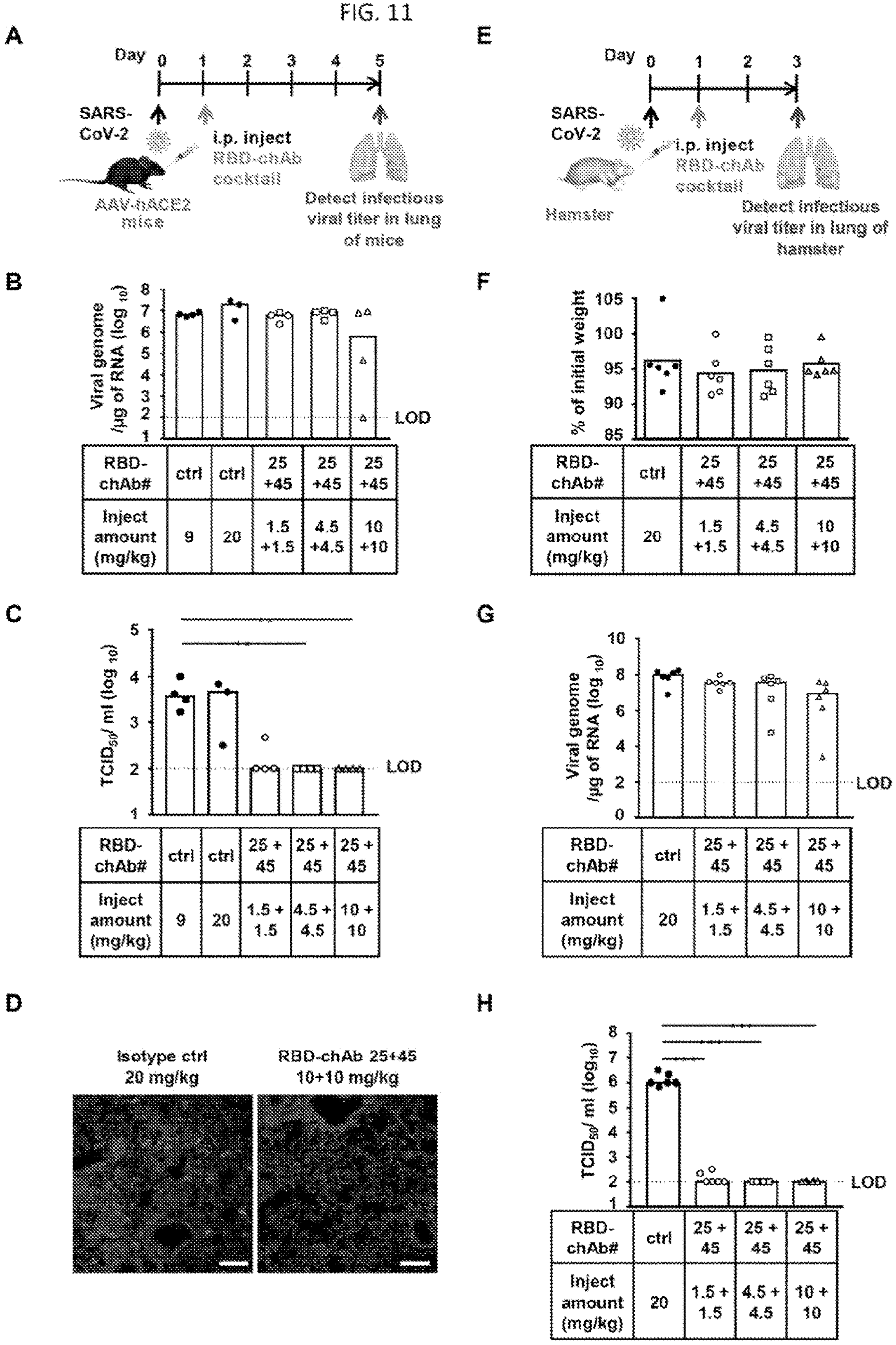
FIG. 11 show therapeutic efficacy of neutralizing chAbs against SARS-COV-2 infection. (A) Illustration of the study design for therapeutic efficacy of cocktail RBD-chAbs against SARS-COV-2 in AAV-hACE2 mice. One day after i.n. challenge of SARS-COV-2, each group of mice was given a single IP dose of 1.5, or 4.5, or 10 mg/kg of RBD-25+45 (n=4) or 9 or 20 mg/kg NHIgG, normal human IgG, as isotype control (n=7). (B-C) On day 5 after virus inoculation, the viral load in the lung of mice treated cocktail RBD-chAbs was determined by qRT-PCR and $TCID_{50}$/ml. (D) Viral antigen was detected by anti-SARS-COV-2 N protein mAb (red) in paraffin embedded lung tissue. Nuclear DNA was stained with DAPI (blue). (E) Illustration of the study design for therapeutic efficacy of cocktail RBD-chAbs against SARS-COV-2 in hamster. One day after i.n. challenge of SARS-COV-2, each group of hamsters was given a single IP dose of 1.5, or 4.5, or 10 mg/kg of each RBD-chAb (n=6), or 20 mg/kg NHIgG as isotype control (n=6). (F) The percentage of body weight of hamsters treated cocktail RBD-chAbs were compared to the body weight on the day of virus inoculation. (G-H) On day 5 after virus inoculation, the viral load in the lung of hamsters treated cocktail RBD-chAbs was determined by qRT-PCR and TOIDs/ml. All data points with the median are shown. p<0.01, *p<0.001 (Student's t-test). ctrl, isotype control. LOD, $1\times10^2$ $TCID_{50}$/ml. Scale bars, 100 μm.
Figure 12:
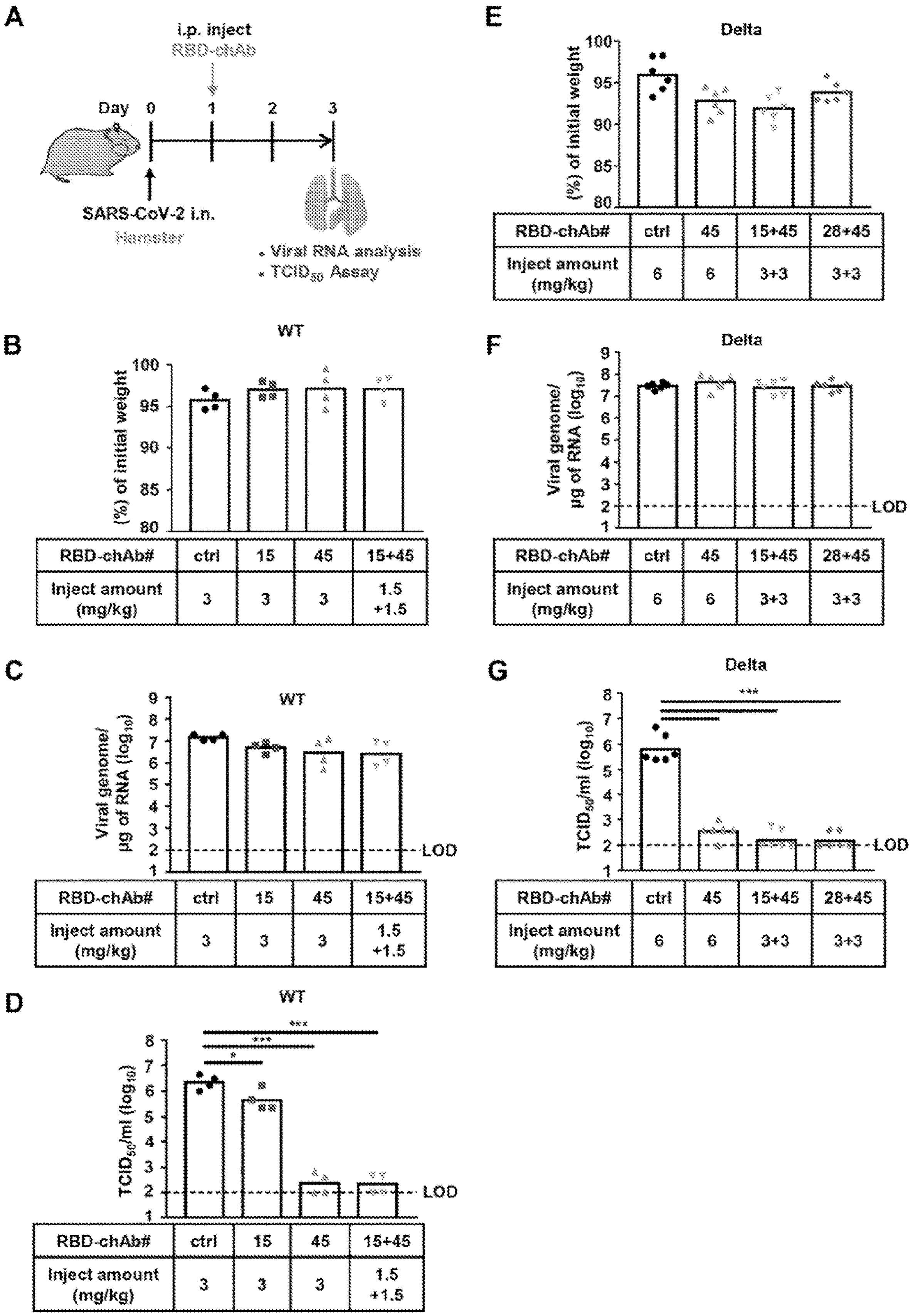
FIG. 12 show therapeutic efficacy of neutralizing RBD-chAbs against SARS-Cov-2 infection. (A) A schematic drawing showing the experimental design. (B-D) One day after intranasal (i.n.) challenge of SARS-COV-2, each group of hamsters was given a single IP injection of 3 mg/kg of RBD-chAb-15 (n=4), RBD-chAb-45 (n=4) or 3 mg/kg of RBD-chAb-15 combined RBD-mAb-45 (n=4), 3 mg/kg NHIgG as isotype control (n=4). (E-G) One day after i.n. challenge of Delta SARS-Cov-2 variant, each group of hamsters was given a single IP injection of 6 mg/kg RBD-chAb-45 (n=6), total of 6 mg/kg RBD-chAb-15 combined with RBD-chAb-45 (n=6), total of 6 mg/kg RBD-chAb-28 combined with RBD-chAb-45 (n=6), or 6 mg/kg NHIgG isotype control (n=6). B and E. The body weight of each treated hamster was compared to the body weight of that same animal on the day of virus inoculation. C and F, On day 3 after virus inoculation, the viral load in the lungs of treated hamsters was determined by qRT-PCR. D and G, On day 3 after virus inoculation, the viral load in the lungs of treated hamsters was determined by median tissue culture infectious dose per ml ($TCID_{50}$/ml).

We tested the effect of treating animals with antibody cocktail post SARS-Cov-2 infection. We treated the AAV-hACE2 mouse model with combinations of 1.5, 4.5, or 10 mg/kg of each RBD-chAb-25 and -45 at one day post-intranasal SARS-Cov-2 inoculation (FIG. 11A). Although the viral genome RNA could be detected, the infectious SARS-Cov-2 titers were close to the LOD ($1\times10^2$ $TCID_{50}$/ml) for all mice of the RBD-chAb cocktail-treated groups at 5 days post-infection (FIGS. 11B-C). The viral antigen contents were also assessed in lung tissue of mice treated with RBD-chAb cocktail (10 mg/kg of each antibody) using immunohistological assays, and no or very few viral antigens were detected (FIG. 11D).

We tested the therapeutic effects of the antibody cocktail administered after SARS-COV-2 infection in the hamster model (FIGS. 11B-H, 12). The infectious SARS-COV-2 titers were determined from the lung tissue at the third day post-infection. The levels of viral genome RNA could still be detected at the end of the experiment and the body weight showed a slight loss, similar to the control group (FIGS. 11F-G, 12B-C). The infectious SARS-COV-2 titers were close to the LOD ($1\times10^2$ $TCID_{50}$/ml) for all hamsters receiving low-dose RBD-chAb cocktail treatments (1.5 mg/kg each of either RBD-chAb-IS or -25 combined with RBD-chAb-45 for WT SARS-COV-2; 3 mg/kg each of either RBD-chAb-15 or -28 combined with RBD-chAb-45 for Delta SARS-COV-2) at 3 days post-infection (FIGS. 11H, 12D, and 12G). The data proved an additive neutralizing effect of the RBD-chAb cocktails which acted as prophylactic and therapeutic agents for SARS-COV-2 infection in animals.

In conclusion, the invention provides potent chAbs that target distinct structural epitopes within the RBD of SARS- COV-2 S protein. For WT SARS-COV-2, these chAbs effectively neutralized SARS-COV-2 in cell cultures with $PRNT_{50}$ values down to 6 ng/ml. The prophylactic and therapeutic potentials of the cocktail therapy were verified using SARS-COV-2-infected animal models. The top three neutralizing mAbs, namely RBD-chAb-28 (10.44 ng/ml), -45 (9.90 ng/ml), and ~51 (6.47 ng/ml), were better than previously reported nAbs, such as 47D11, BD-368-2, P2B-2F6 and P2B-1F11. RBD-chAb-45 and -51 represent the best in class nAb in terms of effective dosage for reducing viral RNA in animal models. Making collective contributions to the binding interface, RBD-chAb-25 and -45 essentially cover the entire RBM of spike protein. The combined use of these two Abs is expected to exhibit strong synergy in neutralizing SARS-COV-2. This synergistic neutralization was confirmed by the in vivo animal model studies (FIGS. 8K and 10D).

S-UK harbors N501Y mutation within RBM to disrupt binding by a subset of neutralizing antibodies, including RBD-chAb-25. Nevertheless, RBD-chAb-15 and -45 remained highly neutralizing in the context of competing ACE2 binding. The quaternary cryo-EM structure of S-D614G: RBD-chAb-15/-45 showed that the two antibodies can simultaneously bind to the same RBD without contacting the N501Y mutation site (FIG. 7D). RBD-chAb-45 targets the tip of the RBM where F486 resides. The ability of RBD-chAb-15 and -45 to simultaneously bind to distinct regions of RBD is an attractive feature for considering their use in prophylactic cocktail antibody therapy to prevent mutational viral escape. A cocktail of RBD-chAb-15 and -45 or RBD-chAb-25 and -45 also exhibits synergetic neutralizing ability, and this combination is likely to retain therapeutic potential for SARS-COV-2 mutants.

Figure 14:
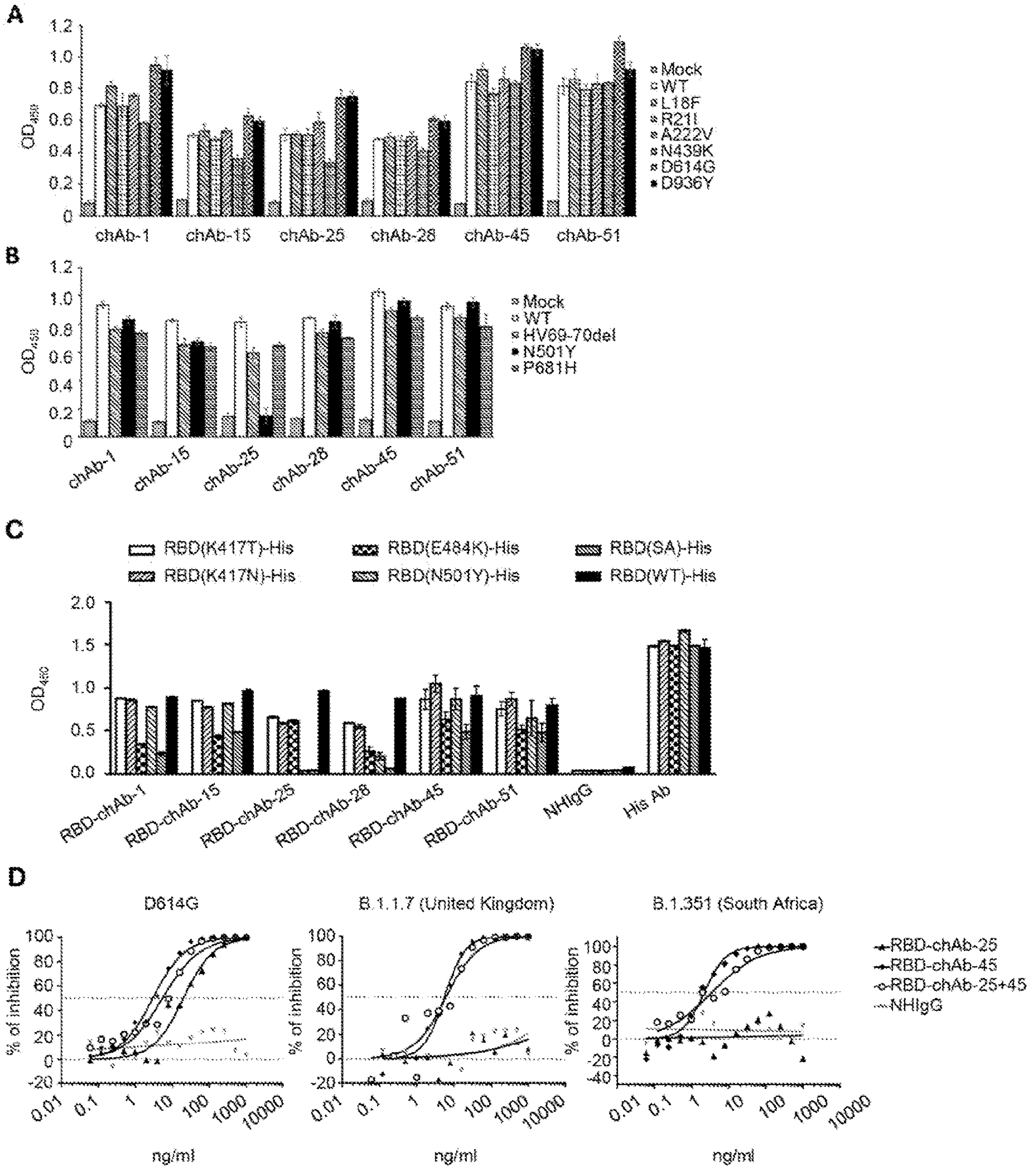
FIG. 14 show binding and neutralization assays of chAbs to diverse SARS-COV-2 mutants. (A-B) The binding ability of RBD-chAb to mutant S protein examined by cellular ELISA. The human 293T cells were separately transfected with the SARS-Cov-2 wild type (WT) or mutant as indicated. (C) Binding activity of anti-RBD chAbs determined by ELISA. Mutants of SARS-COV-2 RBD-His proteins were immobilized on 96-well plates prior to blocking with 1% BSA in PBS and incubated with anti-RBD chAbs at 100 ng/ml. Signal was detected ($OD_{450}$) after labeling with Donkey anti-human IgG-HRP secondary antibody. NHIgG, normal human IgG, as negative control. His Ab, as positive control. (D) Charts showing results of the neutralization assay for RBD-chAb-25, -45, or both using variants of SARS-CoV2 pseudoviruses as indicated. n=3

All six potent antibodies retained high binding signals when tested with S protein variants harboring some of the most common mutations on the GISAD sequencing database for COVID-19 on December 2020 (FIG. 14A). Nearly all of the antibodies retain the ability to recognize most common mutation variants, with only RBD-chAb-25 showing poor binding to the N501Y mutant (FIG. 14B). Several mutations within the RBD of SARS-Cov-2 (i.e., N501Y, K417N/K417T, L452R, T478K and E484K) are present in the highly transmissible VOCs. These mutations disrupt binding by several prominent nAbs, including REGEN10933, 2-15, LY-Cov555, and CT-P59. The antibodies, RBD-chAb-45 and -51, retain high binding ability for all tested SARS-COV-2 variant pseudoviruses, including four VOCs. Because the epitope for RBD-chAb-25 includes N501 in the S protein, the antibody had reduced binding ability toward variants with the N501Y mutation [including B.1.1.7 (Alpha), B.1.351 (Beta) and P1 (Gamma)]. However, RBD-chAb-25 still retained the ability to recognize other variants and retained the ability to recognize K417N/T and E484K mutant RBD proteins (FIGS. 2 and 14C).

Figure 4:
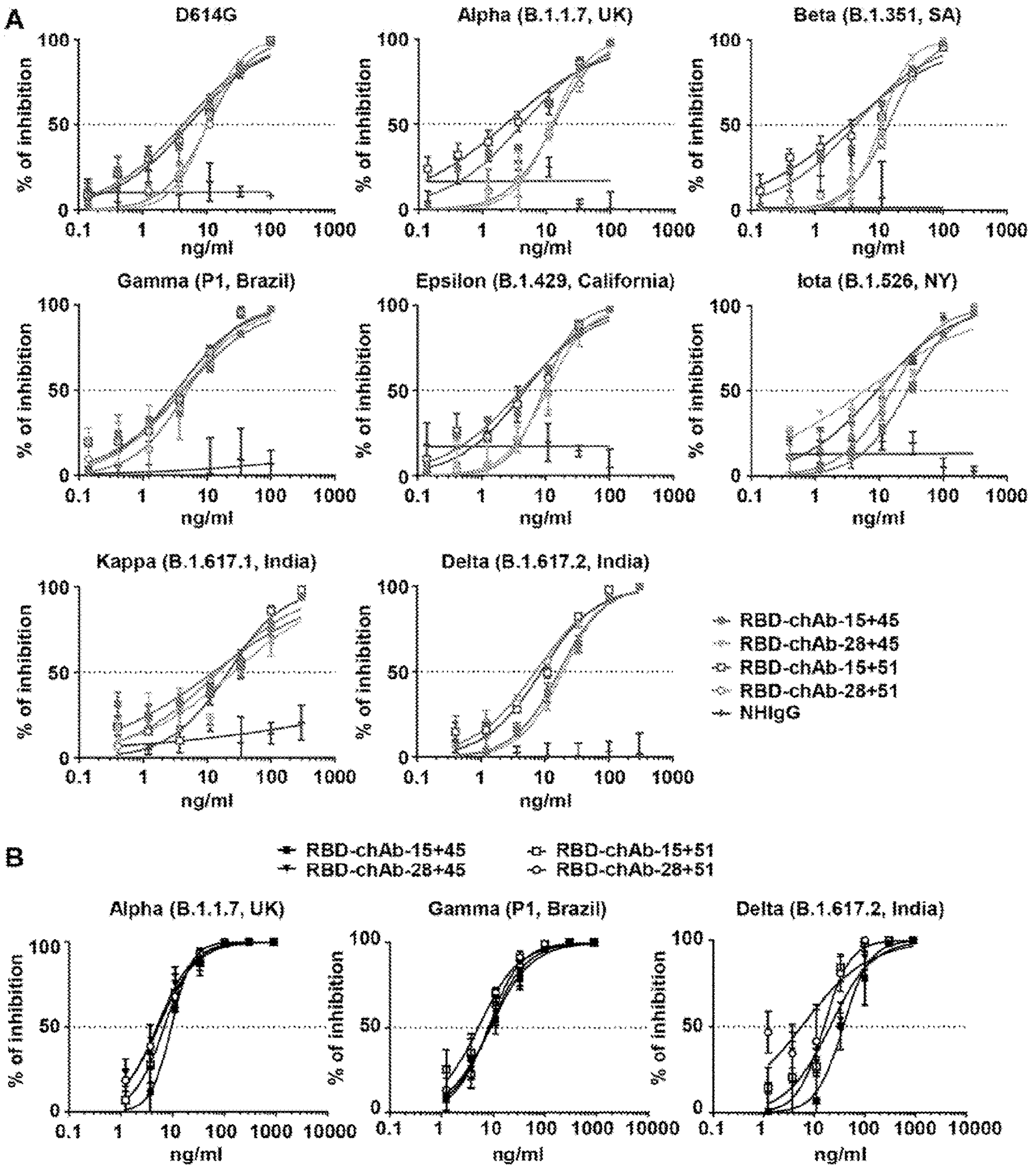
FIG. 4 shows neutralization of SARS-COV-2 variants by RBD-chAb combinations. (A) Neutralization assays testing RBD-chAb-15 or -28 combined with 45 or -51 against SARS-Cov-2 variant pseudoviruses. n=3. (B) Neutralizing RBD-chAb-15 or -28 combined with 45 or -51 inhibits SARS-COV-2 variants, Alpha, Gamma and Delta; infection was assessed by PRNT. n=3.

Combinations of RBD-chAbs showed neutralization ability for all tested SARS-COV-2 variants in the pseudovirus neutralization assay (FIG. 4). The cocktail showed $IC_{50}$ values close to those of RBD-chAb-45 only, meaning that the effect was not diminished due to the loss neutralization ability for RBD-chAb-25 (FIG. 14D). Although mutations of N501 could perturb the binding of RBD-chAb-25 to the RBD of SARS-COV-2, none of the reported mutations within the RBD overlaps with the epitope of RBD-chAb-45 (FIGS. 5C-F). The E484K mutation is not located within the binding surfaces of RBD-chAb-25 and RBD-chAb-45. Although the K417N/T mutation is located within the binding epitope of RBD-chAb-25, it is at the edge of the binding surface, and RBD-chAb-25 still retains the ability to bind the RBD (FIG. 14C). These findings suggest that the cocktail of RBD-chAb-25 and -45, RBD-chAb-15 and -45 or other our RBD-chAbs combination might be effective at overcoming drug resistance due to escape mutations. We have identified the Cryo-EM structure of RBD-chAb-15 in complex with SARS-Cov-2 S protein and found the combination of RBD-chAb-15 and -45 show a synergistic effect toward B.1.1.7 in the pseudovirus neutralization assay. Therefore, our six chimeric antibodies can be used strategically to create cocktail therapies against multiple SARS-COV-2 mutant strains.

Bamlanivimab received an EUA from the U.S. FDA to treat mild to moderate COVID-19 in adults and pediatric patients on Nov. 9, 2020. It exhibits high neutralization potency against the B.1.1.7 (Alpha) variant strain. Bamlanivimab is unable to block. B.1.351 (Beta), P.1 (Gamma), B.1.429 (Epsilon), B.1.526 (lota) and B.1.617.1 (Kappa) variants, due to the presence of E484K/Q or L452R mutations. Because many SARS-COV-2 viral variants are resistant to bamlanivimab, the U.S. FDA revoked the EUA for use of bamlanivimab alone to treat COVID-19 on Apr. 9, 2021.

Etesevimab (LY-CoV016) is a human IgG targeting the RBD of S protein that was identified from single B cells from a COVID-19 convalescent patient. The combination of bamlanivimab and etesevimab received an EUA from the U.S. FDA as it can neutralize B.1.1.7 (Alpha). The B.1.351 (Beta) and P.1 (Gamma) variants with K417N/T mutation are resistant to the cocktail of etesevimab and bamlanivimab. The B.1.351 (Beta) and P.1 (Gamma) variants are also resistant to casirivimab. In contrast, all of our neutralizing RBD-chAbs except RBD-chAb-25 could effectively block B.1.351 (Beta) and P.1 (Gamma) variants in the pseudovirus neutralization assay.

Sera from people who had received one dose of Pfizer or AstraZeneca vaccines barely inhibited variant B.1.617.2 (Delta). The levels of neutralizing antibodies in people with two vaccine doses were 3-5 fold lower when tested against B.1.617.2 (Delta) compared to B.1.1.7 (Alpha). Additionally, bamlanivimab does not have appreciable antiviral activity against B.1.617.2 (Delta) due to the L452R mutation, but etesevimab retains neutralization ability against the variant. As a result, the cocktail of bamlanivimab and etesevimab shows partially reduced neutralization ability against the B.1.617.2 (Delta) variant. Our neutralizing antibodies, RBD-chAb-1, -15, -25 and -28, also exhibited partially reduced neutralizing ability against the B.1.617.2 (Delta) variant. However, according to the pseudovirus neutralization assay, RBD-chAb-45 and -51 retained high neutralizing capabilities toward the B.1.617.2 (Delta) variant, with $IC_{50}$ values of about 8-15 ng/ml for single RBD-chAb treatments and 10-25 ng/ml for combination treatments.

RBD-chAb-15 and -45 have non-overlapping epitopes and can simultaneously bind to the same upward pointing RBD. Three each of the RBD-chAb-15 and -45 molecules can bind to the three RBDs in a SARS-Cov-2 UK variant S protein trimer (Yang et al. (2021b) "Impacts on the structure-function relationship of SARS-COV-2 spike by B.1.1.7 mutations" bioRxiv, 2021.2005.2011.443686). This suggested that RBD-chAb-15 and -45 could be used as a cocktail therapy for COVID-19. The cocktail of RBD-chAbs exhibited good neutralizing capability with low $IC_{50}$ values in SARS-COV-2 variant pseudovirus neutralizing experiments. The antibody cocktail of RBD-chAb-15 and -45 exhibited prophylactic and therapeutic effects in SARS- COV-2-infected hamsters. RBD-chAb-15 and -45 may be useful strategically to create cocktail therapies against multiple SARS-COV-2 variants.

The application provides disclosure that is hitherto unavailable to art. First, we determined the atomic structures of potent nAbs, namely RBD-chAb-15 and -45 or RBD-chAb-25 and -45 in complex with the SARS-COV-2 S protein, which revealed an unusual 3:3 binding stoichiometry. Both RBD-chAbs occupy all three RBDs to preclude ACE2 binding to the S protein, although RBD-chAb-25 is similar to REGEN10933 (one of the antibodies in the REGN-COV2 cocktail) with regard to its loss of neutralizing ability against SARS-COV-2 variants B.1.1.7, B.1.351 and P.1. Second, structure-guided design of cocktail therapy showed promising therapeutic effects in animal models. Based on these structural insights, we predict that the non-overlapping epitopes for RBD-chAb-15 and -45 or RBD-chAb-25 and -45 would provide improved protection from different SARS-Cov-2 variants, including Alpha, Beta, Gamma, and Delta variants. The epitope of RBD-chAb-45 is less utilized by other reported nAbs, making it an ideal candidate in antibody cocktail therapies.

All references cited and discussed in this specification are incorporated herein by reference in their entireties.

What is claimed is:

1. A human chimeric antibody (RBD-chAb), specifically against SARS-COV-2 Spike(S) receptor-binding domain (RBD), which is referred to as RBD-chAb-45, the RBD-chAb-45 comprising a heavy chain variable region ($V_H$) and a light chain variable region ($V_L$), wherein:
(i) the $V_H$ comprises the amino acid sequence of SEQ ID NO: 82; and
(ii) the $V_L$ comprises the amino acid sequence of SEQ ID NO: 83.

2. A human chimeric antibody (RBD-chAb) cocktail comprising the RBD-chAb of claim 1, and
one or more additional human chimeric antibodies (RBD-chAbs), specifically against SARS-COV-2 S RBD and is selected from the group consisting of: (1) RBD-chAb-28; (2) RBD-chAb-15; (3) RBD-chAb-25; (4) RBD-chAb-51; (5) RBD-chAb-1; and (6) any combination thereof;
wherein the RBD-chAb-28, RBD-chAb-15, RBD-chAb-25, RBD-chAb-51 and RBD-chAb-1 each comprise a $V_H$ and a $V_L$ as defined below:
(1) the RBD-chAb-28:
(i) the $V_H$ comprises the amino acid sequence of SEQ ID NO: 84; and
(ii) the $V_L$ comprises the amino acid sequence of SEQ ID NO: 85;
(2) the RBD-chAb-15:
(i) the $V_H$ comprises the amino acid sequence of SEQ ID NO: 86; and
(ii) the $V_L$ comprises the amino acid sequence of SEQ ID NO: 87;
(3) the RBD-chAb-25:
(i) the $V_H$ comprises the amino acid sequence of SEQ ID NO: 88; and
(ii) the $V_L$ comprises the amino acid sequence of SEQ ID NO: 89;
(4) the RBD-chAb-51:
(i) the $V_H$ comprises the amino acid sequence of SEQ ID NO: 90; and
(ii) the $V_L$ comprises the amino acid sequence of SEQ ID NO: 91;
(5) the RBD-chAb-1:
(i) the $V_H$ comprises the amino acid sequence of SEQ ID NO: 92; and
(ii) the $V_L$ comprises the amino acid sequence of SEQ ID NO: 93.

3. The RBD-chAb cocktail of claim 2, which comprises at least two RBD-chAbs selected from the group consisting of:
(1) RBD-chAb-45 and RBD-chAb-25;
(2) RBD-chAb-45 and RBD-chAb-15; and
(3) RBD-chAb-45 and RBD-chAb-28.

4. A human chimeric antibody (RBD-chAb), specifically against SARS-COV-2 S RBD protein, the RBD-chAb comprising the $V_H$ and the $V_L$ as defined in claim 2 and being selected from the group consisting of:
(1) RBD-chAb-45;
(2) RBD-chAb-28;
(3) RBD-chAb-15;
(4) RBD-chAb-25;
(5) RBD-chAb-51; and
(6) RBD-chAb-1.

5. A human chimeric antibody (RBD-chAb) cocktail, specifically against SARS-COV-2 S RBD protein, comprising more than one of the RBD-chAb of claim 4.

6. The RBD-chAb cocktail of claim 5, which comprises two RBD-chAbs selected from the group consisting of:
(1) RBD-chAb-45 and RBD-chAb-25;
(2) RBD-chAb-45 and RBD-chAb-15;
(3) RBD-chAb-45 and RBD-chAb-28;
(4) RBD-chAb-51 and RBD-chAb-15; and
(5) RBD-chAb-51 and RBD-chAb-28.

7. A human chimeric antibody (RBD-chAb) cocktail, comprising at least two human chimeric antibodies (RBD-chAbs), specifically against SARS-COV-2 S RBD protein, the at least two RBD-chAbs comprising the $V_H$ and the $V_L$ as defined in claim 2 and being any combination of RBD-chAbs selected from the group consisting of:
(1) RBD-chAb-45;
(2) RBD-chAb-28;
(3) RBD-chAb-15;
(4) RBD-chAb-25;
(5) RBD-chAb-51; and
(6) RBD-chAb-1.

8. The RBD-chAb cocktail of claim 7, wherein the at least two RBD-chAbs are selected from the group consisting of:
(1) RBD-chAb-45 and RBD-chAb-25;
(2) RBD-chAb-45 and RBD-chAb-15;
(3) RBD-chAb-45 and RBD-chAb-28;
(4) RBD-chAb-51 and RBD-chAb-15;
(5) RBD-chAb-51 and RBD-chAb-28;
(6) RBD-chAb-25, RBD-chAb-28, and RBD-chAb-45; and
(7) RBD-chAb-25, RBD-chAb-28, and RBD-chAb-51.

9. The RBD-chAb of claim 4, wherein the RBD-chAb-45, the RBD-chAb-28, the RBD-chAb-15, the RBD-chAb-25, the RBD-chAb-51 and the RBD-chAb-1 each comprise a $V_H$ and a $V_L$, the $V_H$ comprising $V_H$ CDR1, $V_H$ CDR2, and $V_H$ CDR3, and the $V_L$ comprising $V_L$ CDR1, $V_L$ CDR2, and $V_L$ CDR3, as defined below:
(1) the RBD-chAb-45:
(a) the $V_H$ CDR1, $V_H$ CDR2, and $V_H$ CDR3 comprise the amino acid sequence of SEQ ID NO: 33, SEQ ID NO: 35, and SEQ ID NO: 37, respectively; and
(b) the $V_L$ CDR1, $V_L$ CDR2, and $V_L$ CDR3 comprise the amino acid sequence of SEQ ID NO: 71, Ser Ala Ser (SAS), and SEQ ID NO: 74, respectively;
(2) the RBD-mAb-28:
(a) the $V_H$ CDR1, $V_H$ CDR2, and $V_H$ CDR3 comprise the amino acid sequence of SEQ ID NO: 26, SEQ ID NO: 28, and SEQ ID NO: 30, respectively; and
(b) the $V_L$ CDR1, $V_L$ CDR2, and $V_L$ CDR3 comprise the amino acid sequence of SEQ ID NO: 65, Tyr Thr Ser (YTS), and SEQ ID NO: 68, respectively;
(3) the RBD-mAb-15:
(a) the $V_H$ CDR1, $V_H$ CDR2, and $V_H$ CDR3 comprise the amino acid sequence of SEQ ID NO: 12, SEQ ID NO: 14, and SEQ ID NO: 16, respectively; and
(b) the $V_L$ CDR1, $V_L$ CDR2, and $V_L$ CDR3 comprise the amino acid sequence of SEQ ID NO: 53, Tyr Ala Ser (YAS), and SEQ ID NO: 56, respectively;
(4) RBD-mAb-25:
(a) the $V_H$ CDR1, $V_H$ CDR2, and $V_H$ CDR3 comprise the amino acid sequence of SEQ ID NO: 19, SEQ ID NO: 21, and SEQ ID NO: 23, respectively; and
(b) the $V_L$ CDR1, $V_L$ CDR2, and $V_L$ CDR3 comprise the amino acid sequence of SEQ ID NO: 59, Ser Thr Ser (STS), and SEQ ID NO: 62, respectively;
(5) the RBD-mAb-51:
(a) the $V_H$ CDR1, $V_H$ CDR2, and $V_H$ CDR3 comprise the amino acid sequence of SEQ ID NO: 40, SEQ ID NO: 42, and SEQ ID NO: 44, respectively; and (b) the $V_L$ CDR1, $V_L$ CDR2, and $V_L$ CDR3 comprise the amino acid sequence of SEQ ID NO: 77, Ser Ala Ser (SAS), and SEQ ID NO: 80, respectively; and (6) the RBD-mAb-1:

(a) the $V_H$ CDR1, $V_H$ CDR2, and $V_H$ CDR3 comprise the amino acid sequence of SEQ ID NO: 5, SEQ ID NO: 7, and SEQ ID NO: 9, respectively; and (b) the $V_L$ CDR1, $V_L$ CDR2, and $V_L$ CDR3 comprise the amino acid sequence of SEQ ID NO: 47, Trp Ala Ser (WAS), and SEQ ID NO: 50, respectively.

10. A neutralizing antibody or an antigen-binding fragment thereof, specifically against SARS-COV2 spike(S)-protein receptor-binding domain (RBD), comprising a $V_H$ domain and a $V_L$ domain, the $V_H$ domain and $V_L$ domain comprising the amino acid sequence as defined in claim 2, the neutralizing antibody or the antigen-binding fragment thereof being selected from the group consisting of:

(1) RBD-mAb-45;

(2) RBD-mAb-28;

(3) RBD-mAb-15;

(4) RBD-mAb-25;

(5) RBD-mAb-51; and (6) RBD-mAb-1.

11. The neutralizing antibody or antigen-binding fragment thereof of claim 10, which is a human chimeric antibody (RBD-chAb).

12. The neutralizing antibody or the antigen-binding fragment thereof of claim 10, which is a single-chain variable fragment, a Fab fragment, or a Fv fragment.

13. A vaccine composition, comprising the human chimeric antibody (RBD-chAb) of claim 1.

14. A vaccine composition comprising the human chimeric antibody (RBD-chAb) cocktail of claim 2.

15. A method for protection against COVID-19 infection, minimizing COVID-19 infection in lung, and/or treatment of COVID-19 in a subject in need thereof, comprising:

administering a therapeutically effective amount of the RBD-chAb cocktail of claim 2 to the subject in need thereof.

16. The composition of claim 13, wherein the RBD-chAb cocktail comprises RBD-chAbs selected from the group consisting of:

(1) RBD-chAb-25 and RBD-chAb-45;

(2) RBD-chAb-25, RBD-chAb-28, and RBD-chAb-45;

(3) RBD-chAb-25, RBD-chAb-28, and RBD-chAb-51; and (4) RBD-chAb-15 and RBD-chAb-45.

17. A vaccine composition, comprising the human chimeric antibody (RBD-chAb) cocktail of claim 3.

18. A vaccine composition, comprising the human chimeric antibody (RBD-chAb) cocktail of claim 5.

19. A vaccine composition, comprising the human chimeric antibody (RBD-chAb) cocktail of claim 7.

20. A vaccine composition, comprising the human chimeric antibody (RBD-chAb) cocktail of claim 8.

* * * * *